(12) United States Patent
Ho et al.

(10) Patent No.: US 7,351,739 B2
(45) Date of Patent: Apr. 1, 2008

(54) BIOACTIVE COMPOUNDS AND METHODS OF USES THEREOF

(75) Inventors: Chi-Tang Ho, East Brunswick, NJ (US); Naisheng Bai, Highland Park, NJ (US); Zigang Dong, Rochester, MN (US); Ann M. Bode, Cannon Falls, MN (US); Slavik Dushenkov, Fort Lee, NJ (US)

(73) Assignees: Wellgen, Inc., New Brunswick, NJ (US); The Regents of the University of Minnesota, Minneapolis, MN (US); Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 11/118,915

(22) Filed: Apr. 29, 2005

(65) Prior Publication Data

US 2006/0052438 A1    Mar. 9, 2006

Related U.S. Application Data

(60) Provisional application No. 60/567,340, filed on Apr. 30, 2004.

(51) Int. Cl.
| | |
|---|---|
| A01N 43/20 | (2006.01) |
| A01N 43/24 | (2006.01) |
| A61K 31/335 | (2006.01) |
| C07D 303/00 | (2006.01) |
| C07D 305/14 | (2006.01) |

(52) U.S. Cl. .................. 514/475; 549/332
(58) Field of Classification Search .............. 549/332; 514/475
See application file for complete search history.

(56) References Cited

U.S. PATENT DOCUMENTS

| | | | |
|---|---|---|---|
| 3,536,809 A | 10/1970 | Applezweig et al. |
| 3,598,123 A | 8/1971 | Zaffaroni et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,658,019 A | 4/1987 | Kung et al. |
| 5,017,691 A | 5/1991 | Lee et al. |
| 5,059,595 A | 10/1991 | Le Grazie |
| 5,073,543 A | 12/1991 | Marshall et al. |
| 5,120,548 A | 6/1992 | McClelland et al. |
| 5,136,021 A | 8/1992 | Dembinski et al. |
| 5,147,638 A | 9/1992 | Esmon et al. |
| 5,149,780 A | 9/1992 | Plow et al. |
| 5,196,511 A | 3/1993 | Plow et al. |
| 5,204,445 A | 4/1993 | Plow et al. |
| 5,223,395 A | 6/1993 | Gero |
| 5,231,024 A | 7/1993 | Moeller et al. |
| 5,262,520 A | 11/1993 | Plow et al. |
| 5,306,620 A | 4/1994 | Ginsberg et al. |
| 5,334,380 A | 8/1994 | Kilbourn et al. |
| 5,354,556 A | 10/1994 | Sparks et al. |
| 5,360,716 A | 11/1994 | Ohmoto et al. |
| 5,426,181 A | 6/1995 | Lee et al. |
| 5,436,154 A | 7/1995 | Barbanti et al. |
| 5,478,725 A | 12/1995 | Lessey |
| 5,498,694 A | 3/1996 | Ruoslahti |
| 5,523,209 A | 6/1996 | Ginsberg et al. |
| 5,578,704 A | 11/1996 | Kim et al. |
| 5,589,570 A | 12/1996 | Tamura et al. |
| 5,591,767 A | 1/1997 | Mohr et al. |
| 5,610,279 A | 3/1997 | Brockhaus et al. |
| 5,639,476 A | 6/1997 | Oshlack et al. |
| 5,644,034 A | 7/1997 | Rathjen et al. |
| 5,652,109 A | 7/1997 | Kim et al. |
| 5,652,110 A | 7/1997 | Kim et al. |
| 5,656,272 A | 8/1997 | Le et al. |
| 5,658,746 A | 8/1997 | Coan et al. |
| 5,665,393 A | 9/1997 | Chen et al. |

(Continued)

FOREIGN PATENT DOCUMENTS

EP          0 555 880          8/1993

(Continued)

OTHER PUBLICATIONS

Fujita et al., Chemical & pharmaceutical Bulletin, 1975, vol. 23, pp. 858-871.*

(Continued)

*Primary Examiner*—Margaret D. Seaman
*Assistant Examiner*—Niloofar Rahmani
(74) *Attorney, Agent, or Firm*—Jones Day

(57) ABSTRACT

In one aspect, the present invention provides compounds having formula I or IV as shown below:

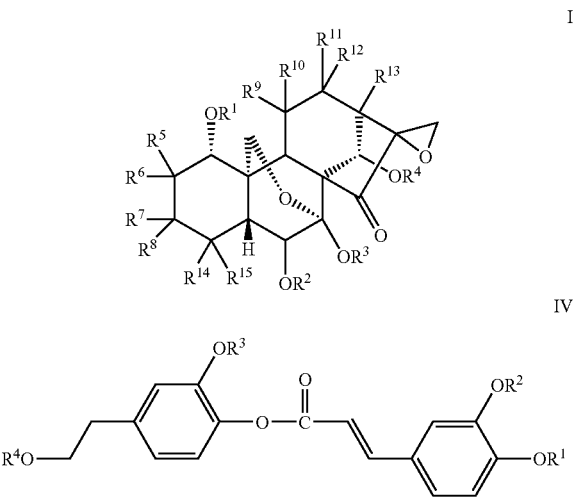

Figure 1:
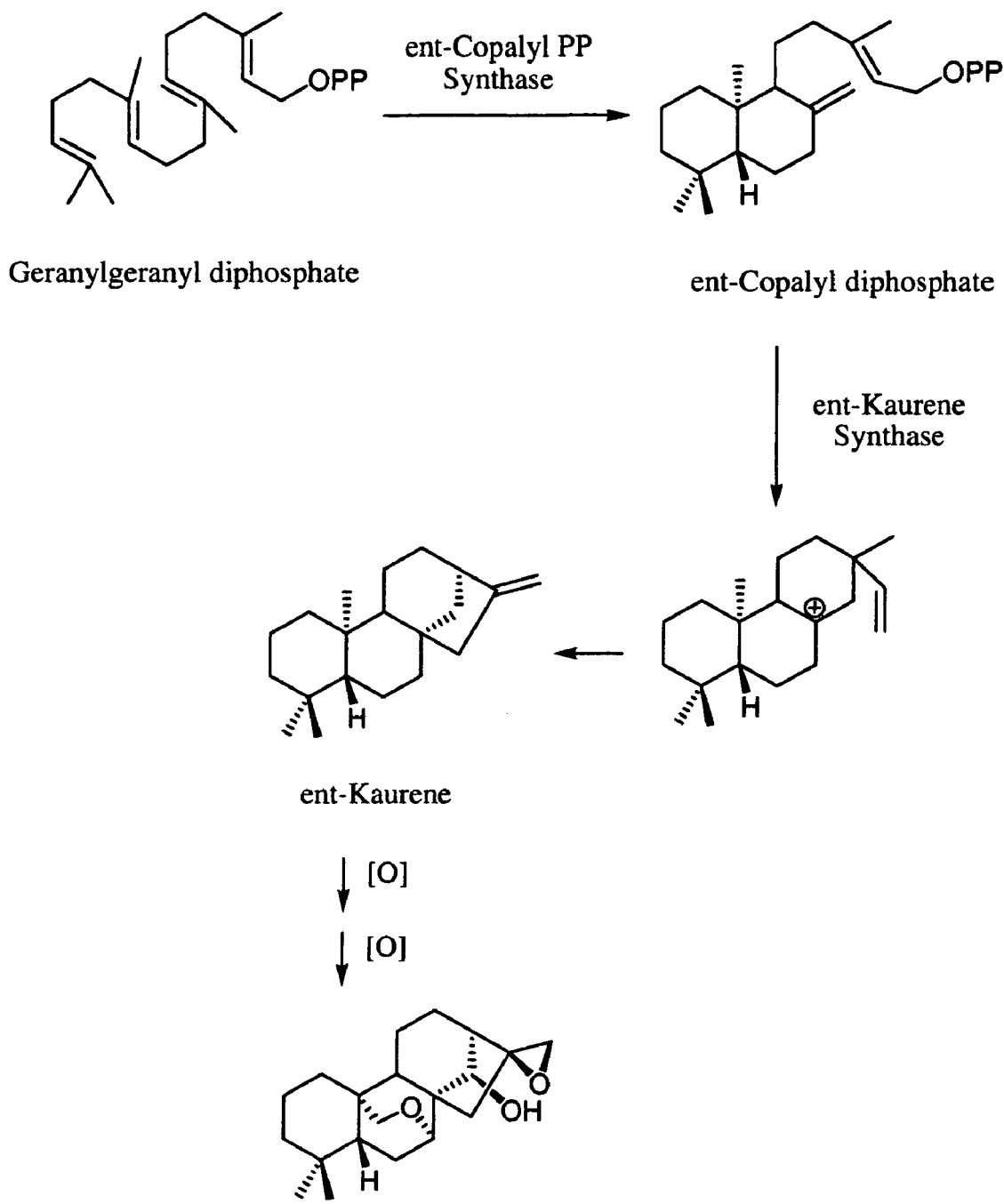

as further defined herein. In additional aspects, the present invention provides compositions and kits comprising the compounds of the invention and methods for their use, for example, for the prevention or treatment of a cancer.

9 Claims, 15 Drawing Sheets

U.S. PATENT DOCUMENTS

| | | | |
|---|---|---|---|
| 5,674,533 | A | 10/1997 | Santus et al. |
| 5,693,612 | A | 12/1997 | Jonczyk et al. |
| 5,698,195 | A | 12/1997 | Le et al. |
| 5,705,481 | A | 1/1998 | Jonczyk et al. |
| 5,733,566 | A | 3/1998 | Lewis |
| 5,736,138 | A | 4/1998 | Pfizenmaier et al. |
| 5,741,488 | A | 4/1998 | Feldman et al. |
| 5,753,230 | A | 5/1998 | Brooks et al. |
| 5,767,071 | A | 6/1998 | Palladino et al. |
| 5,770,565 | A | 6/1998 | Cheng et al. |
| 5,780,426 | A | 7/1998 | Palladino et al. |
| 5,808,029 | A | 9/1998 | Brockhaus et al. |
| 5,817,457 | A | 10/1998 | Bird et al. |
| 5,830,678 | A | 11/1998 | Carter |
| 5,849,692 | A | 12/1998 | Jonczyk et al. |
| 5,919,452 | A | 7/1999 | Le et al. |
| 5,955,269 | A | 9/1999 | Ghai et al. |
| 5,955,572 | A | 9/1999 | Ruoslahti et al. |
| 5,958,412 | A | 9/1999 | Welt et al. |
| 5,959,087 | A | 9/1999 | Rathjen et al. |
| 5,968,741 | A | 10/1999 | Plevy et al. |
| 5,985,278 | A | 11/1999 | Mitjans et al. |
| 5,994,510 | A | 11/1999 | Adair et al. |
| 6,036,978 | A | 3/2000 | Gombotz et al. |
| 6,048,861 | A | 4/2000 | Askew et al. |
| 6,090,944 | A | 7/2000 | Hutchinson |
| 6,096,707 | A | 8/2000 | Heino et al. |
| 6,114,517 | A | 9/2000 | Monia et al. |
| 6,130,231 | A | 10/2000 | Wityak et al. |
| 6,153,628 | A | 11/2000 | Jin et al. |
| 6,160,099 | A | 12/2000 | Jonak et al. |
| 6,162,432 | A | 12/2000 | Wallner et al. |
| 6,171,588 | B1 | 1/2001 | Carron et al. |
| 6,171,787 | B1 | 1/2001 | Wiley |
| 6,498,195 | B2 | 12/2002 | Rosen et al. |
| 6,627,623 | B2 | 9/2003 | Ho et al. |
| 6,790,869 | B2 | 9/2004 | Ghai et al. |
| 2003/0035851 | A1 | 2/2003 | Chen |

FOREIGN PATENT DOCUMENTS

| | | |
|---|---|---|
| WO | WO 93/08656 | 4/1993 |
| WO | WO 95/22543 | 8/1995 |
| WO | WO 98/33919 | 8/1998 |
| WO | WO 98/40488 | 9/1998 |
| WO | WO 98/46264 | 10/1998 |
| WO | WO 00/31248 | 6/2000 |
| WO | WO 00/78815 | 12/2000 |
| WO | WO 01/21137 | 3/2001 |
| WO | WO 02/39956 | 6/2002 |
| WO | WO 02/070007 | 9/2002 |
| WO | PCT/US05/15280 | 12/2006 |

OTHER PUBLICATIONS

Ashkenazi et al., 1991, "Protection Against Endotoxic Shock by a Tumor Necrosis Factor Receptor Immunoadhesin" Proc. Natl. Acad. Sci. USA 88:10535-10539.

Bai et al., Abstracts of Papers, 223rd ACS National Meeting, Orlando, FL, United States, Apr. 7-11, 2002: AGFD-093.

Bryant et al., 2000, "Development of Intermediate-Grade (Mantle Cell) and Low-Grade (Small Lymphocytic and Marginal Zone) Human Non-Hodgkin's Lymphomas Xenotransplanted in Severe Combined Immunodeficiency Mouse Models" Lab Invest 80(4):557-73.

Cao et al., 1996, "Kringle Domains of Human Angiostatin." Characterization of the anti-proliferative activity onp endothelial cells. J. Biol. Chem. 271:29461-29467.

Carrell, 1999, "How Serpins Are Shaping Up" Science 285:1861-1862.

Crowley et al., 1993, "Prevention of Metastasis by Inhibition of the Urokinase Receptor" Proc. Natl. Acad. Sci. USA 90:5021-5025.

de la Taille et al., 2000, Journal of Alternative & Complementary Medicine, 6(5): 449-51.

Dong et al. 1994, "Blocking of Tumor Promoter-Induced AP-1 Activity Inhibits Induced Transformation in JB6 Mouse Epidermal Cells" Proc. Natl. Acad. Sci. U.S.A. 91:609-613.

Dong et al., 1994, "Differential transformation efficiency but not AP-1 induction under anchorage-dependent and—independent conditions." Carcinogenesis 15:1001-1004.

Fodde & Smits, "Disease model: familial adenomatous polyposis." 2001, Trends Mol Med 7(8):369-73.

Ghaneh et al., 2001, "Adenovirus-mediated transfer of p53 and p16(INK4a) results in pancreatic cancer regression in vitro and in vivo." Gene Ther 8(3):199-208.

Goodson et al., 1994, "High-Affinity Urokinase Receptor Antagonists Identified with Bacteriophage Peptide Display" Proc. Natl. Acad. Sci. USA 91:7129-7133.

Hamburger et al., "Supercritical carbon dioxide extraction of selected medicinal plants—effects of high pressure and added ethanol on yield of extracted substances." Phytochemical Analysis (2004), 15(1), 46-54.

Han et al., 2003, "Ent-kaurane Diterpenoids from *Isodon rubescens* var: *lushanensis*" Chem. Pharm. Bull. 51(7): 790-793.

Han et al., 2003a, 2003, "Eng-Kaurane Diterpenoids from *Isodon rubescens*var. *Lushiensis*." Heterocycles, 60(4): 933-938.

Han et al., 2003b, "Two Novel ent-Kaurene Diterpenoids from *Isodon rubescens*" Helvetica Chimica Acta, 86(3): 773-777.

Han et al., 2004, "Two novel tricyclic diterpenoids from *Isodon rubescens* var. *taihangensis*." Tetrahedron 60: 2373-2377.

Han et al., 2004a, "Novel *ent*-kaurane dimers from *Isodon rubescens* var. *rubescens*." Tetrahedron Letters 45(13): 2833-2837.

Han et al.,, 2003, "Synthesis of Poly(aryl ether) Dendrimers and Studies on the In-tramolecuar Photosensitization" Huaxue Xuebao (Acta Chimica Sinica) 61(7): 1077-1082.

Han et al., 2003, "New *ent*-Kaurane Diterpenoids from *Isodon rubescens*." Youji Huaxue 23(3): 270-273.

Herber et al., 1996, "Squamous epithelial hyperplasia and carcinoma in mice transgenic for the human papillomavirus type 16 E7 oncogene" J Virol 70(3):1873-81.

Hosokawa et al., 2001, "In vivo analysis of mammary and non-mammary tumorigenesis in MMTV-cyclin D1 transgenic mice deficient in p53" Transgenic Res 10(5):471-8).

Hou et al., 2001, "Cytotoxic 7, 20-epoxy *ent*-kauranoids from *Isodon xerophilus*" Phytochemistry 58: 179-183.

Hough et al., 1998, "A model for spontaneous B-lineage lymphomas in $IgH_\mu$-*HOXII* transgenic mice" Proc Natl Acad Sci USA 95(23):13853-8.

Ikezoe et al., 2003, "Oridonin induces growth inhibition and apoptosis of a variety of human cancer cells." International Journal of Oncology, 23(4): 1187-1193.

Kado et al., 2001, "Intestinal microflora are necessary for development of spontaneous adenocarcinoma of the large intestine in T-cell receptor beta chain and p53 double-knockout mice." Cancer Res 61(6):2395-8.

Kohno et al., 1990, "A Second Tumor Necrosis Factor Receptor Gene Product can Shed a Naturally Occurring Tumor Necrosis Factor Inhibitor" Proc. Natl. Acad. Sci. USA 87:8331-8335.

Kuraguchi et al., 2000, "Tumor-associated Apc mutations in Mlh1-/- Apc1638N mice reveal a mutational signature of Mlh1 deficiency." Oncogene 19(50):5755-63.

Li et al., 2000a, "ent-Kaurene diterpenoids from *Isodon rubescens*." Phytochemistry 53(8): 855-859.

Li et al., 2000b, "Two new diterpenoids from *Isodon rubescens*" Chinese Chemical Letters, 11(1): 43-44.

Li et al., 2002 *ent*-Kaurane Diterpenoids from the Leaves of *Isodon xerophilus*.: Planta Med 68:946-948.

Li et al., 2002,, "A New Diterpenoid, Taibairubescensin C, from *Isodon rubescens*" Polish Journal of Chemistry 76(5): 721-724.

Liu et al., 2000, "A New Diterpene Glycoside from *Rabdosia rubescens*." Chemical & Pharmaceutical Bulletin 48(1): 148-149.

Liu et al., 2000, "Rubescensin H, A new diterpenoid extracted from *Isodon rubescens*." Tianran Chanwu Yanjiu Yu Kaifa 12(2):4-7.

Meade-Tollin et al., 2004, "Ponicidin and oridonin are responsible for the antiangiogenic activity of *Rabdosia rubescens*, a constituent of the herbal supplement PC SPES." Journal of Natural Products, 67(1): 2-4.

Min et al., 1996, "Urokinase receptor antagonists inhibit angiogenesis and primary tumor growth in syngeneic mice" Cancer Res. 56:2428-2433.

Morris et al., "Lung-specific expression in mice of a dominant negative mutant form of the p53 tumor suppressor protein." 1998, J La State Med Soc 150(4):179-85.

O'Reilly et al. 1999, "Antiangiogenic Activity of the Cleaved Conformation of the Serpin Antithrombin" Science 285:1926-1928.

Oswald et al. 1992, "Interleukin 10 Inhibits Macrophage Microbicidal Activity by Blocking the Endogenous Production of Tumor Necrosis Factor αRequired as a Costimulatory Factor for Interferon γ-Induced Activation" Proc. Natl. Acad. Sci. USA 89:8676-8680.

Schwarz et al., 2003 "Pancreatic cancer in vitro toxicity mediated by Chinese herbs SPES and PC-SPES: implications for monotherapy and combination treatment." Cancer Letters 189: 59-68.

Seckinger et al., "Characterization of a Tumor Necrosis Factor α(TNF-lalpha) Inhibitor: Evidence of Immunological Cross-Reactivity with the TNF Receptor" 1990, Proc. Natl. Acad. Sci. USA 87:5188-5192.

Shi et al., 2001, "Natural diterpenoid ludongnin, octahydro-5'-hydroxy-7a-methyl-8'-methylenespiro [isobenzfuran- 4(1H), 4'(3H')-[1H-7,9a]methanocyclohepta[*c*]pyran]-1'3,9'2a*H*,4'a*H*)-trione." Acta Crystallographica Soc. (Structure Reports) 57(8): 685-687.

Simandi et al., Recents Progres en Genie des Procedes (1999) 13(71), 157-164.

Thorbecke et al., 1992, "Involvement of Endogeneous Tumor Necrosis Factor αand Transforming Growth Factor β During Induction of Collagen Type II Arthritis in Mice" Proc. Natl. Acad. Sci. USA 89:7375-7379.

Wang et al., 1993, "A Report of 40 cases of Esophageal Carcinoma Surviving for more than 5 years after Treatment with drugs." Chung-Hua Chung Lin TSA Chin. 1993, 15(4), 300-302.

Wang et al., 2001, "A novel, clinically relevant animal model of metastatic pancreatic adenocarcinoma biology and therapy." Int J Pancreatol 29(1):37-46.

Williams et al., "Synergy between Anti-CD4 and Anti-Tumor Necrosis Factor in the Amelioration of Established Collagen-Induced Arthritis" 1994, Proc. Natl. Acad. Sci. USA 91: 2762-2766.

Xiang et al, 2003, "Cytotoxic Diterpenoids from *Isodon enanderianus*." Planta Med 69: 1031-1035.

Yen et al., 1994, "Scavenging Effect of Methanolic Extracts of Peanut Hulls on Free-Radical and Active-Oxygen Species." J. Agric. Food. Chem. 42:629-632.

Yokota et al., 1986, "Isolation and Characterization of a Human Interleukin cDNA Clone, Homologous to Mouse B-Cell Stimulatory Factor 1, that Expresses B-Cell- and T-Cell-Stimulating Activities" Proc. Natl. Acad. Sci., USA, 83:5894-5898.

Yu et al, 1995, "Preliminary study of the effect of selected Chinese natural drugs on human ovarian cancer cells." Oncology Reports 2(4): 571-575.

Zhang & Roth ,1994, "Anti-oncogene and tumor suppressor gene therapy—examples from a lung cancer animal model." In Vivo 8(5):755-69.

Zhao et al., 2000, "Study on water-soluble components, amino acid and inorganic elements in *Rabdosia rubescens* [Hamsl.] Hara." Henan Yike Daxue Xuebao, 35(2): 138-139.

Zhong Hua Ben Cao, 1999, vol. 7, pp. 150-514,, Shanghai Science and Technology Press.

Zhong Hua Ben Cao, 1999, vol. 7, pp. 553-561, Shanghai Science and Technology Press.

Helm et al., J. Agric. Food Chem. 41:570-576 (1993).

Xian-Rong et al., Phytochemistry 38:921-926 (1995).

Stedman's Medical Dictionary, 27th ed., (Lippincott Williams & Wilkins), 2000, p. 1654.

Bai, N., *Thesis (Ph.D.) Dissertation submittd to Rutgers University Library*, "Natural Product Chemistry of Medicinal Herbs *Rabdosia rubescens* and *Inula britannica*" (Online Computer Library Center (OCLC) entry date Jan. 6, 2004).

Webster's Third New International Dictionary, 1986, p. 2171, Merrian-Webster Inc., Springfield, MA, USA.

Dorland's Illustrated Medical Dictionary, 29th Edition, 2000, p. 1663, W.B. Saunders Company, Philadelphia, PA, USA.

Academic Press Dictionary of Science and Technology, 1992, p. 2033, Academic Press, Inc., San Diego, CA, USA.

Hackh's Chemical Dictionary, 4th Edition, 1969, p. 624, McGraw-Hill Book Co., New York, NY, 1969.

* cited by examiner

BIOACTIVE COMPOUNDS AND METHODS OF USES THEREOF

This application claims the benefit of U.S. provisional application 60/567,340, filed Apr. 30, 2004, which is incorporated herein by reference in its entirety.

1. TECHNICAL FIELD

The present invention relates to depside and diterpenoid compounds and methods for the prevention or treatment of, for example, a proliferative disorder, e.g., cancer, or symptom thereof. Pharmaceutical, nutraceutical and cosmetic compositions comprising depside and/or diterpenoid compounds are also encompassed.

2. BACKGROUND

*Rabdosia rubescens* (Hemsl.) Hara (*donglingcao*) (family Labiatae), formerly known as *Isodon rubescens*, is a Chinese medicinal herb. The aerial parts of *R. rubescens* and other species of the same genus were observed to have the functions of clearing heat and toxicity, nourishing "yin", removing blood stasis, and relieving swelling.

*R. rubescens* has been used to treat stomach ache, sore throat, cough, esophagal cancer, breast cancer, liver cancer, and prostate cancer (Yu et al., 1995, Oncology Reports 2(4): 571-575; Zhong Hua Ben Cao, 1999, vol. 7, pp.150-514, and 553-561, Shanghai Science and Technology Press). *R. rubescens* increased survival and reduced side effects in patients with esophageal carcinoma. (Wang et al., 1993, Chung-Hua Chung Lin TSA Chin. 1993, 15(4), 300-302). *R. rubescens* is one of the eight herbs used in PC-SPES, an herbal formula promoted as a treatment for prostate cancer, see U.S. Pat. No. 5,665,393.

A number of studies reported attempts to identify biomedically useful compounds from *E. rubescens*. Rubescensin A (oridonin) and rubescensin B (ponicidin) are two compounds identified in *R. rubescens* extract, which have been tested for cytotoxicity against cancer cell lines in vitro. Both compounds have also been shown to be anti-angiogenic. (Meade-Tollin et al., 2004, Journal of Natural Products, 67(1): 2-4).

Citation or identification of any reference in this or any other section of this application shall not be construed as an admission that such reference is available as prior art to the present invention.

3. SUMMARY

In one aspect, the present invention provides compounds useful for the prevention or treatment of a proliferative disorder, e.g., a cancer, or symptom thereof in a subject.

In certain embodiments, the present invention provides a compound having formula I as described below:

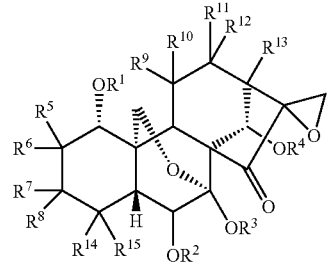

I or a pharmaceutically or physiologically acceptable salt, solvate, or hydrate thereof, wherein $R^1$, $R^2$, $R^3$ and $R^4$ are each independently hydrogen, $(C_1-C_6)$alkyl, or $(C_1-C_{12})$acyl;

$R^5$, $R^6$, $R^7$, $R^8$, $R^9$, $R^{10}$, $R^{11}$, $R^{12}$ and $R^{13}$ are each independently hydrogen, hydroxyl, $(C_1-C_6)$alkyl, or $(C_1-C_6)$alkylcarboxyl; and $R^{14}$ and $R^{15}$ are each independently hydrogen or $(C_1-C_6)$alkyl.

In some embodiments, the present invention provides compounds according to formula II as described below:

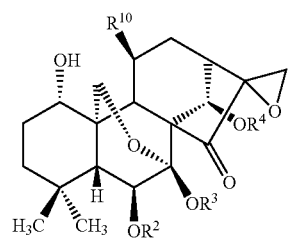

II or a pharmaceutically or physiologically acceptable salt, solvate or hydrate thereof, wherein $R^2$, $R^3$, $R^4$ and $R^{10}$ are as defined above in formula I.

In particular embodiments, the present invention provides a compound having the following structure:

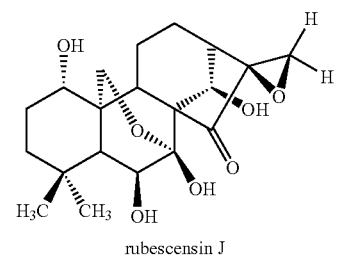

rubescensin J

In certain embodiments, the present invention provides a compound having formula III:

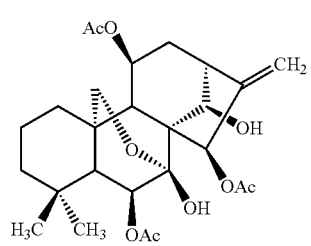

III or a pharmaceutically or physiologically acceptable salt, solvate, or hydrate thereof, wherein Ac is acetyl.

In some embodiments, the compound is rubescensin O-1.

In another aspect, the present invention provides compounds having formula IV as described below:

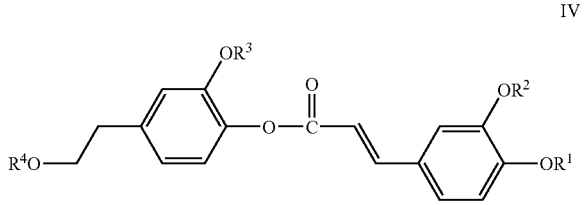

IV or a pharmaceutically or physiologically acceptable salt, solvate, or hydrate thereof, wherein $R^1$, $R^2$, $R^3$ and $R^4$ are each independently hydrogen, $(C_1$-$C_6)$alkyl, $(C_1$-$C_{12})$acyl, a saccharide, an acetylated saccharide, a monosaccharide, an acetylated monosaccharide, a disaccharide or an acetylated disaccharide.

In some embodiments, the present invention provides compounds having formula V as described below:

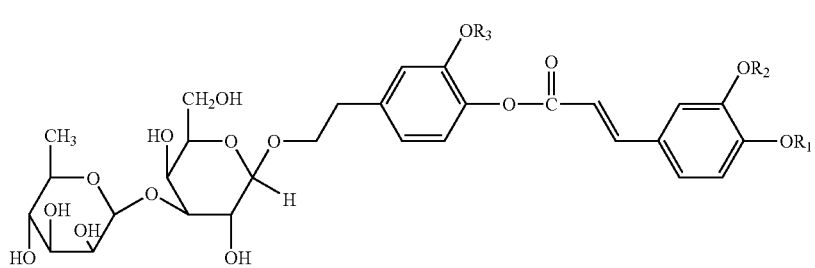

V or a pharmaceutically or physiologically acceptable salt, solvate, or hydrate thereof, wherein $R^1$, $R^2$ and $R^3$ are as defined in formula IV.

In some embodiments, the present invention provides a compound having the following structure:

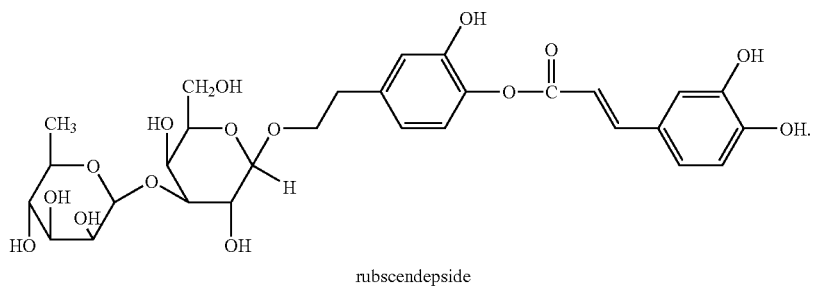

rubscendepside

The present invention also provides compositions comprising a plurality of diterpenoid and/or depside compounds of the invention. In general, the composition is not a natural source of such compounds, such as anatomical parts of the *Rabdosia rubescens* plant. In one aspect, a composition of the invention comprises a mixture of diterpenoids, including one or more of the compounds of formula I, II and/or formula III, or pharmaceutically acceptable salts, solvates or hydrates thereof, wherein (i) the concentration of a diterpenoid in the composition is different from that in a natural source of the diterpenoid; and/or (ii) that the ratio of the concentration of one diterpenoid in the composition to that of another diterpenoid in the composition is different from that in a natural source of the diterpenoid compounds.

In another aspect, a composition of the invention comprises depsides, including one or more of the compounds of formula IV and/or formula V, or pharmaceutically acceptable salts, solvates or hydrates thereof, wherein (i) the concentration of a depside in the composition is different from that in a natural source of the despside; and/or (ii) that the ratio of the concentration of one depside in the composition to that of another depside in the composition is different from that in a natural source of the depside compounds.

Such a composition can be prepared, for example, by processing a natural source of *Rabdosia rubescens* such that at least one particular diterpenoid or depside of the invention has been selectively removed, retained, or enriched. Alternatively, one or more purified diterpenoids or depsides can be used to make such compositions. Such a composition can also be prepared, for example, by adding an amount of at least one diterpenoid or depside of the invention to a natural source or processed form of a natural source of the diterpenoid or depside of the invention.

In one embodiment, the invention provides a composition prepared by extracting a natural source, such as a biomass of *Rabdosia rubescens*, with a plurality of organic solvents, contacting the extractant with a synthetic adsorption resin, and eluting the resin with a plurality of organic solvents, and collecting the fractions which comprise diterpenoids and/or depsides of the invention.

In various embodiments, a composition of the invention can comprise compounds having the formula I, II, III, IV and/or formula V, wherein the concentration of one or more of the compounds having the formula I, II, III, IV and/or formula V, is increased or decreased relative to that in a natural source of the compounds.

In yet another aspect, the present invention also provides nutraceutical compositions comprising one or more diterpenoid and/or depside compounds or compositions of the invention. In yet another aspect, the present invention also provides cosmetic compositions comprising one or more diterpenoid and/or depside compounds or compositions of the invention. In one embodiment, the nutraceutical compositions and cosmetic compositions of the invention are prepared from natural sources.

The nutraceutical compositions include, but are not limited to food additives, dietary supplements, and food compositions that can comprise one or more diterpenoid and/or depside compounds having the formula I, II, III, IV and/or formula V, or pharmaceutically acceptable salts, solvates or hydrates thereof, including but not limited to rabdoternin A, rubescensin M, rubescensin J, rabdoternin B, and rabdoternin C, rubescendepside as described in Section 6, or pharmaceutically acceptable salts, solvates or hydrates thereof. In certain embodiments, the ratio of certain diterpenoid and/or depside in such compositions is different from that of a natural source.

In another embodiment, the present invention also provides pharmaceutical compositions comprising one or more diterpenoid and/or depside compounds of the invention, or a pharmaceutically acceptable salt, solvate, or hydrate thereof. The present invention also provides pharmaceutical compositions comprising one or more compounds of the invention, or a pharmaceutically acceptable salt, solvate, or hydrate thereof, and one or more prophylactic or therapeutic agents in addition to the diterpenoid and/or depside compounds of the compositions. In certain embodiments, the pharmaceutical composition comprises an effective amount of one or more compounds of the invention and a pharmaceutically acceptable carrier, diluent, vehicle or excipient. In some embodiments, the pharmaceutical composition is suitable for parenteral, transdermal, mucosal, nasal, buccal, rectal, sublingual or oral administration to a subject.

In another aspect, the present invention provides methods for preventing, treating, managing, or ameliorating a proliferative disorder, e.g., a cancer, or symptom thereof in a subject in need thereof, preferably a human. In certain embodiments, the methods comprise administering a prophylactically or therapeutically effective amount of a compound of the invention or composition thereof to the subject thereby preventing, treating, managing, or ameliorating the disorder. In certain embodiments, the methods provide a beneficial result by managing symptoms of a disorder, or lessening discomfort associated with a symptom or disorder, e.g., pain. In some embodiments, the proliferative disorder prevented, treated, managed, or ameliorated is a breast cancer, colon cancer, esophageal cancer, liver cancer, lung cancer, prostate cancer, pancreatic cancer, ovarian cancer, skin melanoma, or symptom thereof.

In yet another aspect, the invention provides methods for the prevention, treatment, management, or amelioration of inflammatory disorders, or one or more symptoms thereof, said methods comprising administering to a subject in need thereof a prophylactically or therapeutically effective amount of one or more compounds of the invention. The methods are useful for relieving a symptom of inflammation in a subject, such as but not limited to redness, swelling, edema, excess warmth, allergic reactions; or lessening the discomfort associated with a symptom of inflammation.

In yet another aspect, the invention provides methods for the prevention, treatment, management, or amelioration of an infectious disease, or one or more symptoms thereof, said methods comprising administering to a subject in need thereof a prophylactically or therapeutically effective amount of one or more compounds of the invention.

Administration of the compounds and compositions of the invention can, for example, be via one or more of the pharmaceutical, nutraceutical compositions or cosmetic compositions of the invention. The present invention also provides combination therapies and protocols.

In certain embodiments, the invention provides methods for the prevention or treatment of a cancer or symptom thereof comprising administering an effective amount of rubescensin J or rubscendepside to prevent or treat the cancer or symptom thereof. In some embodiments, the invention provides methods for the prevention or treatment of a cancer or symptom thereof comprising administering an effective amount of a compound selected from the group consisting of rubescensin M, rabdoternin A, rabdoternin B or rabdoternin C, thereby preventing or treating the cancer or symptom thereof. In one aspect, the invention provides methods for inhibiting tumor growth. In some embodiments, the methods comprise administering a composition comprising a compound selected from the group consisting of rubescensin J, rebescensin O-1, rubscendepside, rubescensin M, rabdoternin A, rabdoternin B or rabdoternin C.

In another aspect, the present invention provides articles of manufacture comprising, in one or more containers, a compound, composition, pharmaceutical composition, dietary supplement, food additive, or food composition of the invention.

3.1 Terminology and Abbreviations

As used herein, "a" or "an" means at least one, unless clearly indicated otherwise. The term "about," unless otherwise indicated, refers to a value that is no more than 10% above or below the value being modified by the term. For example, the term "about 5% (w/w)" means a range of from 4.5% (w/w) to 5.5% (w/w).

As used herein, unless indicated otherwise, the terms "compound" and "compound of the invention."

As used herein, unless indicated otherwise, the terms "composition" and "composition of the invention," are used interchangeably. Unless stated otherwise, the terms are meant to encompass, and are not limited to, pharamceutical compositions, nutraceutical compositions, and cosmetic compositions.

It is contemplated that, where the compound(s) of the invention occur in a natural source, the terms "composition" and "composition of the invention" are not intended to include a natural source of the compound(s) but can, in certain embodiments of the invention, encompass a physically and/or chemically modified form of the natural source. For example, if the compound(s) can be obtained from a plant, the terms are not intended to encompass the plant or an anatomical part of the plant, however, a powder or a solvent extract of the plant or plant part(s) can be a composition of the invention.

As used herein, the term "natural source" refers to a material that occurs in the natural environment, and may comprise one or more biological entities. For example, a natural source can be a plant, an animal, an anatomical part of a plant or animal, a microorganism, a mixture of different plants, animals, and/or microorganisms, or an environmental sample. It is not necessary that the biological entities present in a natural source be classified or characterized. The term also refers to compositions which have been prepared directly from that which occurs in the natural environment by a process that does not selectively remove or retain one or more specific compounds relative to the other different compounds.

The following abbreviations are used herein and have the indicated definitions: Ac is acetyl, AP-1 is activator protein-1, COSY is homonuclear correlated Overhauser spectroscopy, DMSO is dimethylsulfoxide, DPPH is 1,1-diphenyl-2-picryl hydroxyl, DEPT is distortionless enhancement by polarization transfer spectroscopy, EIMS is electron ionization mass spectroscopy, Et is ethyl, FT is Fourier transform, GC is gas chromatography, gCOSY is gradient-selected COSY, HPLC is high performance liquid chromatography, HMBC is heteronuclear multiple bond correlation, HMQC is heteronuclear multiple quantum coherence, HRFAB is high resolution fast atomic bombardment, IR is infrared spectroscopy, NMR is nuclear magnetic resonance spectroscopy, NOESY is nuclear Overhauser effect spectroscopy, LC is liquid chromatography, Me is methyl, MS is mass spectroscopy, MTS is 3-(4,3-dimethylthiazol-2-yl)-5-(3-carboxymethoxyphenyl)-2-(4-sulfophenyl)-2H-tetrazolium, PTLC is preparative thin-layer chromatography, ROESY is rotating frame Overhauser enhancement spectroscropy, TLC is thin-layer chromatography, TMS is trimethyl silyl, TOCSY is total Overhauser correlated spectroscopy, and UV is ultraviolet.

4. BRIEF DESCRIPTION OF THE DRAWINGS

FIG. 1 provides general schematic of the synthesis of the ent-kaurene backbone for diterpenoid compounds.

FIGS. 2-24 provide histograms to show the effect of various bioactive compounds at different concentrations on colony formation of various neoplastic or tumor cells.

Figure 2:
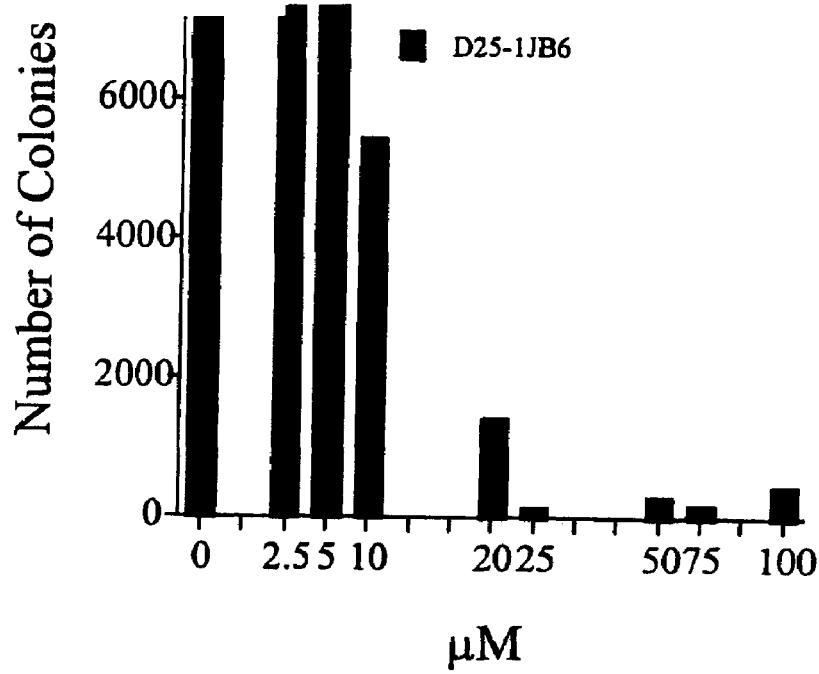

FIG. 2. Effect of rubscendepside on neoplastic transformation in JB6 cells.

Figure 3:
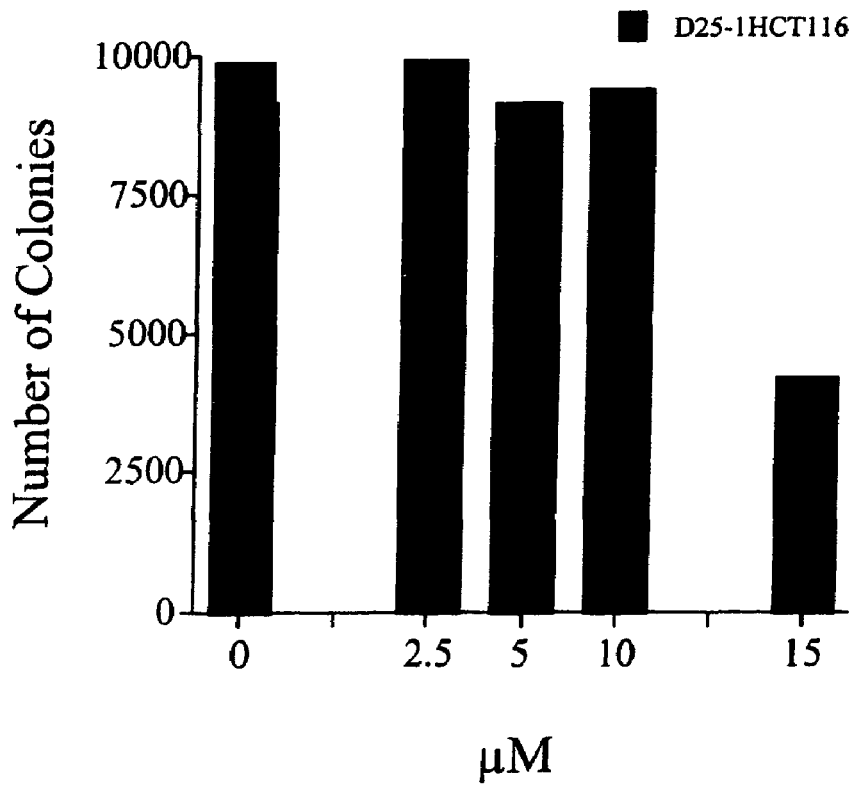

FIG. 3. Effect of rubscendepside on HCT116 expression of phenotype.

Figure 4:
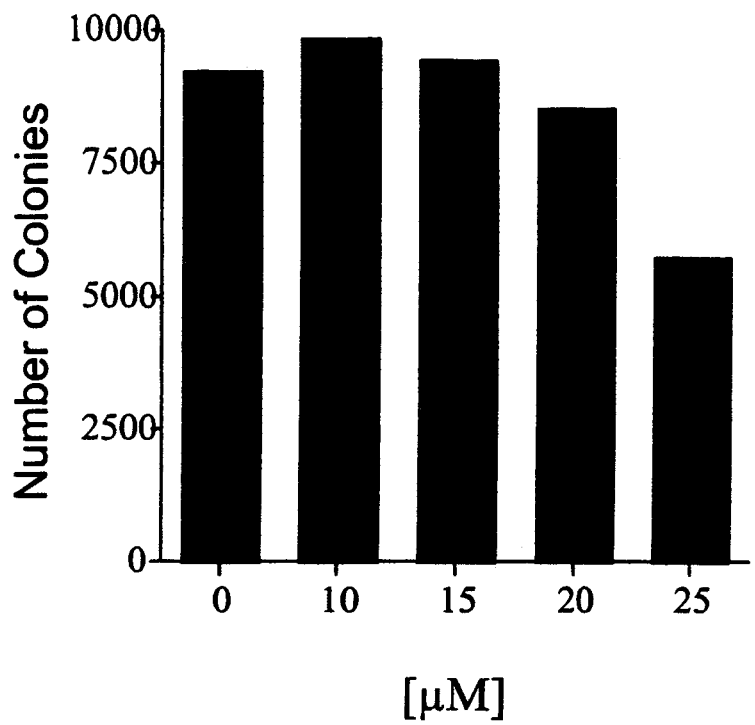

FIG. 4. Effect of rubscendepside on HT460 expression of phenotype.

Figure 5:
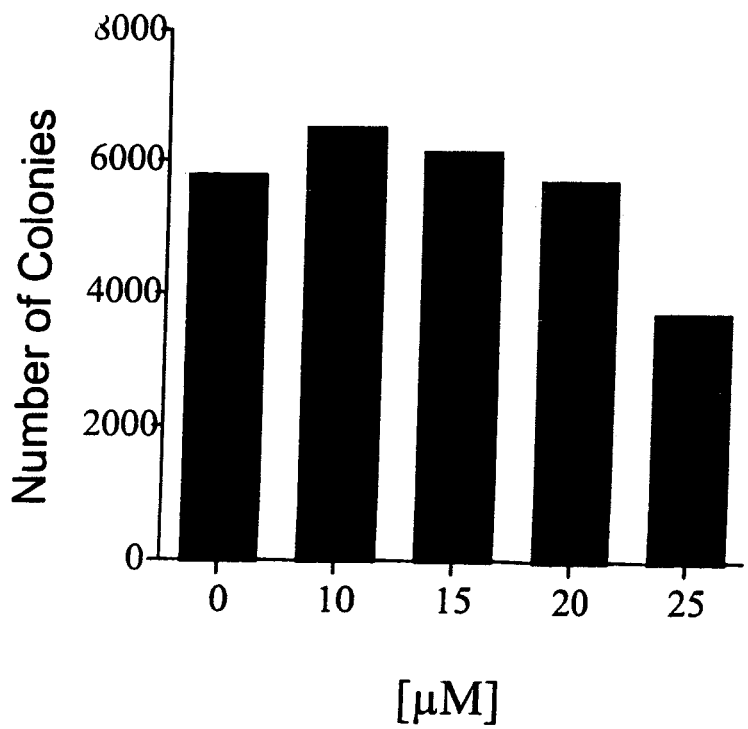

FIG. 5. Effect of rubscendepside on SK-MEL 28 expression of phenotype.

Figure 6:
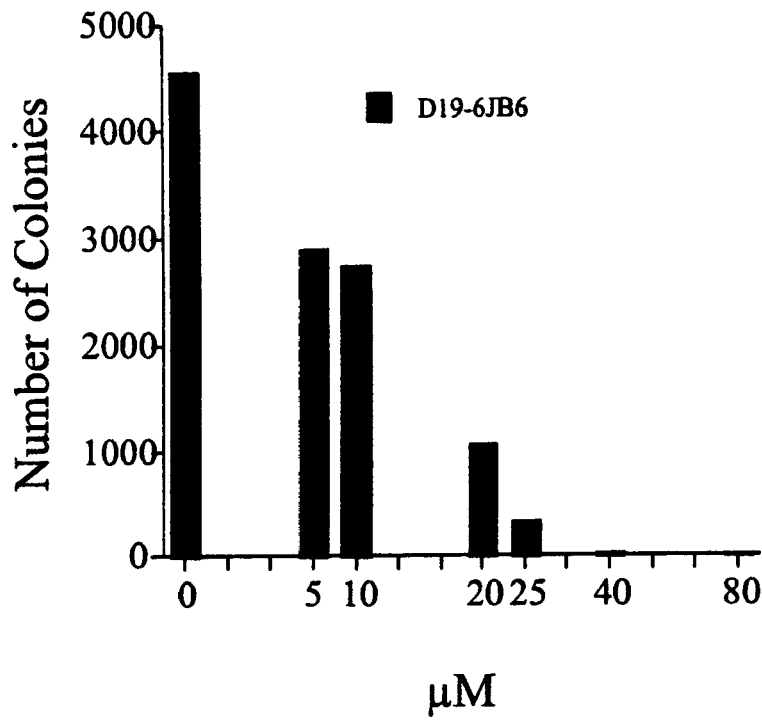

FIG. 6. Effect of rubescensin J on neoplastic transformation in JB6 cells.

Figure 7:
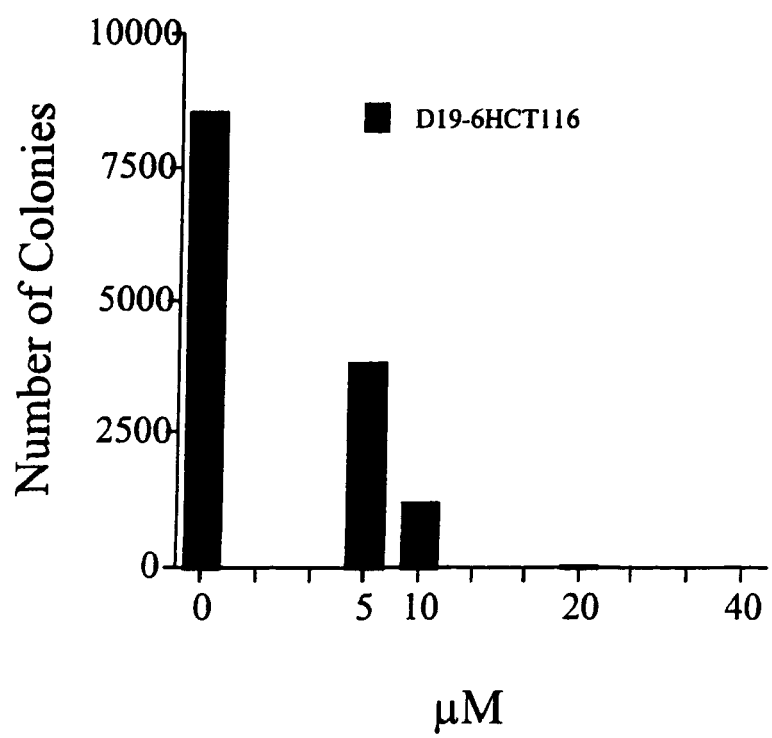

FIG. 7. Effect of rubescensin J on HCT116 expression of phenotype.

Figure 8:
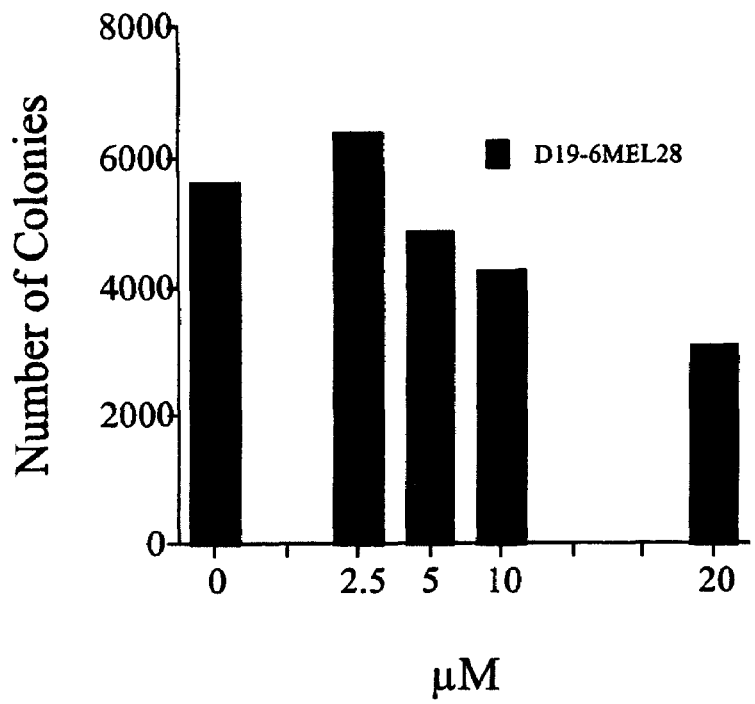

FIG. 8. Effect of rubescensin J on SK-MEL 28 expression of phenotype.

Figure 9:
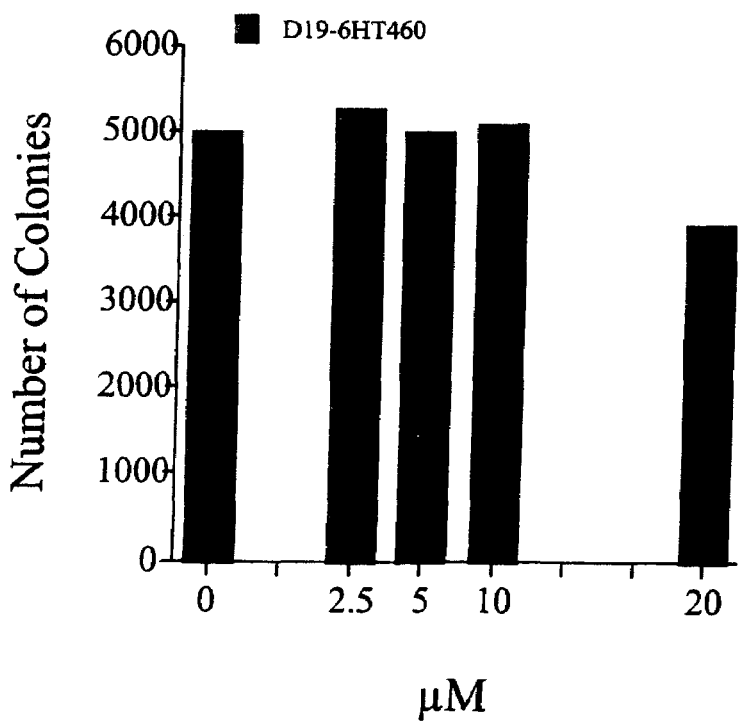

FIG. 9. Effect of rubescensin J on HT460 expression of phenotype.

Figure 10:
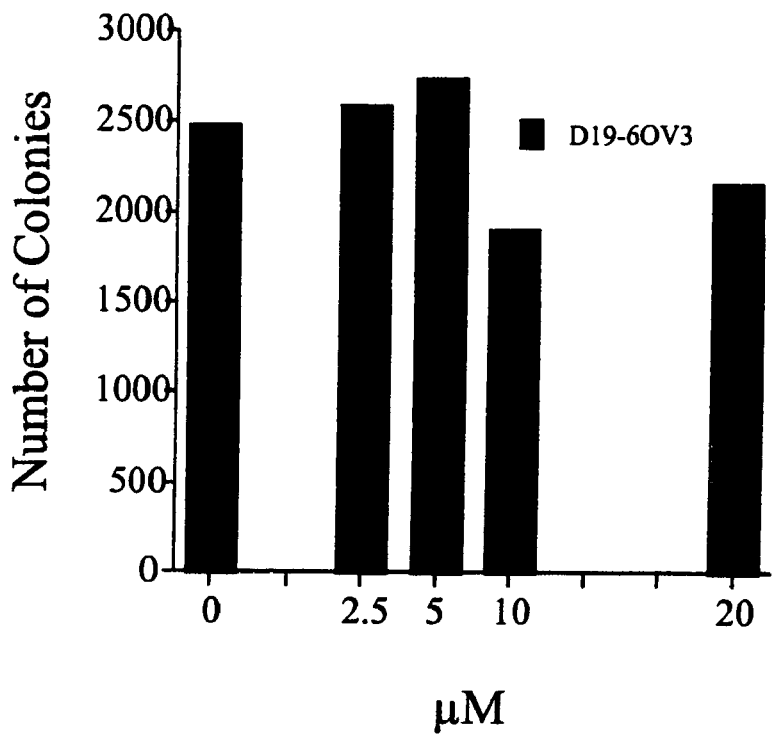

FIG. 10. Effect of rubescensin J on SK-OV-3 expression of phenotype.

Figure 11:
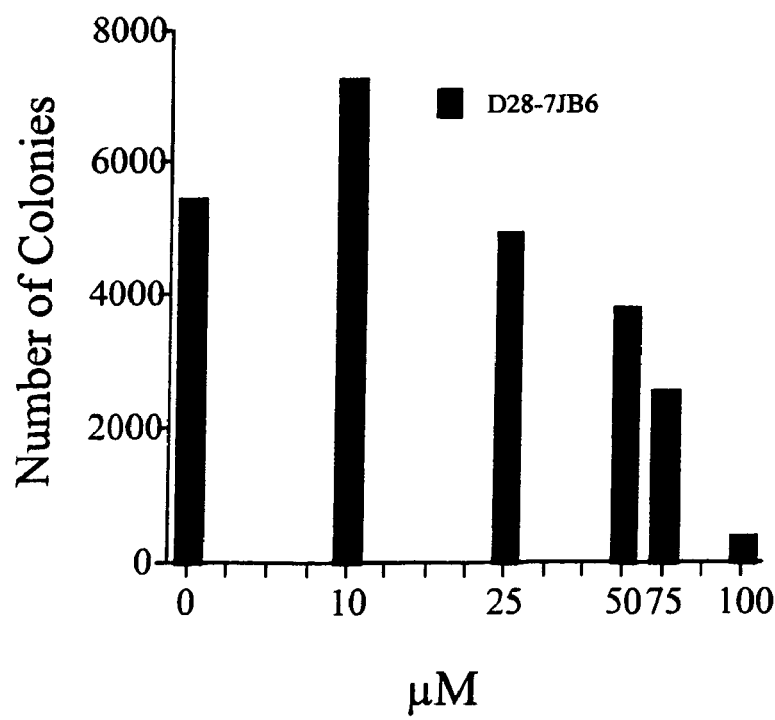

FIG. 11. Effect of rubescensin M on neoplastic transformation in JB6 cells.

Figure 12:
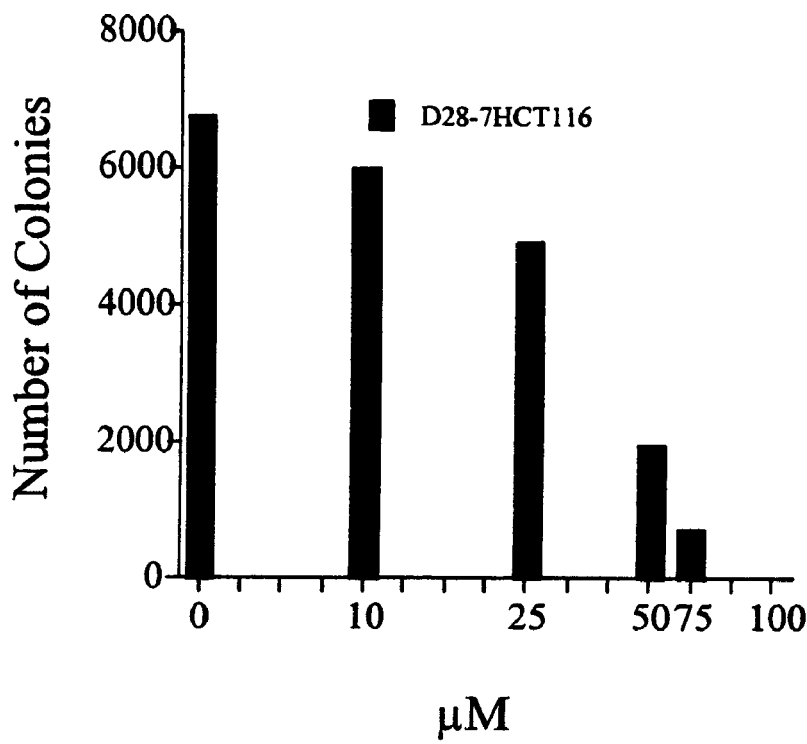

FIG. 12. Effect of rubescensin M on HCT116 expression of phenotype.

Figure 13:
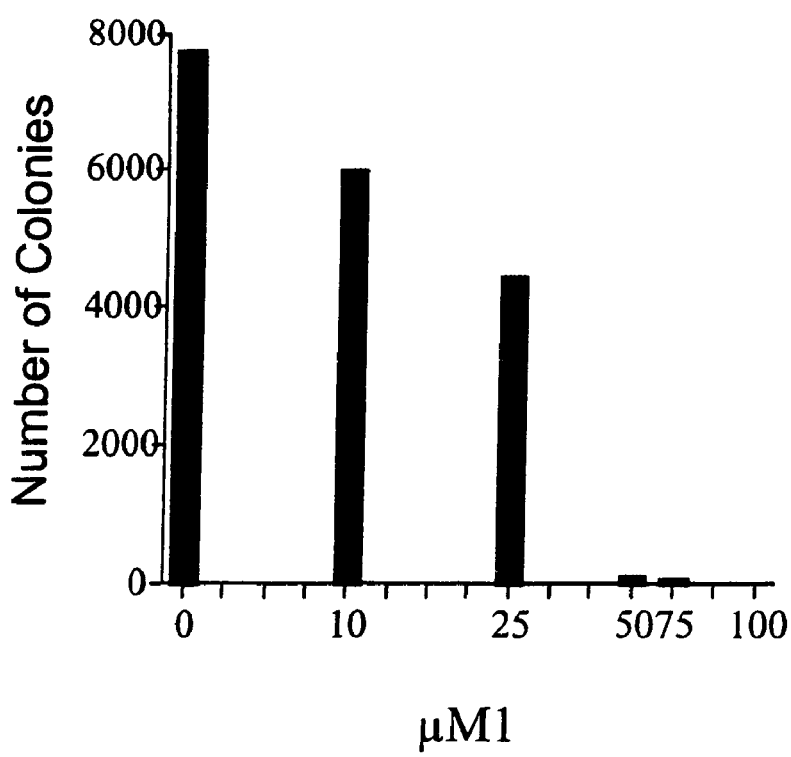

FIG. 13. Effect of rubescensin M on SK-MEL 28 expression of phenotype.

Figure 14:
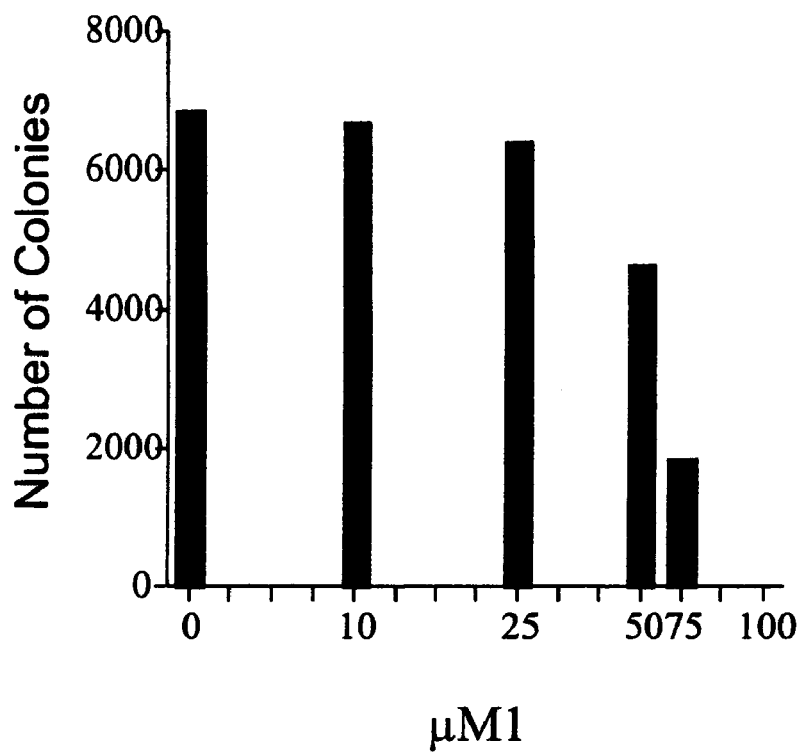

FIG. 14. Effect of rubescensin M on HT460 expression of phenotype.

Figure 15:
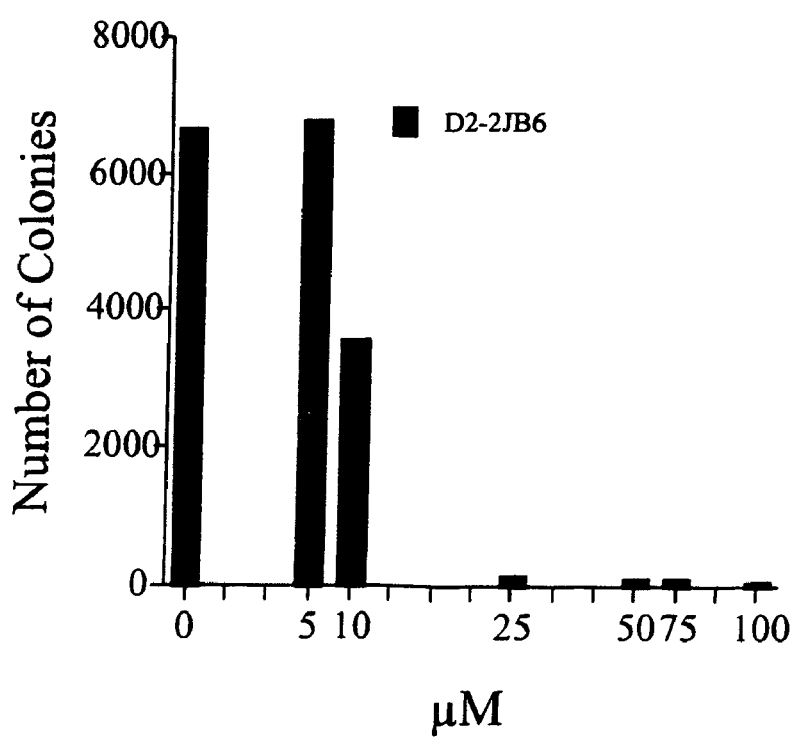

FIG. 15. Effect of rabdoternin A on neoplastic transformation in JB6 cells.

Figure 16:
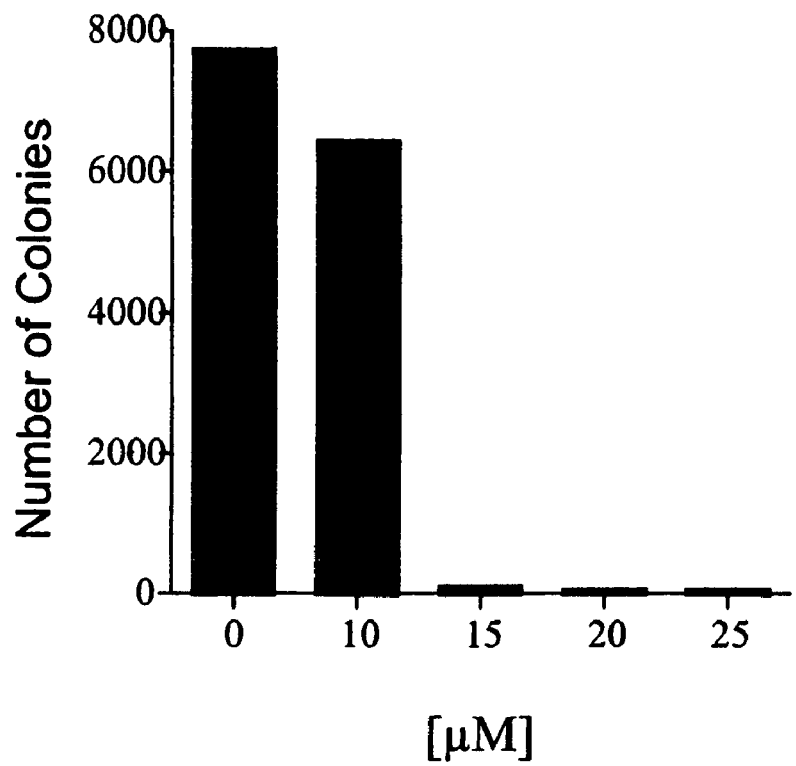

FIG. 16. Effect of rabdoternin A on SK-MEL 28 expression of phenotype.

Figure 17:
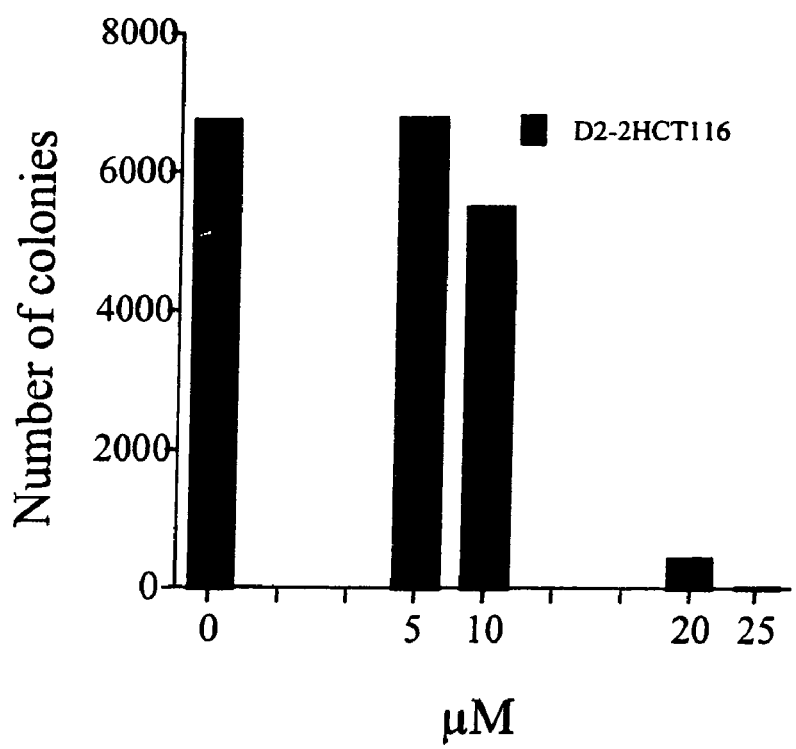

FIG. 17. Effect of rabdoternin A on HCT116 expression of phenotype.

Figure 18:
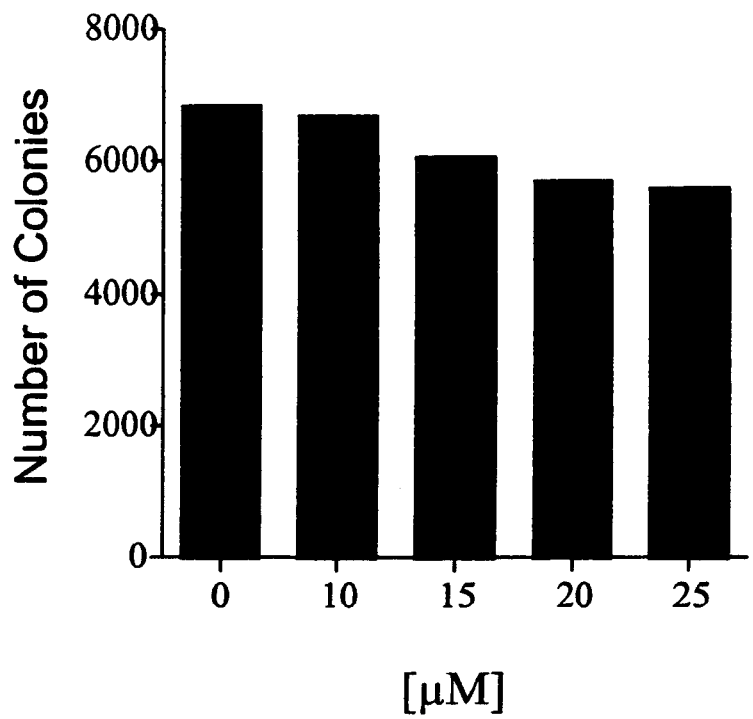

FIG. 18. Effect of rabdoternin A on HT460 expression of phenotype.

Figure 19:
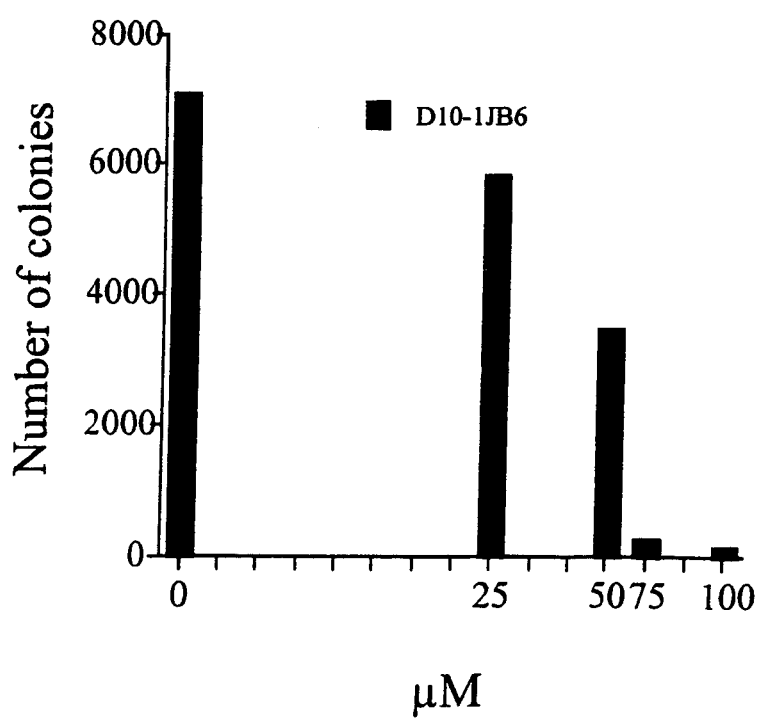

FIG. 19. Effect of rabdoternin B on neoplastic transformation in JB6 cells.

Figure 20:
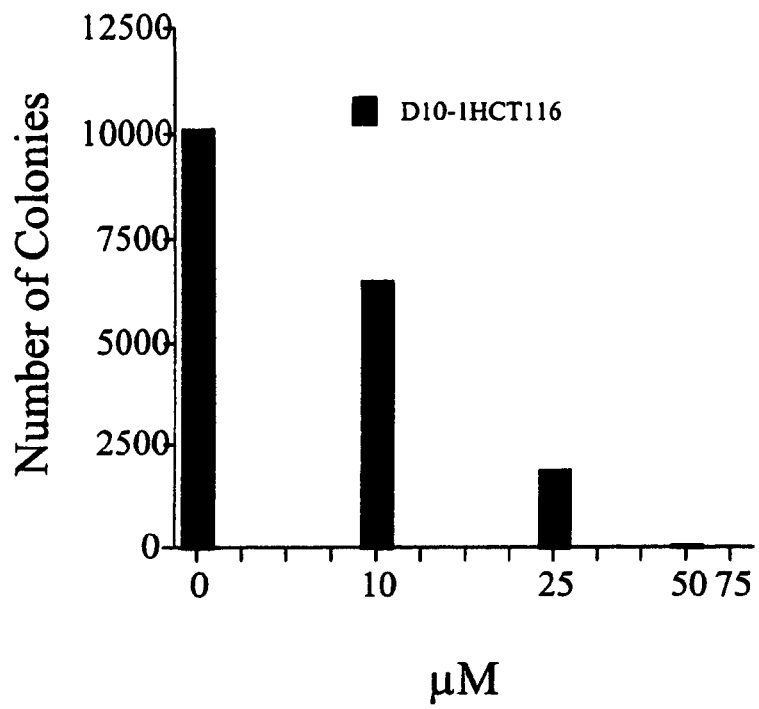

FIG. 20. Effect of rabdoternin B on HCT116 expression of phenotype.

Figure 21:
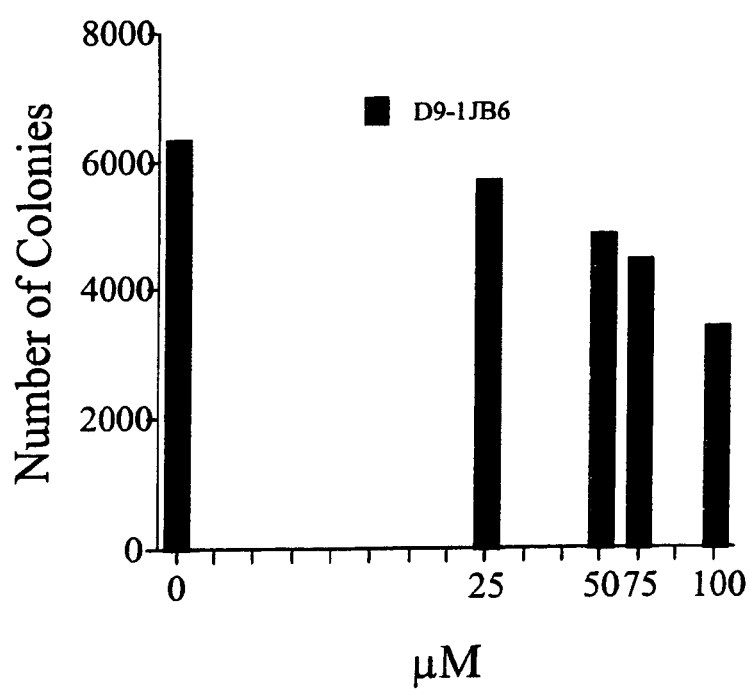

FIG. 21. Effect of rabdoternin C on neoplastic transformation in JB6 cells.

Figure 22:
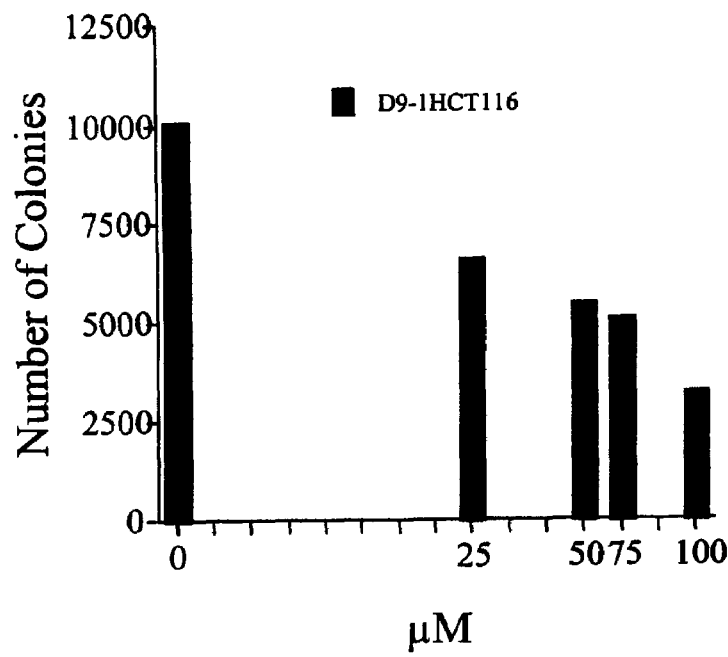

FIG. 22. Effect of rabdoternin C on HCT116 expression of phenotype.

Figure 23:
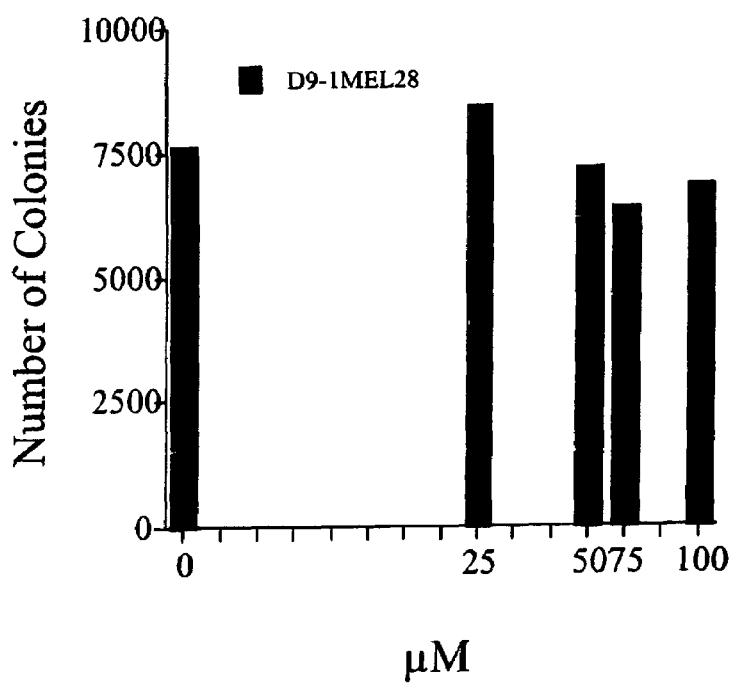

FIG. 23. Effect of rabdoternin C on SK-MEL 28 expression of phenotype.

Figure 24:
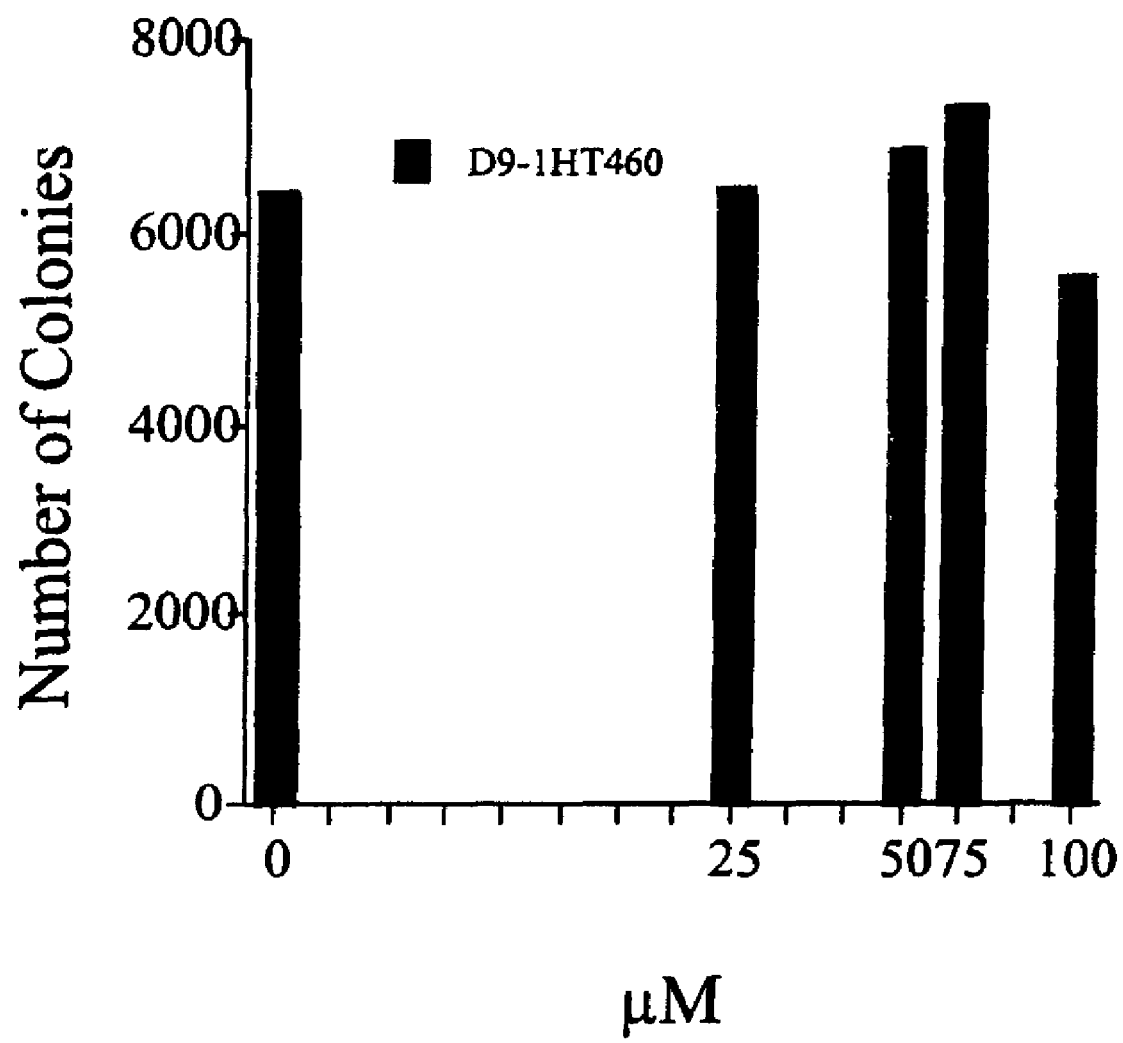

FIG. 24. Effect of rabdoternin C on HT460 expression of phenotype.

Figure 25:
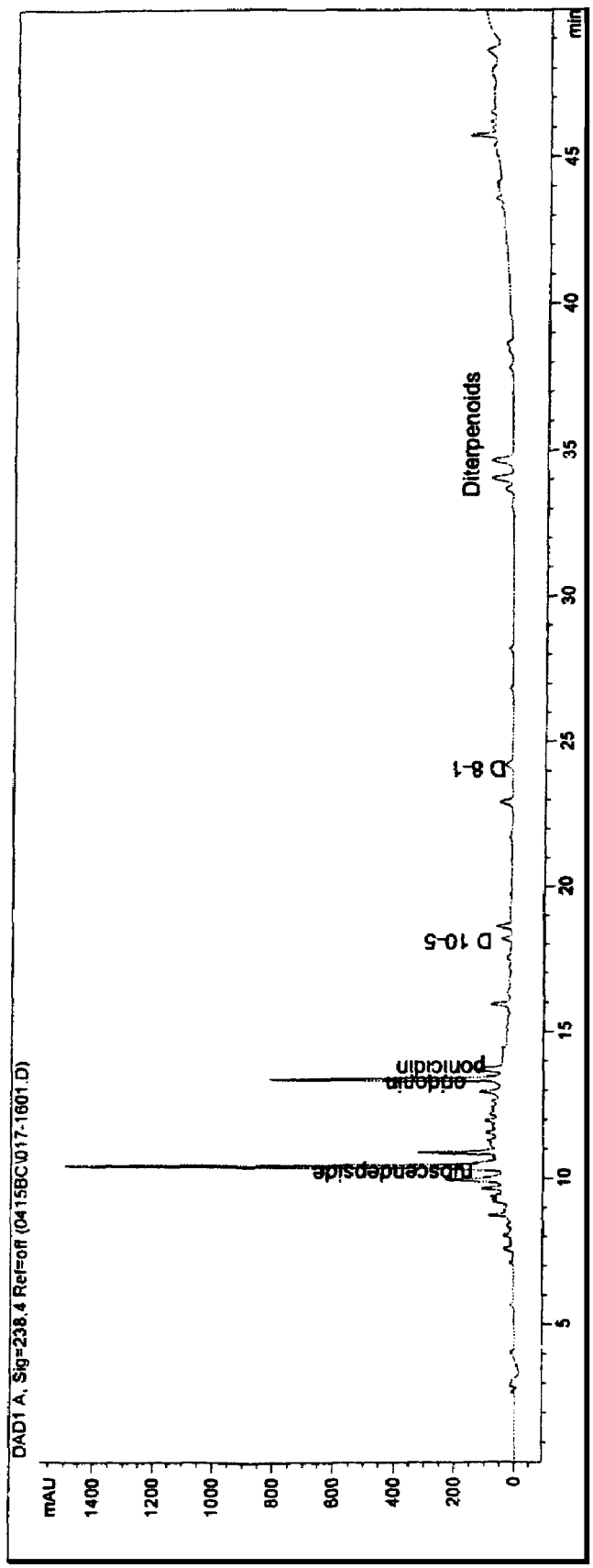

FIG. 25. A chromatogram for a composition enriched for the compounds of the invention analyzed by high performance liquid chromatography (HPLC).

Figure 26A:
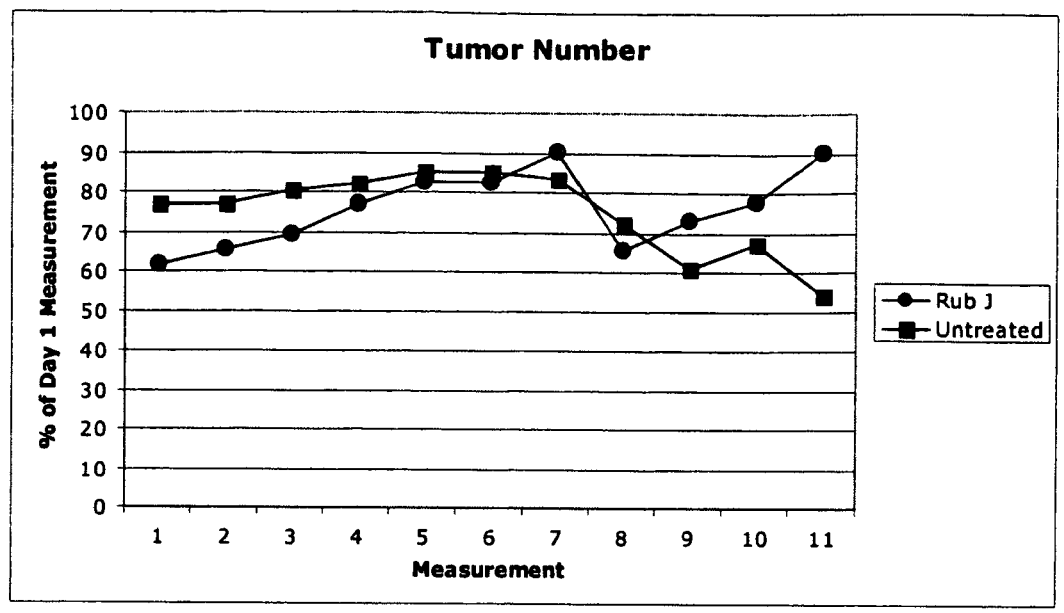
Figure 26B:
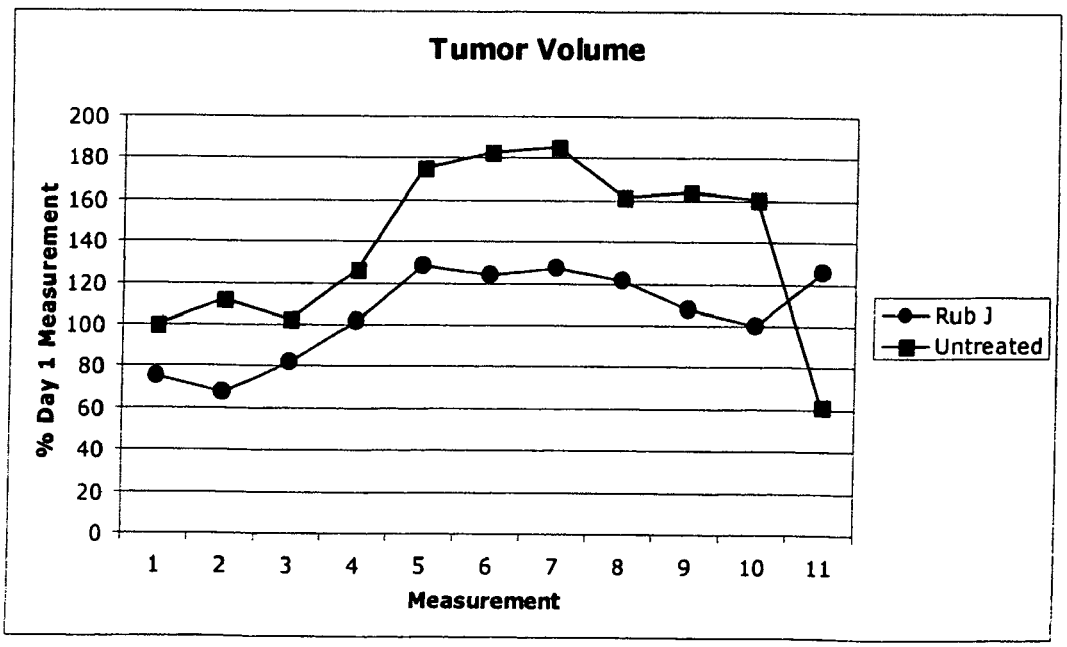

FIGS. 26A and 26B. Effects of rubescensin J on skin cancer induced by UVA exposure in hairless mice.

5. DETAILED DESCRIPTION OF THE INVENTION

The present invention relates to one or more biologically active compound(s) identified in *Rabdosia rubescens*, and uses thereof. For clarity of disclosure, and not by way of limitation, a detailed description of the invention is divided into the subsections which follow.

The structures of the compounds and the methods of making the compounds and compositions of the invention are described in Sections 5.1 and 5.2, respectively. The compositions of the invention comprising one or more biologically active compound(s) of the invention, including but not limited to nutraceutical compositions, pharmaceutical compositions and cosmetic compositions, which are described in details in Sections 5.3 to 5.6. Exemplary methods for using the compounds and compositions of the invention are described in Sections 5.7, 5.8, 5.10, and subsections thereof.

5.1 The Compounds of the Invention

When describing the compounds of the invention, the following terms have the following meanings unless otherwise indicated.

The term "acyl" refers to an alkyl with a carbonyl substituent.

The term "alkyl" means, unless otherwise stated, a straight or branched chain, or cyclic hydrocarbon radical, or combination thereof, saturated or non-saturated, having the number of carbon atoms designated (i.e., $C_1$-$C_6$ means one to six carbons). "Alkyl" is exemplified by groups such as methyl, ethyl, propyl, isopropyl, butyl, isobutyl, sec-butyl, tert-butyl, hexyl, cyclohexyl, (cyclohexyl)methyl, octyl, decyl, dodecyl and the like.

"Alkylcarboxy" is used herein to refer to the COOR group, where R is alkyl as defined above.

"Solvate" refers to a compound of the present invention that further includes a stoichiometric or non-stoichiometric amount of solvent bound by non-covalent intermolecular forces. Where the solvent is water, the solvate is a hydrate.

In one aspect, the present invention encompasses compounds having the formula I:

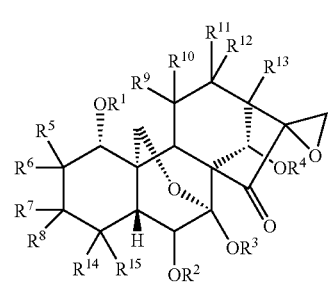

I or a pharmaceutically acceptable salt, solvate, or hydrate thereof, wherein $R^1$-$R^{15}$ are defined below.

$R^1$, $R^2$, $R^3$ and $R^4$ are each independently hydrogen, ($C_1$-$C_6$)alkyl, or ($C_1$-$C_{12}$)acyl. In certain embodiments, $R^1$, $R^2$, $R^3$ and $R^4$ are each independently selected from the group consisting of hydrogen, methyl, ethyl, acetyl, and propionyl. In preferable embodiments, $R^1$, $R^2$, $R^3$ and $R^4$ are hydrogen.

$R^5$, $R^6$, $R^7$, $R^8$, $R^9$, $R^{10}$, $R^{11}$, $R^{12}$, and $R^{13}$ are each independently hydrogen, hydroxyl, $(C_1-C_6)$alkyl, or $(C_1-C_6)$alkylcarboxyl.

In certain embodiments, $R^5$-$R^{13}$ are each independently hydrogen or $(C_1-C_6)$alkyl.

In some embodiments, $R^5$-$R^{13}$ are each independently selected from the group consisting of hydrogen, methyl, and ethyl.

In some embodiments, at least four of $R^5$-$R^{13}$ are hydrogen.

In preferable embodiments, $R^5$-$R^{13}$ are hydrogen.

In certain embodiments, $R^1$-$R^{13}$ are hydrogen.

$R^{14}$ and $R^{15}$ are each independently hydrogen or $(C_1-C_6)$alkyl. In certain embodiments, $R^{14}$ and $R^{15}$ are methyl. In some embodiments, $R^{14}$ and $R^{15}$ are hydrogen.

In certain embodiments, the present invention provides an isolated compound having formula I as defined above.

In certain embodiments, the present invention provides a compound having formula II:

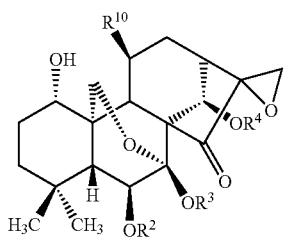

II or a pharmaceutically acceptable salt, solvate or hydrate thereof, wherein $R^2$, $R^3$, $R^4$ and $R^{10}$ are as defined above in formula I.

In some embodiments, the compound is rubescensin J or a pharmaceutically acceptable salt, solvate or hydrate thereof.

In some embodiments, the present invention provides an isolated compound having formula II as defined above.

Illustrative examples of those compounds having formula II are set forth below:

TABLE 1

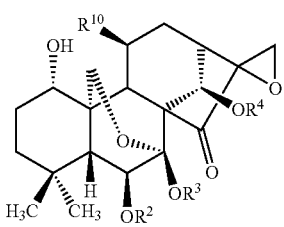

II

| $R^2$ | $R^3$ | $R^4$ | $R^{10}$ |
|---|---|---|---|
| H | H | H | H |
| Ac | Ac | Ac | H |
| Ac | H | H | H |
| Ac | Ac | H | H |
| Ac | H | Ac | H |
| H | Ac | H | H |
| Me | H | H | H |
| H | Me | H | H |

TABLE 1-continued

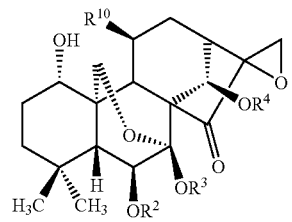

II

| $R^2$ | $R^3$ | $R^4$ | $R^{10}$ |
|---|---|---|---|
| Me | Me | H | H |
| Et | H | H | H |
| H | Et | H | H |
| Et | Et | H | H |
| propionyl | H | H | H |
| H | Propionyl | H | H |
| Me | H | Ac | H |
| H | H | H | OH |
| Ac | Ac | Ac | OH |
| Ac | H | H | OH |
| Ac | Ac | H | OH |
| Ac | H | Ac | OH |
| H | Ac | H | OH |
| Me | H | H | OH |
| H | Me | H | OH |
| Me | Me | H | OH |
| Et | H | H | OH |
| H | Et | H | OH |
| Et | Et | H | OH |
| propionyl | H | H | OH |
| H | Propionyl | H | OH |
| Me | H | Ac | OH |
| H | H | H | OAc |
| Ac | Ac | Ac | OAc |
| Ac | H | H | OAc |
| Ac | Ac | H | OAc |
| Ac | H | Ac | OAc |
| H | Ac | H | OAc |
| Me | H | H | OAc |
| H | Me | H | OAc |
| Me | Me | H | OAc |
| Et | H | H | OAc |
| H | Et | H | OAc |
| Et | Et | H | OAc |
| propionyl | H | H | OAc |
| H | Propionyl | H | OAc |
| Me | H | Ac | OAc |
| H | H | H | Me |
| Ac | Ac | Ac | Me |
| Ac | H | H | Me |
| Ac | Ac | H | Me |
| Ac | H | Ac | Me |
| H | Ac | H | Me |
| Me | H | H | Me |
| H | Me | H | Me |
| Me | Me | H | Me |
| Et | H | H | Me |
| H | Et | H | Me |
| Et | Et | H | Me |
| propionyl | H | H | Me |
| H | propionyl | H | Me |
| Me | H | Ac | Me |
| H | H | H | Et |
| Ac | Ac | Ac | Et |
| Ac | H | H | Et |
| Ac | Ac | H | Et |
| Ac | H | Ac | Et |
| H | Ac | H | Et |
| Me | H | H | Et |
| H | Me | H | Et |
| Me | Me | H | Et |
| Et | H | H | Et |
| H | Et | H | Et |
| Et | Et | H | Et |

TABLE 1-continued

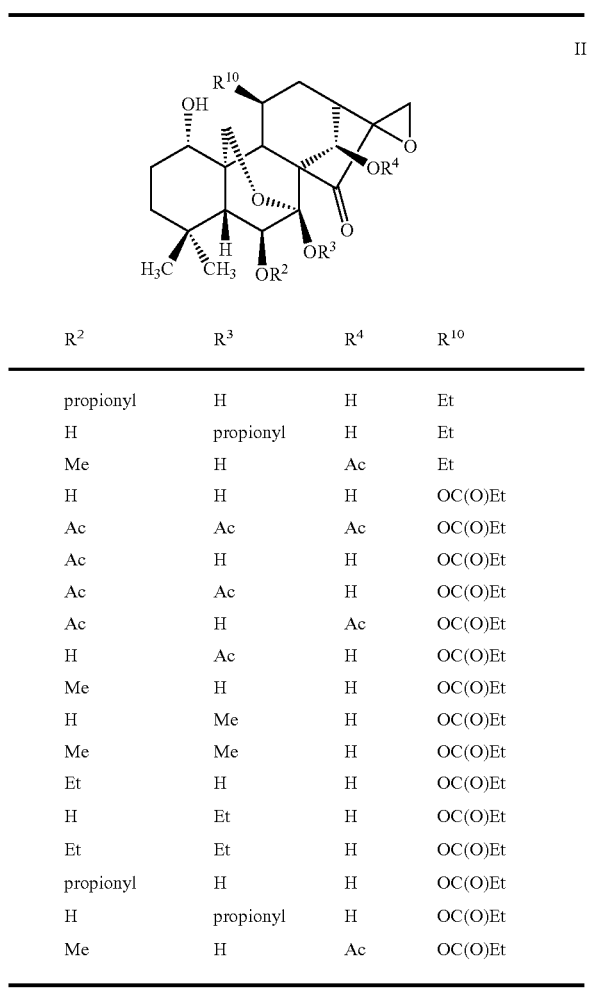

| R² | R³ | R⁴ | R¹⁰ |
| --- | --- | --- | --- |
| propionyl | H | H | Et |
| H | propionyl | H | Et |
| Me | H | Ac | Et |
| H | H | H | OC(O)Et |
| Ac | Ac | Ac | OC(O)Et |
| Ac | H | H | OC(O)Et |
| Ac | Ac | H | OC(O)Et |
| Ac | H | Ac | OC(O)Et |
| H | Ac | H | OC(O)Et |
| Me | H | H | OC(O)Et |
| H | Me | H | OC(O)Et |
| Me | Me | H | OC(O)Et |
| Et | H | H | OC(O)Et |
| H | Et | H | OC(O)Et |
| Et | Et | H | OC(O)Et |
| propionyl | H | H | OC(O)Et |
| H | propionyl | H | OC(O)Et |
| Me | H | Ac | OC(O)Et | and pharmaceutically acceptable salts and solvates thereof. Residues not specifically listed in the table above are understood to be hydrogen, unless specified otherwise.

In one aspect, the present invention provides a compound having the formula III:

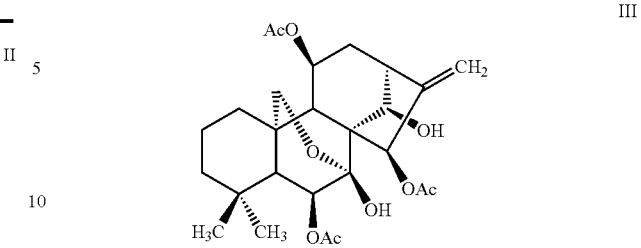

or a pharmaceutically acceptable salt, solvate, or hydrate thereof.

In some embodiments, the compound is rubescensin O-1 or a pharmaceutically acceptable salt, solvate, or hydrate thereof.

In certain embodiments, the present invention provides an isolated compound having formula III as defined above.

In one aspect, the present invention encompasses compounds having formula IV:

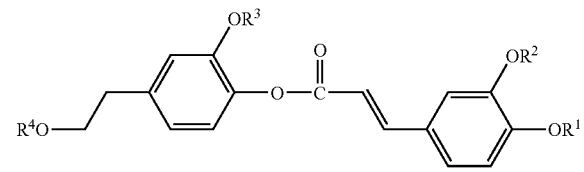

or a pharmaceutically acceptable salt, solvate, or hydrate thereof, wherein $R^1$, $R^2$, $R^3$ and $R^4$ are each independently hydrogen, $(C_1$-$C_6)$alkyl, $(C_1$-$C_{12})$acyl, a monosaccharide, an acetylated monosaccharide, a disaccharide or an acetylated disaccharide.

In certain embodiments of formula IV, $R^1$-$R^4$ are each independently hydrogen, methyl, ethyl, acetyl, propionyl, a monosaccharide or a disaccharide.

In some embodiments, $R^1$-$R^4$ are hydrogen.

In some embodiments, $R^1$-$R^3$ are hydrogen and $R^4$ is a monosaccharide or a disaccharide.

In some embodiments, the compound of formula IV is an (E) alkene diastereomer.

In some embodiments, the compound of formula IV is a (Z) alkene diastereomer.

In certain embodiments, the present invention provides an isolated compound having formula IV as defined above.

In certain embodiments, a compound has the formula V:

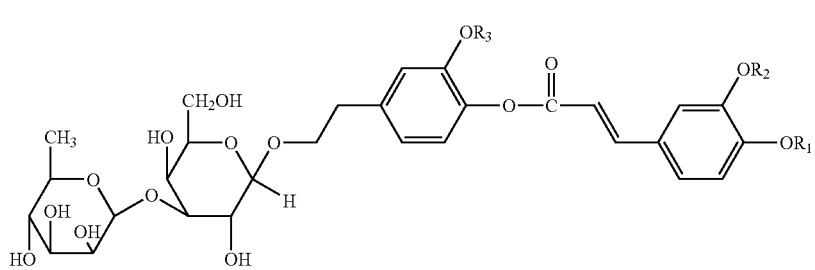

In some embodiments, $R^1$, $R^2$ and $R^3$ are hydrogen, $(C_1$-$C_6)$alkyl or $(C_1$-$C_{12})$acyl.

In some embodiments, the compound is rubescendepside or a pharmaceutically acceptable salt, solvate, or hydrate thereof.

In certain embodiments, the present invention provides an isolated compound having formula V as defined above.

In one aspect, the invention encompasses a compound selected from the group consisting of rubescensin N, rubescensin M, rabdoternin A, rabdoternin B and rabdoternin C.

In certain embodiments, the diterpenoid and depside compounds of the invention are isolated.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn, Ingold and Prelog (INPAC compendium of chemical terminology $2^{nd}$ ed., 1997), or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

In one embodiment, the invention includes the racemic or either the R- or S-enantiomers of all the compounds described herein. The enantiomers may each be provided in a form substantially free of the other enantiomer(s)(e.g., at least 75% free (w/w), at least 90% free (w/w) or at least 99% free (w/w)) or as mixtures (e.g., racemic mixtures).

5.2 Methods for Making the Compounds of the Invention

In one embodiment, the compounds of the invention can be extracted from a natural source. Typically, the natural source or preferred portions thereof, such as the floral parts of a plant, in natural or dried form, may be used directly, or pulverized, ground or comminuted to a fine powder in order to maximize surface contact with the solvent. However, the methods of the present invention can be employed on any known natural source, plant matter or biomass that contains an appreciable amount of the compounds of the invention. *Rabdosia rubescens* is a preferred starting material.

According to an exemplary method of the present invention, the aerial parts of *Rabdosia rubescens* are dried and crushed into a powder. Preferably, the biomass is then contacted with a water miscible solvent sufficient to put the compounds of the invention in the biomass into solution. Solvent extraction can be performed at room temperature or at elevated temperatures, usually at from about 3° C. to about 80° C., with or without ultrasonication. Suitable solvents include, but are not limited to, acetone and ethanol. Methanol or isopropanol may also be used, but are generally less desirable in preparing compositions for human food applications. Other solvent that can be used include but is not limited to carbon tetrachloride, cyclohexane, toluene, dichloromethane, chloroform, diethyl ether, diisopropyl ether, ethyl acetate, butanol, n-propanol, polyethylene glycol, propylene glycol, pyridine, and the like. A mixture of two or more solvents can be used.

The biomass:solvent ratio should be at a minimum about 10 to 30 L of extracting solvent to one kg of biomass. The compounds of the invention in solution and the insoluble impurities can then be separated by any conventional means, such as filtration or centrifugation, concentrated by an evaporator, and dried by vacuum drying or spray drying to produce a crude extract comprising the compounds of the invention.

In one embodiment, the invention provides an extraction composition prepared by extracting a natural source, such as a biomass of *Rabdosia rubescens*, with one or more organic solvents, such as but not limited to hexane and/or n-butanol, which comprises a dry weight of about 2% to 10%, preferably about 5%, of the dried weight of the starting biomass. The composition comprises about 20% to 25% diterpenoids, and about 1% to 10% depsides.

In another embodiment, the invention provides a method for enriching the diterpenoids and depsides of the invention comprising chromatography, including reverse phase liquid chromatography, using a synthetic polymeric resin. Preferred stationary phases for chrmoatography include polymers of vinyl aromatic compounds, for example styrene, that are crosslinked with polyvinylic aromatic hydrocarbons, for example divinyl benzene. These organic polymeric stationary phases are made by processes that yield small, extremely rigid, macroreticular particles. Crosslinked acrylic polymers are also useful as stationary phases for reverse phase liquid chromatography, as are polyvinyl alcohols (alkylated or non-alkylated). Suitable stationary organic phases for RPLC are commercially available. For example, styrenic and acrylic stationary phases are available from Mitsubishi Chemicals under the trade name Diaion™ or Sepabeads™, the Rohm and Haas Company, Philadelphia, Pa., under the trade name Amberlite™. Styreneic stationary phases are also available under the trade name Amberchrom™. from Tossohass, Montgomeryville, Pa. Also preferred are polyamide resins (e.g. nylons), polyester resins, and phenolic resins for the chromatography processes of the present invention.

Many organic solvents are suitable mobile phases, or eluants, for liquid chromatography. Lower alcohols, such as methanol, ethanol and propanol as well as nitriles such as acetonitrile, are suitable as organic eluents. Lower aliphatic ketones such as acetone, methyl ethyl ketone, and diethyl ketone, as well as cyclic ethers such as tetrahydrofuran, can also be used. Dimethyl formamide, dimethyl sulfoxide, and alkyl esters of acetic acid such as ethyl acetate can also be used. Mixtures of such solvents in various proportions can be used when it is desired to elute or wash the column with solvents of varying polarity. Aqueous solvents that are m of water and an alcohol, for example, methanol, ethanol n-propanol iso-propanol n-butanol, and n-and sec-hexanol are particularly useful as mobile phases or eluants for the chromatographic processes of the present invention, which in certain embodiments are carried out using an eluant of variable composition. Thus, an elution volume which is a volume of aqueous solvent applied to the column, can be a gradient eluant having two or more gradient volumes, the composition of which can be the same or different, or the compositon of the gradient eluant can be varied continuously during elution. The composition of the elution volume that is a gradient eluant can vary step-wise, linearly, sigmoidally, exponentially, logarithmically, parabolically, or hypyperbolically during elution. The limits of concentration of gradient eluants are determined by the concentration of polar organic solvent necessary to elute products from the stationary phase and by the requirement that the polar organic solvent be miscible to form a single phase at the required concentration.

In certain embodiments of the present invention the initial alcohol concentration in the elution volume is 10 volume percent (10 vol-%) or less and is increased as separation and purification proceeds. The liquid chromatography systems used to practice the present invention may be either preparative or analytical. Preparative columns have larger loading capacity and are typically larger in size. With regards to the dimensions of the liquid chromatographic column, the loading of the column, the temperature, and flow rate, one skilled in the art will know to vary these parameters based primarily upon practical considerations known in the art. For example, flow rates of the eluent are adjusted according to the column dimensions, the degree of separation desired, the particle size of the stationary phase, and the back pressure in the column. The separation is typically carried out at 20° C. to 30° C. However, a temperature up to about 45° C. can be used. The separation may be carried out at high pressure (500-200 psi) or moderate pressures (100-500 psi) or, preferably, at lower pressures (10-100 psi). Prior to use, the liquid chromatography column can be conditioned by eluting the column with a conditioning volume of a conditioning liquid, preferably an aqueous solvent, more preferably water. The conditioning volume is preferably between about 1 and about 10 column volumes. The extract containing the compounds of interest is applied to the preferably conditioned chromatography column as a solution, a slurry, or a loading concentrate obtained by evaporating an aqueous solvent, preferably alcohol, from an extraction composition containing the compounds of the invention. If the extraction composition to be treated is solid, it may be mixed with a suitable solid carrier, for example treated or untreated silica gel, and the solid mixture placed on top of the solid support. Loading of the column is accomplished by eluting the solution, slurry, or loading concentrate through the column; or, when the product to be treated is admixed with silica gel, by eluting the column with a loading elution volume. Preferably, elution of the solution, slurry, loading concentrate, or loading elution volume is followed by elution with a washing elution volume comprising an aqueous solvent having the same composition as the aqueous solvent of the solution, slurry, or loading concentrate used to load the column stationary phase. The washing elution volume, when one is used, is preferably between about 1 and about 10 column volumes.

In a specific embodiment, the method comprises contacting an extraction composition of a natural source, such as an extract of *Rabdosia rubescens*, in an aqueous solution or in methanol or ethanol, with a synthetic polymeric resin comprising polyamide moieties or styrene-divinylbenzene moieties for a period of time sufficient for the diterpenoids and/or depsides of the invention to adsorb to the polymeric resin, and eluting the resin with one or more solvents, and collecting the fractions which comprise diterpenoids and/or depsides of the invention. Exemplary methods for extracting and enriching diterpenoids and/or depsides compounds of the invention are provided in Sections 6 and 7.

In a specific embodiment, the compounds of the invention can be selectively removed, enriched or retained by applying supercritical fluid extraction technique to a natural source. This technique, which generally utilizes carbon dioxide, is known in the art, especially for preparing food and medicinal substances for human consumption. See, for example, Hamburger et al., Phytochemical Analysis (2004), 15(1), 46-54; Simandi et al., Recents Progres en Genie des Procedes (1999) 13(71), 157-164, the disclosures of which are incorporated herein by reference in their entirety. A co-solvent, such as methanol or ethanol (from 5% to 15%), may also be used in the technique to increase the solubility of polar compounds. Accordingly, in one embodiment, the invention encompasses compositions comprising one or more diterpenoids and/or depsides of the invention that have been obtained via supercritical carbon dioxide extraction from a natural source. Such compositions are produced by a process comprising treating a biomass comprising compounds of the invention, such as an extract of or a aerial part of *Rabdosia rubescens*, with supercritical carbon dioxide for a period of time and at a pressure (from the critical pressure of carbon dioxide, to about 100, 200, 300, 400, 500 bar and up to about 800 bar) and a temperature (from about 30° C., about 40° C., about 50° C., about 60° C., about 70° C., to about 80° C.) that extract the diterpenoids and depsides of the invention, including conditions that selectively extract specific diterpenoids and depsides of the invention; and collecting the extracted compounds.

In another embodiment, the compounds of the invention can be synthesized chemically. The diterpenoid and depside compounds of the invention can be prepared from readily available starting materials using the following exemplary general methods and procedures. An example of a biosynthetic pathway for obtaining the ent-kaurene backbone is presented in FIG. 1. It will be appreciated that where typical or preferred process conditions (e.g., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Third Edition, Wiley, New York, 1999, and references cited therein.

Once synthesized, a compound of the invention can be isolated from chemical precursors or other chemicals using standard purification techniques such as, for example, chromatography (e.g., flash column chromatography and HPLC), recrystallization, and differential solubility.

5.3 The Compositions of the Invention

The present invention provides compositions comprising one or more compound(s) of the invention as described in Section 5.1.

In one embodiment, the invention provides a composition comprising a compound of the invention. In another embodiment, the invention provides a composition comprising an isolated compound of the invention. As used herein, the term "isolated" in the context of a compound of the invention that is chemically synthesized, refers to a compound that is substantially free of chemical precursors. In a specific embodiment, the compound is 60%, 65%, 75%, 80%, 85%, 90%, 95%, or 99% free (by dry weight) of other, different compounds.

In another embodiment, the present invention also provides compositions comprising more than one compound of the invention. For example, a composition of the invention can comprises two, three, four, five, six, seven, eight, nine, or ten or more compounds of the invention. In a specific embodiment, the compounds in the composition are individually purified or purified together.

The compositions of the invention do not encompass a natural source of the compounds of the invention. Examples of a natural source of such compounds include the *Rabdosia rubescens* plant, anatomical parts of the *Rabdosia rubescens* plant, such as the aerial parts, the floral parts, and other closely related *Rabdosia* species and their anatomical parts.

A natural source of the compounds can be a plant or its anatomical part in its natural form, but can also include compositions which have been prepared directly from the plant or its parts by a process that does not selectively remove or retain one or more particular diterpenoid and depside compounds relative to other compounds present in the plant, for example, pulverized *Rabdosia rubescens* plant or its parts.

The term "isolated" when used in the context of a compound of the invention that can be obtained from a natural source, e.g., plants, refers to a compound which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. The phrase "substantially free of natural source materials" refers to preparations of a compound that have been separated from cellular components of the cells from which it is isolated. Thus, a compound that is isolated includes preparations of a compound having less than about 30%, 20%, 10%, 5%, 2%, or 1% (by dry weight) of cellular materials and/or contaminating materials.

In certain embodiments, a composition of the invention comprises diterpenoids, including one or more of the compounds of formula I, II, and/or formula III, or a pharmaceutically acceptable salt, solvate or hydrate thereof, wherein (i) the concentration of a diterpenoid in the composition is different from that of a natural source of the diterpenoid; and/or that (ii) the ratio of the concentration of at least one diterpenoid in the composition to that of another diterpenoid is different from that found in a natural source of the diterpenoid compounds. For example, a two-fold increase or decrease in concentration of one of the diterpenoids can be used to distinguish a composition of the invention from a natural source.

Such a composition can be prepared, for example, by processing a natural source of diterpenoids such that at least one particular diterpenoid has been selectively removed or enriched or retained. Alternatively, one or more purified diterpenoid can be used to make such compositions. Such a composition can also be prepared, for example, by adding an amount of at least one diterpenoid of the invention to a natural source of the diterpenoid compounds.

In certain embodiments, a composition of the invention comprises depsides, including one or more of the compounds of formula IV, and/or formula V, or a pharmaceutically acceptable salt, solvate or hydrate thereof, wherein (i) the concentration of a depside in the composition is different from that of a natural source of the diterpenoid; and/or that (ii) the ratio of the concentration of one depside in the composition to that of another depside is different from that found in a natural source of the depside compounds. For example, a two-fold increase or decrease in concentration of one of the depsides can be used to distinguish a composition of the invention from a natural source.

Such a composition can be prepared, for example, by processing a natural source of depsides such that at least one particular depsides has been selectively removed or enriched or retained. Alternatively, one or more purified depside can be used to make such compositions. Such a composition can also be prepared, for example, by adding an amount of at least one depside of the invention to a natural source or processed natural source of the depside compounds.

In specific embodiments, a composition of the invention can comprise compounds having the formula I, II, III, IV and/or formula V, or a pharmaceutically acceptable salt, solvate or hydrate thereof, wherein (i) the concentration of one or more of the compounds having the formula I is increased or decreased relative to that found in a natural source of the compounds; (ii) the concentration of one or more of the compounds having the formula II is increased or decreased relative to that found in a natural source of the compounds; (iii) the concentration of one or more of the compounds having the formula III is increased or decreased relative to that found in a natural source of the compounds; (iv) the concentration of one or more of the compounds having the formula IV is increased or decreased relative to that found in a natural source of the compounds; (v) the concentration of one or more of the compounds having the formula V is increased or decreased relative to that found in a natural source of the compounds; (vi) the concentration of rubescensin J is at least about 100 µg/g, is at least about 200 µg/g, at least about 500 µg/g, at least about 1 mg/g, at least about 2 mg/g, at least about 5 mg/g, at least about 10 mg/g, at least about 100 mg/g; or is less than about 100 µg/g, less than about 50 µg/g, less than about 20 µg/g, less than about 10 µg/g; (vii) the concentration of rubescensin O-1 is at least about 100 µg/g, at least about 200 µg/g, at least about 500 µg/g, at least about 1 mg/g, at least about 2 mg/g, at least about 5 mg/g, at least about 10 mg/g, at least about 100 mg/g; or is less than about 20 µg/g, less than about 10 µg/g, less than about 5 µg/g; (viii) the concentration of rubescendepside is at least about 100 µg/g, at least about 200 µg/g, at least about 500 µg/g, at least about 1 mg/g, at least about 2 mg/g, at least about 5 mg/g, at least about 10 mg/g, at least about 100 mg/g; or is less than about 50 µg/g, less than about 20 µg/g, less than about 10 µg/g; (x) the concentration of one or more of the compounds having the formula I, II, III, IV, and/or formula V is present at a concentration greater than about 500 µg/g, about 1 mg/g, about 2 mg/g, about 5 mg/g, about 10 mg/g, or about 100 mg/g of the composition; and/or. (x) the level of one or more of the compounds having the formula I, II, III, IV, and/or formula V is present at greater than or equal to about 1 part per million (ppm), about 2 ppm, about 5 ppm, about 10 ppm, about 20 ppm, about 50 ppm, about 100 ppm, about 150 ppm, about 200 ppm, about 250 ppm, about 300 ppm, about 400 ppm, about 500 ppm, about 750ppm, or about 1000 ppm.

In yet another embodiment, the invention provides a composition comprising compounds having the formula I, II, III, IV and/or formula V, or a pharmaceutically acceptable salt, solvate or hydrate thereof, or a pharmaceutically acceptable salt, solvate or hydrate thereof, wherein the percentages (by dry weight) of one or more diterpenoid or depside relative to the total content of diterpenoids or depsides is different from that in a natural source of the compounds. In one embodiment, a composition comprises diterpenoids having the formula I, II, or III which constitute at least about 10%, about 25%, at least about 35%, at least about 50%, at least about 75%, at least about 80%, or at least about 90% of the total diterpenoids in the composition.

In another embodiment, a composition comprises depsides having the formula IV or V which constitute at least about 10%, at least about 20%, at least about 25%, at least about 35%, at least about 50%, at least about 75%, at least about 80%, or at least about 90% of the total depsides in the composition. In another embodiment, a composition comprises rubescensin J which constitutes at least about 15%, at least about 20%, at least about 25%, at least about 35%, at least about 50%, at least about 75%, at least about 80%, or at least about 90% of the total diterpenoids in the composition. In another embodiment, a composition comprises rubescensin O-1 which constitutes at least about 15%, at least about 20%, at least about 25%, at least about 35%, at least about 50%, at least about 75%, at least about 80%, or at least about 90% of the total diterpenoids in the composition. In another embodiment, a composition comprises rubescendepside which constitutes at least about 15%, at least about 20%, at least about 25%, at least about 35%, at least about 50%, at least about 75%, at least about 80%, or at least about 90% of the total depsides in the composition.

In another embodiment, a composition of the invention comprises compounds having the formula I, II, III, IV, and/or formula V or a pharmaceutically acceptable salt, solvate or hydrate thereof, or a pharmaceutically or physiologically acceptable salt, solvate or hydrate thereof, wherein the ratio of certain diterpenoids and/or depsides in the composition is different from that found in a natural source of the compounds.

To distinguish different mixtures or compositions, including natural sources of the compounds, not all diterpenoids or depsides in the compositions need to be quantified as long as there is at least one difference in the concentration of at least one diterpenoid or depside compound relative to that found in a natural source of the compounds and/or in the ratio of at least two diterpenoid or depside compounds relative to that found in a natural source of the compounds. The ratio can be expressed as a quotient of the concentrations or amounts of the respective compounds in the mixtures. Accordingly, the compositions of the invention can be described by stating that the ratio of two or more specific diterpenoid or depside compounds is greater than, equal to, or less than a ratio or a specified set of ratios. The ratio of two diterpenoids or two depsides in a composition of the invention can also be represented by the expression p:q, where p and q are integers, e.g., 1:1, 2:1, 3:1, 4:1, 5:1, 10:1, 15:1, 20:1, 50:1, 75:1, 100:1, 200:1, 500:1, 1000:1.

In certain embodiments, a composition comprises one or more compounds of the invention wherein the concentration of a compound in the composition ranges from about 0.001% (w/w) to about 95% (w/w) of the composition. For example, in some embodiments, the compound is selected from the group consisting of rubescensin J, rebescensin O-1, rubscendepside, rubescensin M, rabdoternin A, rabdoternin B and rabdoternin C. In some embodiments, the concentration of the compound in the composition is about 0.005% (w/w), about 0.01% (w/w), about 0.05% (w/w), about 0.1% (w/w), about 0.5% (w/w), about 1% (w/w), about 5% (w/w), about 10% (w/w), about 15% (w/w), about 20% (w/w), about 25% (w/w), about 30% (w/w), about 40% (w/w), about 50% (w/w), about 60% (w/w), about 70% (w/w), about 80% (w/w), or about 90% (w/w). In addition to one or more compounds of the invention, such compositions can comprise any number of natural or synthetic ingredients or components including, e.g., solvents, that are not a compound of the invention.

In certain embodiments, certain-compounds, such as but not limited to one or more of the following: oridonin (rubescensin A), ponicidin (rubescensin B), rosthorin, effusanin E, rubescensin I, rubescensin J, rubescensin K, rubescensin L, rubescensin P, rubescensin M, rubescensin Q, rabdoternin A, rabdoternin B, rabdoternin C, and rubescendepside, are selectively removed or substantially depleted from a natural source of the compounds of the invention, such as an extract of *Rabdosia rubescens*. For example, a composition of the invention can comprise less than about 99%, about 95%, about 90%, about 80%, about 70%, about 75%, about 60%, about 50%, about 40%, about 20% of the original level of such compound(s) in a natural source or an extract of *Rabdosia rubescens*.

In one aspect, the present invention provides compounds having formula I, II, III, IV or V that inhibit cancer or tumor growth in vivo and/or in vitro. In certain embodiments, the compounds provide reversal of tumor volume or cancer cell numbers in vivo. In other embodiments, a composition comprises a safe and effective amount of a compound of the invention. As used herein, the term "safe and effective amount" refers to an amount that is sufficient to produce a beneficial effect, but low enough to avoid undesirable side effects, (e.g., toxicity or allergic reaction), i.e., to provide a reasonable benefit to risk ratio, within the scope of sound medical judgment. The activities of such compounds and compositions can be demonstrated by many known methods in the art, such as but not limited to the cells and methods described in Section 6.

In some embodiments, the invention encompasses compounds having formula I, II, III, IV or V that inhibits neoplastic transformation of JB6 cells by at least 50% at concentrations of about 100 $\mu$M, about 80 $\mu$M, about 75 $\mu$M, about 60 $\mu$M, about 50 $\mu$M, about 40 $\mu$M, about 30 $\mu$M, about 25 $\mu$M, or about 10 $\mu$M, or less than 10 $\mu$M. In some embodiments, the invention provides compounds having formula I, II, III, IV or V that inhibits HCT116 colon cancer cell growth by at least 50% at concentrations of 100 $\mu$M, about 80 $\mu$M, about 75 $\mu$M, about 60 $\mu$M, about 50 $\mu$M, about 40 $\mu$M, about 30 $\mu$M, about 25 $\mu$M, or about 10 $\mu$M or less than 10 $\mu$M. In some embodiments, the invention provides compounds having formula I, II, III, IV or V that inhibits SK-MEL-28 skin cancer cell growth by at least 50% at concentrations of about 100 $\mu$M, about 80 $\mu$M, about 75 $\mu$M, about 60 $\mu$M, about 50 $\mu$M, about 40 $\mu$M, about 30 atM, about 25 $\mu$M, or about 10 $\mu$M, or less than 10 $\mu$M. In some embodiments, the invention provides compounds having formula I, II, III, IV or V that inhibits HT460 lung cancer cell growth by at least 50% at concentrations of about 100 $\mu$M, about 80 $\mu$M, about 75 $\mu$M, about 60 $\mu$M, about 50 $\mu$M, about 40 $\mu$M, about 30 $\mu$M, about 25 $\mu$M, or about 10 $\mu$M, or less than 10 $\mu$M.

In certain embodiments, a composition of the invention does not consist of a composition described in any one of the following references: de la Taille et al., 2000, Journal of Alternative & Complementary Medicine, 6(5): 449-51; Han et al., 2004a, Tetrahedron Letters 45(13): 2833-2837; Han et al., 2004b, Tetrahedron Letter, 60(10): 2373-2377; Han et al., 2003a, Heterocycles, 60(4): 933-938; Han et al., 2003b, Helvetica Chimica Acta, 86(3): 773-777; Han et al., 2003, Youji Huaxue 23(3): 270-273; Han et al., 2003, Huaxue Xuebao, 61(7): 1077-1082; Ikezoe et al., 2003, International Journal of Oncology, 23(4): 1187-1193; Li et al., 2002, Polish Journal of Chemistry, 76(5): 721-724; Li et al., 2000a, Phytochemistry 53(8): 855-859; .Li et al., 2000b, Chinese Chemical Letters, 11(1): 43-44; Liu et al., 2000, Chemical & Pharmaceutical Bulletin 48(1): 148-149; Liu et al., 2000, Tianran Chanwu Yanjiu Yu Kaifa 12(2): 4-7; Zhao et al., 2000, Henan Yike Daxue Xuebao, 35(2): 138-139; Bai et al., Abstracts of Papers, 223rd ACS National Meeting, Orlando, Fla., United States, Apr. 7-11, 2002: AGFD-093; Meade-Tollin et al., 2004, Journal of Natural Products, 67(1): 2-4, U.S. Pat. No. 5,665,393, U.S. patent publication US2003-0035851A1, which are incorporated herein by reference in their entirety. In a specific embodiment, a composition of the invention is not the herbal mixture known under the name of SPES or PC-SPES. In certain embodiments, a composition of the invention does not consist of any one or more of the following compounds or plant extracts: lupulone or an extract of *Humulus lupulus*; bavachin, bavachalcone, bavachinin, and/or bavachromene or an extract of *Psoralea corylifolia* L.; gensenoside or an extract of *Panax pseudo-ginseng* Wall; baicalin or an extract of *Scutellaria baicalensis* Georgi; soy flavonoid and soy isoflavonoid or extracts of *Glycine max*; curcummin or an extract of *Curcuma ionga*; an extract of *Dendranthema morifolium*; an extract of *Ganoderma lucidium*; an extract of *Glycyrrhiza uraensis*; extract of *Isatis indigotica*; or an extract of *Serenoa repens*.

In various embodiments, depending on the intended use and without limitation, a composition of the invention can be a nutraceutical composition, a cosmetic composition or a pharamceutical composition.

In the various embodiments, the diterpenoid and/or depside compounds of the invention can be administered either alone or in combination with natural products and their derivatives. For example, natural products and derivatives, such as botanical extracts, that have immunomodulatory activity, anti-angiogenic activity, anti-TNFα activitiy, anti-inflammatory activity, anti-infective activity, antiviral activity and/or anticancer activity can be used in combination with the compounds of the invention. Non-limiting examples of such extracts include but are not limited to rosemary extracts, green tea extracts, black tea extracts, orange peel extracts, licorice root extracts, resveratrol compounds and derivatives, Inula extracts, Mexican bamboo extracts, or Huzhang extracts. Purified compounds and derivatives thereof present in such extracts can also be used.

For example, phytochemicals or plant extracts can be used in combination with the compounds and compositions of the invention. Non-limiting examples of phytochemicals or plant extracts that can be used in combination with the compounds and compositions of the invention are disclosed in U.S. Pat. Nos. 6,498,195, 6,627,623, 6,790,869, international patent publications nos. WO 01/21137, WO 02/39956, which are incorporated herein by reference in their entirety.

5.4 Nutraceutical Compositions

In one embodiment, a composition of the invention can be a nutraceutical composition. As used herein, the terms "nutraceutical" or "nutraceutical composition of the invention" are used interchangeably to refer to, a composition comprising a compound of the invention, and include without limitation, food compositions, food additives, food compositions in bulk, food additives in bulk, dietary supplements, medical foods, and foods for special dietary use, of the invention. Accordingly, a nutraceutical composition is a composition, such as a composition as described in Section 5.3 above, that comprises one or more compound(s) of the invention, i.e., compounds having a formula I, II, III, IV, or V, e.g., rubescensin J, rubescensin O-1, and/or rubescendepside, and preferably, in an effective amount, therapeutically, prophylactically or otherwise. In various embodiments, a nutraceutical composition of the invention typically comprises one or more consumable vehicles, carriers, excipients, or fillers. The term "consumable" means generally suitable for, or is approved by a regulatory agency of the Federal or a state government for, consumption by animals, and more particularly by humans.

As used herein, "food" means any substance, whether processed, semi-processed, or raw, which is intended for consumption by animals including humans, but does not include cosmetics, tobacco products or substances used only as pharmaceuticals.

In one embodiment, the term "food composition" refers to a food which comprises one or more composition(s) or compound(s) of the invention. Any food to which a composition or compound of the invention is added is a food composition of the invention. Any food in which a compound of the invention is made to be present at a greater level is also a food composition of the invention.

Food compositions of the invention include but are not limited to confectionery such as biscuits, chocolates, candies, chewing gums, snacks, cakes, ice creams and jellies; baked products such as but not limited to breads and pies; pastas; noodles; processed soybean products such as tofu (bean curd); dairy products such as but not limited to yoghurt and butter; processed meat products such as but not limited to ham, hamburgers, and sausage; fermented products; processed egg products such as tamago-yaki and egg custard; processed seafood based products such as ground fish meat products and imitation crab meat; seasonings such as sauce, dressing, mayonnaise and furikake (rice topping); dried fruits; cereals; pizzas; instant noodles; soups; snacks (e.g., chips, pretzels); and nutrition supplements such as food bars, sports bars and the like, which comprise one or more composition(s) or compound(s) of the invention.

Food compositions of the invention also include but are not limited to single cell protein, protein concentrates or isolates prepared from plants, algae, plant cell cultures, microorganisms, and animals, leaf meals, seed meals, concentrates and isolates from soybean, cottonseed, peanut, fish meal, and concentrates from meat, organs, and/or bones, which comprise one or more composition(s) or compound(s) of the invention.

Food compositions of the invention also include a beverage, such as but not limited to fortified mineral water, fortified distilled water, a fruit juice-based beverage, a shake, a carbonated beverage, a lactic acid beverage, a sport beverage, milk, a milk-based beverage, a dairy product-based beverage, a yoghurt-based beverage, a carbonated water-based beverage, an alcoholic drink, a coffee-based beverage, a tea-based beverage, a green tea-based beverage, a black tea-based beverage, a grain-based beverage, a soybean-based beverage, soya-milk, an aloe-based beverage, a carbonated soft drink beverage, or a beverage based on plant extracts, which comprises one or more composition(s) or compound(s) of the invention. In a specific embodiment, a food composition of the invention can be a reconstitutable powder that, when reconstituted with a liquid, such as drinking water, can provide a beverage.

In another embodiment, the invention provides a food additive comprising one or more composition(s) or compound(s) of the invention. As used herein, the term "food additive" refers to any substance not normally consumed as a food by itself and not normally used as a typical ingredient of the food, whether or not it has nutritive value, but which is intentionally added to food. For example, the intentional addition of food additive to food is for a technical purpose, including an organoleptic purpose, in the manufacture, processing, preparation, treatment, packing, packaging, transport, or holding of such food. The use of a food additive results, or may be reasonably expected to result, (directly or indirectly) in it or its by-products becoming a component of or otherwise affecting the characteristics of the food. In a specific embodiment, a food additive of the invention can be added to a food resulting in a food composition of the invention.

In various embodiments, a food additive of the invention can be added to ingredients used in food preparation. Any methods known to those skilled in the art may be used to add to or incorporate a food additive of the invention in solid form or liquid form into natural or processed foodstuff. For example, a food additive of the invention can be used by the food industry to fortify bulk food ingredients or to prepare food products, or by consumers durin g food preparation. In one embodiment, a food additve of the invention can be incorporated into basic food ingredients, such as but not limited to syrups, starches, grains, flour, fats and oils (e.g., cooking oil, frying oil, salad oil, margarine, mayonnaise or peanut butter), dietary fibers and bulking agents. In another embodiment, the food additives of the invention can be used to prepare water-based food compositions. Moreover, oil-based food additives of the invention can be emulsified and used in a variety of drinks.

The compounds and compositions of the invention can also be added to other food additives. Other food additives which can be fortified with compound(s) and compositions of the invention include but are not limited to natural sweetners, artificial sweetners, acidulants, anticaking agents, antioxidants, coloring agents, curing and pickling agents, emulsifiers, enzymes, fat replacers, firming agents, natural flavors, artificial flavors, flavor enhancers, humectants, leavening agents, lubricants, preservatives, stabilizers and thickeners.

Examples of food additives acceptable in manufacturing foods and beverages of the invention include sweeteners such as sucrose, glucose, fructose, isomerized liquid sugars, fructoligosaccharide, aspartame, sorbitol, sucralose, dextrin, maltodextrin, and stevia; coloring agents such as red cabbage colorant, grape pericarp colorant, elderberry colorant, caramel, gardenia colorant, corn colorant, saffron colorant and carotene; preservatives such as pectin decomposition products, benzoic acid, sorbic acid, parabens and potassium sorbate; thickeners such as sodium alginate, propylene glycol alginate, calcium cellulose glycolate and sodium cellulose glycolate; antioxidants such as L-ascorbic acid, tocopherol, erythrobic acid and rutin; color developing agents such as ferrous sulfate, sodium nitrite and potassium nitrate; bleaching agents such as sodium hydrogen nitrite and potassium metabisulfite; quality-keeping agents such as propylene glycol; quality improving agents such as L-cysteine hydrochloride and calcium stearyl lactate; inflating agents such as ammonium chloride, potassium hydrogen D-tartrate, ammonium carbonate, potassium carbonate, sodium hydrogen carbonate and alum; emulsifiers such as lecithin, sphingo-lipids, vegetable sterols, soybean saponin, sodium alginate, propylene glycol alginate, casein sodium, glycerol fatty acid esters, sucrose fatty acid esters and sorbitan fatty acid esters; emulsion stabilizers such as sodium chondroitin sulfate; flavoring substances such as lemon oil, eucalyptus oil, peppermint oil, vanilla extract, orange oil, garlic oil, ethyl acetoacetate, anisaldehyde, ethyl vanillin, cinnamic acid, citronellyl acetate, citral, vanillin, butyl butyrate and esters; nourishing agents such as L-ascorbic acid, L-asparagine, L-alanine, inositol, L-glutamine, carotene, tocopherol, vitamin A, folic acid, iron citrate, heme iron and uncalcined calcium; wheat flour-improving agents such as benzoyl peroxide, ammonium persulfate and chlorine dioxide; bactericides such as bleaching powder, hydrogen peroxide and hypochlorous acid; chewing gum bases such as methyl acetylricinolate, ester gum, vinyl acetate resin, polyisobutylene and polybutene; anti-blocking agents such as D-mannitol; integrating agents such as acidic sodium pyrophosphate, potassium pyrophosphate and sodium pyrophosphate; acidifiers such as adipic acid, citric acid, gluconic acid, succinic acid, D-tartaric acid, lactic acid and DL-malic acid; and seasonings such as fish extract, yeast extract, soy sauce, tomato puree, meat extract, mirin, fruit puree, dried bonito, sodium L-aspartate, DL-alanine, L-arginine L-glutamate, disodium 5'-inosinate, trisodium citrate, L-glutamic acid, sodium L-glutamate, succinic acid, L-tartaric acid and sodium lactate.

In another embodiment, the invention provides a dietary supplement comprising one or more compound(s) or compositions of the invention. As used herein, the term "dietary supplement" means a product (other than tobacco) intended to supplement the diet. Typically, a dietary supplement is a product that is labeled as a dietary supplement and is not represented for use as a conventional food or as a sole item of a meal or the diet. A dietary supplement of the invention can typically comprises one or more of the following dietary ingredients: a vitamin;a mineral; an herb or other botanical; an amino acid; a dietary supplement used by man to supplement the diet by increasing the total dietary intake; or a concentrate, metabolite, constituent, extract, or a combination of any of the ingredients. A dietary supplement can be consumed by a subject independent of any food, unlike a food additive which is incorporated into a food or food composition during the processing, manufacture, preparation, or delivery of the food or food composition, or just prior to its consumption.

In yet another embodiment, the invention provides a medical food comprising one or more compound(s) or composition(s) of the invention. As used herein, the term "medical food" refers to a food which is formulated to be consumed or administered enterally under the supervision of a physician and which is intended for the specific dietary management of a disease or condition for which distinctive nutritional requirements, based on recognized scientific principles, are established by medical evaluation. Examples of medical foods include but are not limited to sole source nutrition products which are complete nutritional products used to replace all other food intake; oral rehydration solutions for use in replacing fluids and electrolytes lost following diarrhea or vomiting; modular nutrient products containing specially selected components not intended to be complete nutritional sources but designed for the management of specific diseases and which have associated claims to effectiveness either direct or implied; and products intended for use in dietary management of inborn errors of metabolism.

In yet another embodiment, the invention provides a food for special dietary use comprising one or more compound(s) or composition(s) of the invention. As used herein, the term "food for special dietary use" refers to a food which purports or is represented to be used, for at least one of the following: supplying a special dietary need that exists by reason of a physical, physiological, pathological, or other condition, including but not limited to the condition of disease, convalescence, pregnancy, lactation, infancy, allergic hypersensitivity to food, underweight, overweight, or the need to control the intake of sodium; supplying a vitamin, mineral, or other ingredient for use by man to supplement his diet by increasing the total dietary intake; and supplying a special dietary need by reason of being a food for use as the sole item of the diet.

The nutracential compositions of the invention can also include one or more other ingredients that impart additional healthful or medicinal benefit. The optional ingredients useful herein can be categorized by their healthful benefit or their postulated mode of action. However, it is to be understood that the optional components useful herein can in some instances provide more than one healthful benefit or operate via more than one mode of action. Therefore, classifications herein are made for the sake of convenience and are not intended to limit the component to any particular mechanism of action or to that particular application or applications listed.

A nutracential composition can comprise in addition to one or more compound(s) or composition(s) of the invention, one or more additional ingredient(s), such as but not limited to vitamins, minerals, electrolytes, sports nutritional products, amino acids, probiotics, metabolites, hormones, enzymes, cartilage products, botanical extracts, and homeopathic products. More specifically, a nutracential composition of the invention can further one or more substance(s) from the following non-limiting categories: (i) amino acids and oligopeptides, such as but not limited to 5-hydroxytryptophan, acetyl-L-carnitine, acetylcysteine, arginine pyroglutamate, branched-chain amino acids, creatine, DL-phenylalanine (phenylalanine), dimethylglycine (DMG), glutamine peptides, glutathione, glycine, insulin-like growth factor 1, L-arginine (arginine), L-aspartate, L-carnitine, L-cysteine, L-glutamine, L-histidine, L-lysine (lysine), L-methionine (methionine), L-ornithine, L-phenylalanine (phenylalanine), L-theanine, L-tyrosine (tyrosine), lactoferrin, ornithine alpha-ketoglutarate, para-aminobenzoic acid (aminobenzoic acid), taurine; (ii) glycosupplements, such as but not limited to chitosan, chondroitin sulfate, D-glucarate, D-ribose, fructo-oligosaccharides, glucomannan, glucosamine, inulins (inulin), lactulose, larch arabinogalactan, modified citrus pectin, pectin, psyllium (psyllium husk), sodium alginates, yeast beta-D-glucans; (iii) hormones, such as but not limited to 19-norandrostenedione, androstenediol, androstanedione, beta-sitosterol, biochanin A, DHEA, glandulars, human growth hormone and secretagogues (somatropin), ipriflavone, melatonin, pregnenolone, soy isoflavones, tiratricol (TRIAC); lipids such as but not limited to alkoxyglycerols, blackcurrant seed oil, borage oil, caprylic acid, cetyl myristoleate, conjugated linoleic acid (CLA), docahexaenoic acid (DHA), eicosapentaenoic acid (EPA), evening primrose oil, fish oil, flaxseed oil, gamma-linolenic acid (GLA), glycerol (glycerin), hemp seed oil, hexacosanol, inositol hexaphosphate, L-alpha-glycerylphosphorylcholine (Alpha-GPC), lithium gamma-linolenic acid (Li-GLA), medium-chain triglycerides, myo-inositol, octacosanol, perilla oil, phosphatidylcholine, phosphatidylserine, policosanol, squalene, plant stanols; (iv) metabolites and cofactors such as but not limited to 7-oxo-dehydroepiandrosterone, alpha-lipoic acid, betaine and betaine hydrochloride, CDP-choline (citicolin sodium), coenzyme Q10 (CoQ10), NADH, pantethine, pyruvate, S-adenosyl-L-methione (SAMe); (v) minerals and electrolytes, such as but not limited to metal salts, chelated minerals, colloidal minerals, colloidal silver, colloidal gold, bentonite, compounds comprising aluminum, arsenic, boron, bromine, calcium, chromium, copper, fluoride, germanium, iodine, iron, lithium, magnesium, manganese, molybdenum, nickel, phosphorus, potassium, selenium, selenium, silicon, tin, vanadium, and zinc; (vi) mycosupplements such as but not limited to brewer's yeast, kombucha, myco-polysaccharides, red yeast rice; (vii) inosine, nucleic acids, nucleotides; (viii) microorganisms such as but limited to prebiotics, probiotics, synbiotics, yoghurt organisms; (ix) proteins such as but not limited to bovine cartilage, bovine colostrum, bromelain (bromelains), chicken collagen II, gelatin hydrolysates (gelatin), hydrolyzed collagen, shark cartilage, soy protein, whey proteins; (x) vitamins in either natural or synthetic form, such as but are not limited to, vitamin A (e.g., beta carotene, retinoic acid, retinol, retinoids, retinyl palmitate, retinyl proprionate, etc.), vitamin B (e.g., niacin, niacinamide, riboflavin, pantothenic acid, etc.), vitamin B6 (pyridoxine hydrochloride), vitamin B12 (cyanocobalamin), vitamin C (e.g., ascorbic acid, etc.), vitamin D (e.g., ergosterol, ergocalciferol, cholecalciferol, etc.), Vitamin E (e.g., tocopherol acetate, etc.), vitamin K (e.g., phytonadione, menadione, phthiocol, etc.), alpha-tocopheryl nicotinate, alpha-tocopheryl polyethylene glycol succinate, ascorbyl palmitate, biotin, folate (folio acid), gamma-tocopherol, inositol nicotinate (inositol niacinate), niacin, nicotinamide (niacinamide), pantothenic acid (calcium pantothenate), thiamin, and tocotrienols; (xi) botantical extracts such as DHEA, Ginkgo biloba extracts, ginseng extracts, reisi (Ganoderma) extract; and (xii) other supplements known in the art such as but not limited to activated charcoal, beta-hydroxy-beta-methylbutyrate (HMB), choline, colosolic acid, deanol, dimethyl sulfoxide (DMSO), dolomite, gamma-butyrolactone (GBL), gamma-hydroxybutyrate (GHB), liver hydrolysate/desiccated liver, malic acid, methylsulfonylmethane (MSM), royal jelly, vinpocetine, arnica, bee pollen, chlorella, chlorophyll/chlorophyllin (chlorophyllin copper complex), chrysin, cocoa flavonoids, curcuminoids, daidzein, deglycyrrhizinated licorice (DGL), flower pollen, genistein, glycitein, grape seed proanthocyanidins, green tea catechins, black tea theaflavins, hesperetin, hesperidin, huperzine A, hydroxycitric acid, hydroxyethylrutosides, indole-3-carbinol, lutein and zeaxanthin, lycopene, oat beta-D-glucan, phytostanols, phytosterols, piperine, propolis, pycnogenol, quercetin, resveratrol, rutin, secoisolariciresinol diglycoside (SDG), soy isoflavones, spirulina, sulforaphane, wheat grass/barley grass.

Non-limiting examples of minerals and electrolytes include but are not limited to calcium compounds, calcium carbonate, calcium citrate, iron compounds, iron fumarate, iron gluconate, iron sulfate, magnesium compounds, magnesium carbonate, magnesium chloride, magnesium gluconate, selenium compounds, sodium compounds, and manganese compounds.

Also encompassed by the invention are nutraceutical compositions comprising one or more compound(s) or composition(s) of the invention and one or more "Generally Regarded As Safe" ("GRAS") substance(s). Many GRAS substances are known and are listed in the various sections of the regulations of the United States public health authority, 21 CFR 73, 74, 75, 172, 173, 182, 184 and 186, which are incorporated herein by reference in their entirety. Thus, in various embodiments, a dietary supplement, food composition or food additive of the invention comprises one or more GRAS substances.

For example, the following exemplary GRAS flavor alcohols can be used in combination with the compounds and compositions of the invention, benzyl alcohol, acetoin (acetylmethylcarbinol), ethyl alcohol (ethanol), propyl alcohol (1-propanol), iso-propyl alcohol (2-propanol, isopropanol), propylene glycol, glycerol, n-butyl alcohol (n-propyl carbinol), iso-butyl alcohol (2-methyl-1-propanol), hexyl alcohol (hexanol), L-menthol, octyl alcohol (n-octanol), cinnamyl alcohol (3-phenyl-2-propene-1-ol), .alpha.-methylbenzyl alcohol (1-phenyl-ethanol), heptyl alcohol (heptanol), n-amyl alcohol (1-pentanol), iso-amyl alcohol (3-methyl-1-butanol), anisalcohol (4-methoxybenzyl alcohol, p-anisalcohol), citronellol, n-decyl alcohol (n-decanol), geraniol, beta-gamma-hexanol (3-hexenol), lauryl alcohol (dodecanol), linalool, nerolidol, nonadienol (2,6-nonadiene-1-ol), nonyl alcohol (nonanol-1), rhodinol, terpineol, borneol, clineol (eucalyptol), anisole, cuminyl alcohol (cuminol), 10-undecen-1-ol, 1-hexadecanol. Suitable derivatives include, for example, the esters, ethers and carbonates of the above mentioned GRAS flavor alcohols are also contemplated. Particularly preferred GRAS flavor alcohols are benzyl alcohol, 1-propanol, glycerol, propylene glycol, n-butyl alcohol, citronellol, hexanol, linalool, acetoin and their derivatives.

Also encompassed is the inclusion of one or more GRAS polyphenols in the nutraceutical compositions of the invention, such as but not limited to catechol, resorcinol, hydroquinone, phloroglucinol, pyrogallol, cyclohexane, usnic acid, acylpolyphenols, lignins, anthocyans, flavones, catechols, gallic acid derivatives (e.g., tannins, gallotannin, tannic acids, gallotannic acids), catechins, theaflavins, carnosol, carnosolic acid (including their derivatives, such as (2,5-dihydroxyphenyl)carboxylic and (2,5-dihydroxyphenyl)alkylenecarboxylic substitutions, salts, esters, amides), caffeic acid and its esters and amides, flavonoids (e.g., flavone, flavonol, isoflavone, gossypetin, myricetin, robinetin, apigenin, morin, taxifolin, eriodictyol, naringin, rutin, hesperidin, troxerutin, chrysin, tangeritin, luteolin, catechols, quercetin, fisetin, kaempferol, galangin, rotenoids, aurones, flavonols, diols), extracts, e.g., from Camellia (*C. sinensis* in particular), or Primula. Further, their derivatives, e.g., salts, acids, esters, oxides and ethers, may also be used.

Also encompassed is the inclusion of one or more GRAS acids in the nutraceutical compositions of the invention, such as but not limited to acetic acid, aconitic acid, adipic acid, formic acid, malic acid (1-hydroxysuccinic acid), capronic acid, hydrocinnamic acid (3-phenyl-1-propionic acid), pelargonic acid (nonanoic acid), lactic acid (2-hydroxypropionic acid), phenoxyacetic acid (glycolic acid phenyl ether), phenylacetic acid (alpha-toluenic acid), valeric acid (pentanoic acid), iso-valeric acid (3-methylbutyric acid), cinnamic acid (3-phenylpropenoic acid), citric acid, mandelic acid (hydroxyphenylacetic acid), tartaric acid (2,3-dihydroxybutanedioic acid; 2,3-dihydroxysuccinic acid), fumaric acid, tannic acid and their derivatives. Suitable derivatives according to the present invention are esters (e.g., $C_{1-6}$-alkyl esters and benzyl esters), amides (including N-substituted amides) and salts (alkali, alkaline earth and ammonium salts) of the above mentioned acids. According to the present invention, the term "derivatives" also encompasses modifications of the side-chain hydroxy functions (e.g., acyl and alkyl derivatives) and modifications of the double bonds (e.g., the perhydrogenated and hydroxylated derivatives of the mentioned acids).

Also encompassed is the inclusion of one or more GRAS phenols in the nutraceutical compositions of the invention, such as but not limited to thymol, methyleugenol, acetyleugenol, safrol, eugenol, isoeugenol, anethole, methylchavicol (estragol; 3-(4-methoxyphenyl)-1-propene), carvacrol, alpha-bisabolol, fomesol, anisole (methoxybenzene), propenylguaethol (5-propenyl-2-ethoxyphenol) and their derivatives. Derivatives according to the present invention are compounds in which the phenolic hydroxy group has been esterified or etherified.

Also encompassed is the inclusion of one or more GRAS esters in the nutraceutical compositions of the invention, such as but not limited to allicin and the following acetates may be used, for example: iso-amyl acetate (3-methyl-1-butyl acetate), benzyl acetate, benzylphenyl acetate, n-butyl acetate, cinnamyl acetate (3-phenylpropenyl acetate), citronellyl acetate, ethyl acetate (acetic ester), eugenol acetate (acetyleugenol), geranyl acetate, hexyl acetate (hexanyl ethanoate), hydrocinnamyl acetate (3-phenylpropyl acetate), linalyl acetate, octyl acetate, phenylethyl acetate, terpinyl acetate, triacetin (glyceryl triacetate), potassium acetate, sodium acetate and calcium acetate.

Also encompassed is the inclusion of one or more GRAS terpenes in the nutraceutical compositions of the invention, such as but not limited to camphor, limonene and beta-caryophyllene.

Also encompassed is the inclusion of one or more GRAS acetals in the nutraceutical compositions of the invention, such as but not limited to acetal, acetaldehyde dibutyl acetal, acetaldehyde dipropyl acetal, acetaldehyde phenethyl propyl acetal, cinnamic aldehyde ethylene glycol acetal, decanal dimethyl acetal, heptanal dimethyl acetal, heptanal glyceryl acetal and benzaldehyde propylene glycol acetal.

Also encompassed is the inclusion of one or more GRAS acetaldehydes in the nutraceutical compositions of the invention, such as but not limited to acetaldehyde, anisaldehyde, benzaldehyde, iso-butyl aldehyde (methyl-1-propanal), citral, citronellal, n-caprylic aldehyde (n-decanal), ethylvanillin, furfural, heliotropin (piperonal), heptyl aldehyde (heptanal), hexyl aldehyde (hexanal), 2-hexenal (beta-propylacrolein), hydrocinnamic aldehyde (3-phenyl-1-propanal), lauryl aldehyde (dodecanal), nonyl aldehyde (n-nonanal), octyl aldehyde (n-octanal), phenylacetaldehyde (1-oxo-2-phenylethane), propionaldehyde (propanal), vanillin, cinnamic aldehyde (3-phenylpropenal), perillaldehyde and cuminaldehyde.

Also encompassed is the inclusion of one or more GRAS essential oils in the nutraceutical compositions of the invention, such as but not limited to essential oils and/or alcoholic or glycolic extracts or extracts obtained by high-pressure carbon-dioxide processes from plants such as : oils or extracts having a high content of alcohols: melissa, coriander, cardamon, eucalyptus; oils or extracts having a high content of aldehydes: Eucalyptus citriodora, cinnamon, lemon, lemon grass, melissa, citronella, lime, orange; oils or extracts having a high content of phenols: origanum, thyme, rosemary, orange, clove, fennel, camphor, mandarin, anise, cascarilla, estragon and pimento; oils or extracts having a high content of acetates: lavender; oils or extracts having a high content of esters: mustard, onion, garlic; oils or extracts having a high content of terpenes: pepper, bitter orange, caraway, dill, lemon, peppermint, nutmeg; oils or extracts having a high content of acids: olibanum.

Any of the additional substances in a nutraceutical composition of the invention may be included as pure or substantially pure material, or for example, as an extract obtained by suitable physical and/or chemical isolation from natural (e.g., plant) sources.

In certain embodiments, the meaning of the term "medical food", "food for special dietary use", "dietary supplement" or "food additive" is the meaning of those terms as defined by a regulatory agency of the Federal or a state government, including the United States Food and Drug Administraion.

In certain embodiments, the nutraceutical compositions of the present invention comprise from about 0.001% to about 90%, by weight of the compound(s) or composition of the invention. Other amounts of the combination that are also contemplated are from about 0.0075% to about 75%, about 0.005% to about 50%, about 0.01% to about 35%, 0.1% to about 20%, 0.1% to about 15%, 1% to about 10%, and 2% to about 7%, by weight of the compound(s) or composition of the invention.

5.5 Pharamceutical Compositions

The present invention provides compositions for the treatment, prophylaxis, and amelioration of a disorder in a subject. In one embodiment, a composition comprises one, two, three, four or more compounds of the invention, or a pharmaceutically acceptable salt, solvate, or hydrate thereof. In another embodiment, a composition comprises compounds of the invention in the form of an extract of *Rabdosia rubescens*, e.g. an extract prepared as described in Section 5.2 and in the Example sections, and a pharmaceutically acceptable salt, solvate, or hydrate thereof. The compositions comprising a compound or an extract of *Rabdosia rubescens*, of the invention include bulk-drug compositions (which can be non-sterile) useful in the manufacture of pharmacuetical compositions and in the preparation of unit dosage forms. Any of the nutraceutical compositions of the invention can also be formulated as a pharmaceutical composition by one of skilled in the art.

As used herein, the phrase "pharmaceutically acceptable salt" refers to pharmaceutically acceptable organic or inorganic salts of a compound of the invention. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p toluenesulfonate, and pamoate (i.e., 1,1'-methylene bis (2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counterion.

As used herein, the term "pharmaceutically acceptable solvate" refers to an association of one or more solvent molecules and a compound of the invention. Examples of solvents that form pharmaceutically acceptable solvates include, but are not limited to, water, isopropanol, ethanol, methanol, DMSO, ethyl acetate, acetic acid, and ethanolamine.

In one embodiment, a composition of the invention is a pharmaceutical composition or a single unit dosage form. Pharmaceutical compositions and single unit dosage forms of the invention comprise a prophylactically or therapeutically effective amount of one or more compositions (e.g., a compound of the invention, or other prophylactic or therapeutic agent), and a typically one or more vehicles, carriers, or excipients. Preferably, the vehicles, carriers, or excipients are pharmaceutically acceptable. The term "pharmaceutically acceptable" means approved by a regulatory agency of the Federal or a state government or listed in the U.S. Pharmacopeia or other generally recognized pharmacopeia for use in animals, and more particularly in humans.

This invention further encompasses anhydrous pharmaceutical compositions and dosage forms. Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The term "vehicle" refers to a diluent, adjuvant, excipient, carrier, or filler with which the compound or composition of the invention is stored, transported, and/or administered. Suitable vehicles are well-known to those skilled in the art of pharmacy, and non-limiting examples of suitable vehicles include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Such pharmaceutical vehicles can be sterile liquids, such as water and oils, including those of petroleum, animal, vegetable or synthetic origin, such as peanut oil, soybean oil, mineral oil, sesame oil and the like. Water is a preferred vehicle when the pharmaceutical composition is administered intravenously. Saline solutions and aqueous dextrose and glycerol solutions can also be employed as liquid vehicles, particularly for injectable solutions. Whether a particular vehicle is suitable for incorporation into a pharmaceutical or nutraceutical composition or dosage form depends on a variety of factors well known in the art including, but not limited to, the way in which the dosage form will be administered to a patient and the specific active ingredients in the dosage form. The composition or single unit dosage form, if desired, can also contain minor amounts of wetting or emulsifying agents, or pH buffering agents.

The invention further encompasses pharmaceutical compositions and dosage forms that comprise one or more compounds that reduce the rate by which an active ingredient will decompose. Such compounds, which are referred to herein as stabilizers, include, but are not limited to, antioxidants such as ascorbic acid, pH buffers, or salt buffers.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, intra-tumoral, intra-synovial and rectal administration. In various embodiments, the pharmaceutical compositions or single unit dosage forms are sterile and in suitable form for administration to a subject, preferably an animal subject, more preferably a mammalian subject, and most preferably a human subject.

The composition, shape, and type of dosage forms of the invention will typically vary depending on their use. Examples of dosage forms include, but are not limited to: tablets; caplets; capsules, such as soft elastic gelatin capsules; pills, pellets, capsules containing liquids cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. Formulations in the form of powders or granulates may be prepared using the ingredients mentioned above under tablets and capsules in a conventional manner using, e.g., a mixer, a fluid bed apparatus or a spray drying equipment.

Generally, a dosage form used in the acute treatment of a disorder may contain larger amounts of one or more of the active ingredients it comprises than a dosage form used in the chronic treatment of the same disease. Also, the prophylactically and therapeutically effective dosage form may vary among different types of disorders. Similarly, a parenteral dosage form may contain smaller amounts of one or more of the active ingredients it comprises than an oral dosage form used to treat the same disease or disorder. These and other ways in which specific dosage forms encompassed by this invention will vary from one another and will be readily apparent to those skilled in the art. See, e.g., Remington's Pharmaceutical Sciences, Gennaro, et al., 19th Ed., Easton, Pa., Mack Publishing Co., (1995); Remington: The Science and Practice of Pharmacy by Gennaro, Lippincott Williams & Wilkins; 20th edition (2003); Pharmaceutical Dosage Forms and Drug Delivery Systems by Howard C. Ansel et al., Lippincott Williams & Wilkins; 7th edition (October 1, 1999); and Encyclopedia of Pharmaceutical Technology, edited by Swarbrick, J. & J. C. Boylan, Marcel Dekker, Inc., New York, 1988, which are incorporated herein by reference in their entirety.

The invention also provides that a pharmaceutical composition can be packaged in a hermetically sealed container such as an ampoule or sachette indicating the quantity. In one embodiment, the pharmaceutical composition is supplied as a dry sterilized lyophilized powder or water free concentrate in a hermetically sealed container and can be reconstituted, e.g., with water or saline to the appropriate concentration for administration to a patient. The pharmaceutical compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

5.5.1 Oral Dosage Forms

The present invention provides pharmaceutical compositions that are suitable for oral administration, as well as other orally comsumable compositions comprising a compound or composition of the invention, including but not limited to nutraceutical compositions and in particular, dietary supplements of the invention. Such oral compositions can be presented as discrete dosage forms, such as, but are not limited to, tablets (e.g., chewable tablets), caplets; capsules, such as soft elastic gelatin capsules; pills, pellets, capsules containing liquids cachets; troches; lozenges; suspensions (e.g., aqueous or non-aqueous liquid suspensions, oil-in-water emulsions, or a water-in-oil liquid emulsions), solutions, and elixirs. Such dosage forms contain predetermined amounts of active ingredients, and may be prepared by methods of pharmacy well known to those skilled in the art. See generally, Remington's Pharmaceutical Sciences, and Remington: The Science and Practice of Pharmacy supra.

Typical oral dosage forms of the invention are prepared by combining the active ingredient(s) in an intimate admixture with at least one vehicle excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Formulations for oral use may also be presented as chewing tablets, or as hard gelatin capsules wherein the active ingredient is mixed with an inert solid diluent, for example, potato starch, lactose, microcrystalline cellulose, calcium carbonate, calcium phosphate or kaolin, or as soft gelatin capsules wherein the active ingredient is mixed with water or an oil medium, for example, peanut oil, liquid paraffin, or olive oil.

Liquid preparations for oral administration can take the form of, for example, solutions, syrups or suspensions, or they can be presented as a dry product for constitution with water or other suitable vehicle before use. Such liquid preparations can be prepared by conventional means with vehicles such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

In various embodiments, many excipients known in the art can be used in oral dosage forms of the invention include, but are not limited to, binders, fillers, disintegrants, lubricants, dispersing agent, wetting agent, and suspending agent. Binders suitable for use in pharmaceutical/nutraceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions, dietary supplements, and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. In one embodiment, the binder or filler in a composition of the invention can be present in from about 50 to about 99 weight percent of the pharmaceutical composition, nutraceutical composition, dietary supplement, or dosage form.

Disintegrants can be used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant so as to not to detrimentally alter the release of the active ingredients should be when utilitizing disintegrates in forming solid oral dosage forms of the invention. It is noted that disintegrants can also be employed in other, e.g., dietary supplement composition of the invention. The amount of disintegrant used varies based upon the type of formulation, and is readily discernible to those of skill in the art.

Typical pharmaceutical compositions and dietary supplement comprise from about 0.5 to about 15 weight percent of disintegrant, and in some embodiments, more particularly, from about 1 to about 5 weight percent of disintegrant.

Disintegrants that can be used in pharmaceutical compositions, dietary supplemenents and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants can be used in pharmaceutical compositions, dietary supplemenents, and dosage forms of the invention, and can include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions, dietary supplmenents, or dosage forms into which they are incorporated.

Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

5.5.2 Parenteral Dosage Forms

Parenteral dosage forms can be administered to subjects by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Typically, compositions for intravenous administration are solutions in sterile isotonic aqueous buffer.

Compounds that increase the solubility of one or more of the active ingredients disclosed herein can also be incorporated into the parenteral dosage forms of the invention. Where necessary, the composition may also include a solubilizing agent and a local anesthetic such as lignocamne to ease pain at the site of the injection.

5.5.3 Transdermal, Topical & Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences; Remington: The Science and Practice of Pharmacy supra; Pharmaceutical Dosage Forms and Drug Delivery Systems by Howard C. Ansel et al., Lippincott Williams & Wilkins; 7th edition (Oct. 1, 1999). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical and cosmetic arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Emulsifying agents, preservatives, antioxidants, gel-forming agents, chelating agents, moisturizers or humectants can also be added to pharmaceutical compositions and dosage forms if desired. Examples of such additional ingredients are well known in the art. See, e.g., Remington's Pharmaceutical Sciences; Remington: The Science and Practice of Pharmacy; Pharmaceutical Dosage Forms and Drug Delivery Systems, supra.

Examples of emulsifying agents include naturally occurring gums, e.g. gum acacia or gum tragacanth, naturally occurring phosphatides, e.g. soybean lecithin and sorbitan monooleate derivatives. Examples of antioxidants include butylated hydroxy anisole (BHA), ascorbic acid and derivatives thereof, tocopherol and derivatives thereof, butylated hydroxy anisole and eysteine. Examples of preservatives include parabens, such as methyl or propyl p- hydroxybenzoate and benzalkonium chloride. Examples of humectants include glycerin, propylene glycol, sorbitol and urea. Examples of chelating agents include sodium EDTA, citric acid and phosphoric acid. Examples of gel forming agents include Carbopol, cellulose derivatives, bentonite, alginates, gelatin and polyvinylpyrrolidone. Examples of ointment bases include beeswax, paraffin, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

In a specific embodiment, the invention provides formulations for administration to the eye in the form of eye drops, lotions, ointments or delivery devices. Typically, the composition comprises the active compound(s) in combination with vehicles or the active compound is incorporated in a suitable carrier system. Pharmaceutically inert vehicles and/or excipients for the preparation of eye drops include, e.g., buffering agents such as boric acid or borates, pH adjusting agents to obtain optimal stability or solubility of the active compound, tonicity adjusting agents such as sodium chloride or borates, viscosity adjusting agents such as hydroxypropyl cellulose, methylcellulose, polyvinylpyrrolidone, polyvinyl alcohols or polyacrylamide, oily vehicle such as vehicles comprising arachis oil, castor oil and/or mineral oil. Emulsions and suspensions of the active drug substance may also be presented in form of eye drops. In these cases, the composition may furthermore comprise stabilizing, dispersing, wetting, emulsifying and/or suspending agents.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.6 Cosmetic Compositions

In another embodiment, the present invention provides cosmetic compositions comprising one or more compositions or compounds of the invention and a cosmetic agent. The cosmetic compositions of the present invention can be utilized for providing healthful, therapeutic and aesthetic skin and/or hair benefits by contacting, deposition and/or adhesion to skin and/or hair, or by providing and maintaining body and/or hair hygiene.

Described below are nonexclusive lists of various optional and preferred components, such as cosmetic agents and carriers, that can be included in a cosmetic composition of the present invention.

Suitable cosmetic agents are well known to those in the art and include, but are not limited to those selected from the group consisting of absorbents, anti-acne agents, anti-caking agents, anti-cellulite agents, anti-foaming agents, anti-fungal agents, anti-inflammatory agents, anti-microbial agents, antioxidants, antiperspirant/deodorant agents, anti-skin atrophy agents, antiviral agents, anti-wrinkle agents, artificial tanning agents and accelerators, astringents, barrier repair agents, binders, buffering agents, bulking agents, chelating agents, colorants, dyes, enzymes, essential oils, film formers, flavors, fragrances, humectants, hydrocolloids, light diffusers, opacifying agents, optical brighteners, optical modifiers, particulates, perfumes, pH adjusters, sequestering agents, skin conditioners/moisturizers, skin feel modifiers, skin protectants, skin sensates, skin treating agents, skin exfoliating agents, skin lightening agents, skin soothing and/or healing agents, skin detergents, skin thickeners, sunscreen agents, topical anesthetics, vitamins, and combinations thereof. For further description, see, Handbook of Cosmetics Science and Technology, 1st Edition, by A. O. Barel (ed.)(2001), which is incorporated herein by reference in its entirety.

The cosmetic compositions of the present invention may also comprise a cosmetically-acceptable carrier and any optional components. Suitable carriers are well known in the art and are selected based on the end use application. For example, carriers of the present invention include, but are not limited to, those suitable for application to skin. Preferably, the carriers of the present invention are suitable for application to skin (e.g., sunscreens, creams, milks, lotions, masks, serums, etc.) or nails (e.g., polishes, treatments, etc.). Such carriers are well-known to those of skill in the art, and can include one or more compatible liquid or solid filler diluents or vehicles which are suitable for application to skin and nails. The exact amount of carrier will depend upon the level of the bonding agent and any other optional ingredients that one of ordinary skill in the art would classify as distinct from the carrier (e.g., other active components). The cosmetic compositions of the present invention can comprise from about 0.01% to about 20%, about 0.05% to about 10%, about 0.1% to about 5%, and about 0.5% to about 1%, by weight of the composition or compounds of the invention.

The cosmetic compositions can be formulated in a number of ways, including but not limited to emulsions. In emulsion technology, an emulsion is a composition comprising a "dispersed phase" and a "continuous phase," with the dispersed phase existing as small particles or droplets that are suspended in and surrounded by the continuous phase. For example, suitable emulsions include oil-in-water, water-in-oil, water-in-oil-in-water, oil-in-water-in-oil, and oil-in-water-in-silicone emulsions. Preferred compositions comprise an oil-in-water emulsion.

The cosmetic compositions of the present invention can be formulated into a wide variety of product types, including creams, waxes, pastes, lotions, milks, mousses, gels, oils, tonics, and sprays. Preferred compositions are formulated into lotions, creams, gels, and sprays. These product forms may be used for a number of applications, including, but not limited to, soaps, shampoos, hair, hand and body lotions, cold creams, facial moisturizers, anti-acne preparations, topical analgesics, make-ups/cosmetics including foundations, eyeshadows, lipsticks, and the like. Any additional components required to formulate such products vary with product type and can be routinely chosen by one skilled in the art.

If compositions of the present invention are formulated as an aerosol and applied to the skin as a spray-on product, a propellant is added to the composition. Examples of suitable propellants include chlorofluorinated lower molecular weight hydrocarbons.

The cosmetic compositions of the present invention may optimally contain a variety of other components such as are conventionally used in a given product type provided that they do not unacceptably alter the benefits of the invention. These optional components should be suitable for application to mammalian skin, that is, when incorporated into the compositions they are suitable for use in contact with human skin without undue toxicity, incompatibility, instability, allergic response, and the like, within the scope of sound medical or formulator's judgment. The CTFA Cosmetic Ingredient Handbook, Second Edition (1992) describes a wide variety of nonlimiting cosmetic and pharmaceutical ingredients commonly used in the skin care industry, which are suitable for use in the compositions of the present invention. Examples of these ingredient classes include: enzymes, surfactants, abrasives, skin exfoliating agents, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents (e.g., resorcinol, sulfur, salicylic acid, erythromycin, zinc, etc.), anti-caking agents, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, polymer beads, film formers, fragrances, humectants, opacifying agents, pH adjusters, propellants, reducing agents, sequestrants, skin bleaching agents (or depigmenting, lightening agents) (e.g., hydroquinone, azelaic acid, caffeic acid, kojic acid, ascorbic acid, magnesium ascorbyl phosphate, ascorbyl glucosamine), skin soothing and/or healing agents (e.g., panthenol and derivatives (e.g., ethyl panthenol), aloe vera, pantothenic acid and its derivatives, allantoin, bisabolol, and dipotassium glycyrrhizinate), thickeners, hydrocolloids, particular zeolites, and vitamins and derivatives thereof (e.g. tocopherol, tocopherol acetate, beta carotene, retinoic acid, retinol, retinoids, retinyl palmitate, niacin, niacinamide, and the like).

Further examples of optional components include wetting agents; emollients; moisturizing agents such as glycerol, PEG 400, thiamorpholinone and derivatives thereof, or urea; anti-seborrhoea agents such as S-carboxymethylcysteine, S-benzylcysteamine, the salts and the derivatives thereof; antibiotics such as erythromycin and esters thereof, neomycin, clindamycin and esters thereof, and tetracyclines; anti-fungal agents such as ketoconazole or 4,5-polymethylene-3-isothiazolidones; agents for promoting the regrowth of the hair, such as minoxidil (2,4-diamino-5-piperidinopyridine 3-oxide) and derivatives thereof, diazoxide (7-chloro-3-methyl-1,2,4-benzothiadiazine 1,1-dioxide) and phenytoin (5,4-diphenylimidazolidine-2,4-dione); non-steroidal anti-inflammatory agents; carotenoids and, in particular, b-carotene; anti-psoriatic agents such as anthraline and derivatives thereof. The cosmetic compositions according to the invention may also contain flavor-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as butylhydroxyanisole or butylhydroxytoluene.

5.7 Controlled Release Dosage Forms

The invention also provides controlled release dosage forms comprising a compound or composition of the invention. As used herein, the terms "controlled release dosage form" and "controlled release formulation" are used interchangeably to refer to (i) formulations which create a substantially constant concentration of the drug within the body of a subject over an extended period of time, (ii) formulations which after a predetermined lag time create a substantially constant concentration of the drug within the body over an extended period of time, (iii) formulations which sustain drug action during a predetermined time period by maintaining a relatively, constant, effective drug level in the body with concomitant minimization of undesirable side effects associated with fluctuations in the plasma level of the active drug substance (e.g., a sawtooth kinetic pattern), (iv) formulations which attempt to localize drug action by, e.g., spatial placement of a controlled release composition adjacent to or in the diseased tissue or organ, and/or (v) formulations which attempt to target drug action by using carriers or chemical derivatives to deliver the drug to a particular target cell type. Controlled release formulations are also known in the art as, for example, "sustained release", "prolonged release", "programmed release", "time release", "rate-controlled" and/or "targeted release" formulations.

Nutraceutical compositions, pharmaceutical compositions, or cosmetic compositions intended to be administered as controlled release forms may be presented in any suitable dosage forms, especially in dosage forms intended for oral, parenteral, cutaneous nasal, rectal, vaginal and/or ocular administration. Such dosage forms can be used to provide controlled-release of one or more active ingredients using, for example, polymer matrices, gels, permeable membranes, osmotic systems, multilayer coatings, microparticles, nanoparticles, liposomes, microspheres, or a combination thereof to provide the desired release profile in varying proportions. Suitable controlled-release formulations known to those of ordinary skill in the art, including those described herein, can be readily selected for use with the compounds and compositions of the invention. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference.

In one embodiment, the invention encompasses single unit dosage forms suitable for oral administration such as, but not limited to, tablets, capsules, gelcaps, and caplets that are adapted for controlled-release. The dosage forms can be uncoated or they can be coated by known techniques to delay disintegration and absorption in the gastrointestinal tract, thereby providing a sustained action over a longer period. The coating can be adapted to release the active drug substance in a predetermined pattern, e.g; in order to achieve a controlled release formulation or it can be adapted not to release the active drug substance until after passage of the stomach (enteric coating). The coating can be a sugar coating, a film coating (e.g., based on hydroxypropyl methylcellulose, methylcellulose, methyl hydroxyethylcellulose, hydroxypropylcellulose, carboxymethylcellulose, acrylate copolymers (Eudragit EO), polyethylene glycols and/or polyvinylpyrrolidone) or an enteric coating (e.g. based on methacrylic acid copolymer (Eudragit* L and S), cellulose acetate phthalate, hydroxypropyl methylcellulose phthalate, hydroxypropyl metbylcellulose acetate succinate, polyvinyl acetate phthalate, shellac and/or ethylcellulose). A time delay material such as, e.g., glyceryl monostearate or glyceryl distearate can also be employed.

In a specific embodiment, a buoyant tablet formulation of the compound or composition of the invention can be prepared by granulating a mixture of the compound or composition, excipients and 20-75% w/w of hydrocolloids, such as hydroxyethylcellulose, hydroxypropylcellulose and hydroxypropylmethylcellulose. The obtained granules can then be compressed into tablets. On contact with the gastric juice, the tablet can form a substantially water-impermeable gel barrier around its surface. This gel barrier takes part in maintaining a density of less than one, thereby allowing the tablet to remain buoyant in the gastric juice.

The use of controlled release dosage forms of the invention is especially preferred in such cases where a compound or composition of the invention (i) has a narrow therapeutic index, i.e. the difference between the plasma concentration leading to harmful side effects or toxic reactions and the plasma concentration leading to a therapeutic or other beneficial effect is small; in general, the therapeutic index, TI, is defined as the ratio of median lethal dose (LD50) to median effective dose (ED50), (ii) has a narrow absorption window in the gastro-intestinal tract, (iii) has a very short biological half-live so that frequent dosing during a day is required in order to sustain the plasma level at a therapeutic level, (iv) is desired to be used only once or twice daily or even less frequent with the purpose of reducing compliance problems, and/or (v) is desired to be present in plasma without peak concentrations that is harmful or at a minimally fluctuating concentration in plasma.

Many controlled-release formulations are designed to initially release an amount of the compound or composition that promptly produces the desired therapeutic and/or beneficial effect, and gradually and continually release of other amounts of the compound or composition to maintain this level of effect over an extended period of time. In order to maintain this constant level of drug in the body, the compound or composition must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.8 Uses of the Compositions and Compounds of the Invention

Described herein are uses of the compounds and compositions of the invention for attaining a beneifical effect pertaining to proliferative disorders, inflammatory disorders and infectious diseases, attracting a beneficial effect pertaining to such diseases, or one or more symptoms thereof. The methods comprise administering to a subject in need thereof a prophylactically or therapeutically effective amount of, one or more compounds or a composition(s) of the invention. Administration of such compounds can, for example, be via one or more of the pharmaceutical compositions, nutraceutical compositions, or cosmetic compositions of the invention.

As used herein, the terms "disorder" and "disease" are used interchangeably to refer to an adverse health condition in a subject (physical and/or mental). Certain conditions may be characterized as more than one disorder. For example, certain conditions may be characterized as both non-cancerous proliferative disorders and inflammatory disorders.

As used herein, the terms "subject" and "patient" are used interchangeably herein. The terms "subject" and "subjects" refer to an animal, preferably a mammal including a non-primate and a primate (e.g., a monkey such as a cynomolgous monkey, a chimpanzee, and a human), and more preferably a human. The term "animal" also includes, but is not limited to, companion animals such as cats and dogs; zoo animals; wild animals; farm or sport animals such as ruminants, non-ruminants, livestock and fowl (e.g., horses, cattle, sheep, pigs, turkeys, ducks, and chickens); and laboratory animals, such as rodents (e.g., mice, rats), rabbits, and guinea pigs, as well as animals that are cloned or modified, either genetically or otherwise (e.g., transgenic animals).

In one embodiment, a subject in need of prevention, treatment, management, or amelioration of a disorder or a symptom thereof is a subject that has the disorder, that is known to be at risk of the disorder, has been diagnosed with the disorder, or that has previously recovered from the disorder. In particular embodiments, the subject is an animal, preferably a mammal, and more preferably a human, that is predisposed and/or at risk because of a genetic factor(s), an environmental factor(s), or a combination thereof to develop the disorder. In yet another embodiment, the subject is refractory or non-responsive to one or more other treatments for a disorder. As used herein, the terms "non-responsive" and "refractory" describe patients treated with a currently available modality (e.g., a prophylactic or therapeutic agent) for a disorder, which is not clinically adequate to relieve one or more symptoms associated with such disorder. Typically, such patients suffer from severe, persistently active disease and require additional therapy to ameliorate the symptoms associated with their disorder. In yet another embodiment, the subject is an immunocompromised or immunosuppressed mammal, such as a human.

As used herein, the terms "modality", modalities", "therapies" and "therapy" can refer to any protocol(s), method(s), and/or agent(s) that can be used in the prevention, treatment, management, or amelioration of a disorder or one or more symptoms thereof. In certain embodiments, the terms "modality", modalities", "therapy" and "therapies" refer to chemotherapy, radiation therapy, surgery, hormonal therapy, biological therapy, immunotherapy and/or other therapies useful in the prevention, management, treatment or amelioration of a disorder or one or more symptoms thereof.

As used herein, the terms "treat", "treatment" and "treating" refer to the reduction or amelioration of the progression, severity and/or duration of a disorder, or the amelioration of one or more symptoms thereof resulting from the administration of one or more modalities (e.g., one or more therapeutic agents such as a compound or composition of the invention).

As used herein, the terms "prevent," "preventing" and "prevention" refer to the prevention or inhibiting of the recurrence, onset, or development of a disorder or a symptom thereof in a subject resulting from the administration of a therapy (e.g., a prophylactic or therapeutic agent), or the administration of a combination of therapies (e.g., a combination of prophylactic or therapeutic agents).

As used herein, the terms "manage," "managing," and "management" refer to the beneficial effects that a subject derives from a therapy (e.g., a prophylactic or therapeutic agent), while not resulting in a cure of the disease. In certain embodiments, a subject is administered one or more modalities (e.g., one or more prophylactic or therapeutic agents) to "manage" a disease so as to prevent the progression or worsening of the disease. In certain embodiments the method provides a beneficial effect by lessening the discomfort associated with a disorder.

As used herein, the term "effective amount" generally refers to the amount of a compound or composition of the invention that is sufficient to reduce or ameliorate the severity, duration of a disorder or one or more symptoms thereof, prevent the advancement of a disorder, cause regression of a disorder, prevent the recurrence, development, or onset of one or more symptoms associated with a disorder, or enhance or improve the prophylactic or therapeutic effect(s) of another modality, or lessening the discomfort associated with a disorder.

As used herein, the terms "therapeutic agent" and "therapeutic agents" refer to any agent(s) which can be used in the treatment, management, or amelioration of a disorder or one or more symptoms thereof. In certain embodiments, the term "therapeutic agent" refers to a compound or composition of the invention. Therapeutic agents may be characterized as different agents based upon one or more effects the agents have in vivo and/or in vitro, for example, an anti-inflammatory agent may also be characterized as an immunomodulatory agent.

As used herein, the term "therapeutically effective amount" refers to that amount of a therapeutic agent sufficient to result in the amelioration of one or more symptoms of a disorder, prevent advancement of a disorder, cause regression of a disorder, or to enhance or improve the therapeutic effect(s) of another modality.

As used herein, the terms "prophylactic agent" and "prophylactic agents" as used refer to any agent(s) which can be used in the prevention of a disorder or one or more symptoms thereof. In certain embodiments, the term "prophylactic agent" refers to a compound or composition of the invention. Prophylactic agents may be characterized as different agents based upon one or more effects that the agents have in vitro and/or in vivo.

As used herein, the phrase "prophylactically effective amount" refers to the amount of a prophylactic agent which is sufficient to result in the prevention or inhibition of the development, recurrence or onset of a disorder or a symptom thereof, or to enhance or improve the prophylactic effect(s) of another modality (e.g., another prophylactic agent). Examples of prophylactically effective amounts of compounds are provided infra.

In a specific embodiment, with respect to the treatment of cancer, an effective amount refers to the amount of a therapeutic agent that inhibits or reduces the proliferation of cancerous cells, inhibits or reduces the spread of tumor cells (metastasis), inhibits or reduces the onset, development or progression of cancer or a symptom thereof, or reduces the size of a tumor. Preferably, a therapeutically effective amount of a therapy (e.g., a therapeutic agent) reduces the growth and/or proliferation of cancerous cells or the size or weight of a tumor by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline ("PBS").

In another embodiment, with respect to inflammation, an effective amount refers to the amount of a therapy (e.g., a therapeutic agent) that reduces the inflammation of a organ or tissue (e.g., joint, skin, stomach lining). Preferably, a therapeutically effective of a therapy (e.g., a therapeutic agent) reduces the inflammation of a organ or tissue by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%, relative to a control or placebo such as phosphate buffered saline. Examples of therapeutically effective amounts of compounds are provided infra.

In specific embodiments, such terms refer to the inhibition or reduction in the proliferation of cancerous cells, the inhibition or reduction in the spread of tumor cells (metastasis), the inhibition or reduction in the onset, development or progression of cancer or a symptom thereof, the reduction in the size of a tumor, the reduction of discomfort or pain associated with cancer, or the improvement in a patient's ECOG or Karnofsky score. In other embodiments, such terms refer to a reduction in the swelling of one or more joints, organs or tissues, or a reduction in the discomfort or pain associated with an inflammatory disorder. In other embodiments, such terms refer to a reduction in the number of infectious agents at the site of infection or in circulation, or a reduction in the symptoms, discomfort, or pain associated with an infection or an infectious disease.

The invention also provides methods for the prevention, treatment, management, or amelioration of proliferative disorders or inflammatory disorders, or one or more symptoms thereof, said methods comprising administering to a subject in need thereof a prophylactically or therapeutically effective amount of one or more compounds or a composition of the invention and a prophylactically or therapeutically effective amount of at least one other modality (e.g., at least one other prophylactic or therapeutic agent) other than a compound of the invention.

As used herein, the term "in combination" refers to the use of more than one modalities (e.g., one or more prophylactic and/or therapeutic agents). The use of the term "in combination" does not restrict the order in which modalities are administered to a subject with a disorder. A first modality (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second modality (e.g., a prophylactic or therapeutic agent such as an anti-inflammatory agent or anti-angiogenic agent) to a subject with a disorder (e.g., a proliferative disorder or an inflammatory disorder).

As used herein, the term "synergistic" refers to a combination of compounds of the invention and/or a combination of a compound, compounds or a composition of the invention and another modality (e.g., a prophylactic or therapeutic agent), including one which has been or is currently being used to prevent, manage or treat a disorder, which combination is more effective than the additive effects of the individual compounds or therapies. A synergistic effect of a combination of modalities (e.g., a combination of prophylactic or therapeutic agents) can permit the use of lower dosages of one or more of the modalities and/or less frequent administration of said modalities to a subject with a disorder. The ability to utilize lower dosages of prophylactic or therapeutic agent and/or to administer said agent less frequently can reduce the toxicity associated with the administration of said agent to a subject without reducing the efficacy of said agent in the prevention, management or treatment of a disorder. In addition, a synergistic effect can result in improved efficacy of agents in the prevention, management or treatment of a disorder. Moreover, a synergistic effect of a combination of prophylactic or therapeutic agents can avoid or reduce adverse or unwanted side effects associated with the use of either therapy alone.

As used herein, the phrase "side effects" encompasses unwanted, and adverse effects of a modality. Side effects are always unwanted, but unwanted effects are not necessarily adverse. An adverse effect might be harmful, uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra pyramidal symptoms, akathisia, cardiovascular disturbances and sexual dysfunction.

5.8.1 Proliferative Disorders

The compounds of the invention and compositions comprising said compounds can be used to prevent, treat, manage, or ameliorate a proliferative disorder or one or more symptoms thereof. The present invention provides methods for preventing, treating, managing, or ameliorating one or more symptoms of a non-cancerous disorder associated with cellular hyperproliferation, particularly of epithelial cells (e.g., as in asthma, COPD, pulmonary fibrosis, bronchial hyperresponsiveness, psoriasis, lymphoproliferative disorder, and seborrheic dermatitis), and endothelial cells (e.g., as in restenosis, hyperproliferative vascular disease, Behcet's Syndrome, atherosclerosis, and macular degeneration), said methods comprising administering to a subject in need thereof one or more compounds of the invention. The present invention also provides methods for preventing, managing, treating, or ameliorating a non-cancerous disorder associated with cellular hyperproliferation, said methods comprising of administering to a subject in need thereof one or more compounds or compositions of the invention and one or more other therapies (e.g., one or more other prophylactic or therapeutic agents) useful for the prevention, treatment, management, or amelioration of said disorder.

In a specific embodiment, the invention provides methods for preventing, managing, treating, or ameliorating a non-cancerous disorder associated with cellular hyperproliferation (e.g., Behcet's Syndrome, sarcoidosis, keloids, pulmonary fibrosis, and renal fibrosis) or one or more symptoms thereof, said methods comprising of administering to a subject in need thereof a prophylactically or therapeutically effective amount of one or more compounds of the invention. In another embodiment, the invention provides methods for preventing, managing, treating, or ameliorating a non-cancerous disorder associated with cellular hyperproliferation (e.g., Behcet's Syndrome, sarcoidosis, keloids, pulmonary fibrosis, renal and fibrosis) or one or more symptoms thereof, said methods comprising of administering to a subject in need thereof a prophylactically or therapeutically effective amount of one or more compounds of the invention and a prophylactically or therapeutically effective amount of one or more other therapies (e.g., one or more prophylactic or therapeutic agents).

The invention encompasses methods for preventing, treating, managing, or ameliorating one or more symptoms of a disorder associated with cellular hyperproliferation in a subject refractory to conventional therapies for such disorder, said methods comprising contacting with or administering to subject a dose of a prophylactically or therapeutically effective amount of one or more compounds of the invention. The present invention also provides methods for preventing, managing, treating, or ameliorating a non-cancerous disorder associated with cellular hyperproliferation in a subject refractory to conventional therapies for such disorder, said methods comprising of administering to a subject in need thereof one or more compounds of the invention and one or more other therapies (e.g., one or more other prophylactic or therapeutic agents) useful for the prevention, treatment, management, or amelioration of said disorder.

In a specific embodiment, the invention provides a method of preventing, treating, managing, or ameliorating a cancer or one or more symptoms thereof, said method comprising administering to a subject in need thereof a dose of a prophylactically or therapeutically effective amount of one or more compounds of the invention. In another embodiment, the invention provides a method of preventing, treating, managing, or ameliorating cancer or one or more symptoms thereof, said method comprising administering to a subject in need thereof a dose of a prophylactically or therapeutically effective amount of one or more compounds of the invention and a dose of a prophylactically or therapeutically effective amount of one or more therapies (e.g., one or more prophylactic or therapeutic agents) useful for the prevention, treatment, management, or amelioration of cancer, or a secondary condition (e.g., a viral, bacterial, or fungal infection).

The compounds of the invention can be used in an in vitro or ex vivo fashion for the management, treatment or amelioration of certain cancers, including, but not limited to leukemias and lymphomas, such treatment involving autologous stem cell transplants. This can involve a multi-step process in which the subject's autologous hematopoietic stem cells are harvested and purged of all cancer cells, the patient's remaining bone-marrow cell population is then eradicated via the administration of a high dose of a compound of the invention with or without accompanying high dose radiation therapy, and the stem cell graft is infused back into the subject. Supportive care is then provided while bone marrow function is restored and the subject recovers.

One or more of the compounds of the invention may be used as a first, second, third, fourth, fifth or more line of cancer therapy. The invention provides methods for preventing, treating, managing, or ameliorating cancer or one or more symptoms thereof in a subject refractory to conventional therapies for such a cancer, said methods comprising administering to said subject a dose of a prophylactically or therapeutically effective amount of one or more compounds of the invention. A cancer may be determined to be refractory to a therapy means when at least some significant portion of the cancer cells are not killed or their cell division arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory when the number of cancer cells has not been significantly reduced, or has increased.

The invention provides methods for preventing, managing, treating or ameliorating cancer or one or more symptoms thereof in a subject refractory to existing single agent therapies for such a cancer, said methods comprising administering to said subject a dose of a prophylactically or therapeutically effective amount of one or more compounds of the invention and a dose of a prophylactically or therapeutically effective amount of one or more therapies (e.g., one or more prophylactic or therapeutic agents) useful for the prevention, treatment, management, or amelioration of cancer or a secondary condition. The invention also provides methods for preventing, treating, managing, or ameliorating cancer or a secondary condition by administering one or more compounds of the invention in combination with any other therapy(ies) (e.g., radiation therapy, chemotherapy or surgery) to patients who have proven refractory to other treatments but are no longer on this therapy(ies).

The invention provides methods for the prevention, treatment, management, or amelioration of a patient having cancer and immunosuppressed by reason of having previously undergone other cancer therapies. The invention also provides alternative methods for the prevention, treatment, management, or amelioration of cancer where chemotherapy, radiation therapy, hormonal therapy, and/or biological therapy/immunotherapy has proven or may prove too toxic, i.e., results in unacceptable or unbearable side effects, for the subject being treated. Further, the invention provides methods for preventing the recurrence of cancer in patients that have been treated and have no disease activity by administering one or more compounds of the invention.

In a specific embodiment, the cancer that is being prevented, managed, treated or ameliorated in accordance with the method of the invention is skin cancer, prostate cancer, breast cancer, bone cancer, melanoma, lung cancer and ovarian cancer. In another embodiment, the cancer that is being prevented, managed, treated or ameliorated in accordance with the methods of the invention are metastatic tumors including, but not limited to, tumors that have or may metastasize to the bone (non-limiting examples are prostate, breast and lung cancers that have metastasized or have the potential to metastasize to the bone), tumors that have or may metastasize to the lung, tumors that have or may metastasize to the brain, and tumors that have or may metastasize to other organs or tissues of a subject.

Cancers that can also be prevented, managed, treated or ameliorated in accordance with the methods of the invention include, but are not limited to, neoplasms, tumors (malignant and benign) and metastases, or any disease or disorder characterized by uncontrolled cell growth. The cancer may be a primary or metastatic cancer. Specific examples of cancers that can be prevented, managed, treated or ameliorated in accordance with the methods of the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

5.8.2 Inflammatory Disorders

One or more compounds and/or compositions of the invention can be used to prevent, treat, manage, relieve, or ameliorate an inflammatory disorder or one or more symptoms thereof. The compounds of the invention or compositions comprising said compounds may also be administered in combination with one or more other therapies (e.g., one or more other prophylactic or therapeutic agents) useful for the prevention, treatment, management, or amelioration of a condition associated with inflammation (in particular, an inflammatory disorder) or one or more symptoms thereof.

The compounds or compositions of the invention can be used to prevent, reduce, or eliminate one or more symptoms and/or conditions associated with inflammation, for examples, redness, excess warmth, edema (swelling), and/or pain associated with inflammation can be prevented, reduced or eliminated.

In a specific embodiment, the invention provides a method of preventing, treating, managing, or ameliorating a condition associated with inflammation (e.g., an inflammatory disorder) or one or more symptoms thereof, said method comprising contacting with or administering to a subject in need thereof a dose of a prophylactically or therapeutically effective amount one or more compounds of the invention. In another embodiment, the invention provides a method of preventing, treating, managing, or ameliorating a condition associated with inflammation (e.g., an inflammatory disorder) or one or more symptoms thereof, said method comprising administering to a subject in need thereof a dose of a prophylactically or therapeutically effective amount of one or more of compounds of the invention and a dose of a prophylactically or therapeutically effective amount of one or more other therapies (e.g., one or more other prophylactic or therapeutic agents).

The invention provides methods for preventing, managing, treating or ameliorating a condition associated with inflammation (e.g., an inflammatory disorder) or one or more symptoms thereof in a subject refractory to conventional therapies (e.g., methotrexate and a TNF-α antagonist (e.g., REMICADE™ or ENBREL™)) for such condition, said methods comprising administering to said subject a dose of a prophylactically or therapeutically effective amount of one or more compounds of the invention. The invention also provides methods for preventing, treating, managing, or ameliorating a condition associated with inflammation (e.g., an inflammatory disorder) or one or more symptoms thereof in a subject refractory to existing single agent therapies for such a condition, said methods comprising administering to said subject a dose of a prophylactically or therapeutically effective amount of one or more compounds of the invention and a dose of a prophylactically or therapeutically effective amount of one or more other therapies (e.g., one or more other prophylactic or therapeutic agents). The invention also provides methods for preventing, treating, managing, or ameliorating a condition associated with inflammation (e.g., an inflammatory disorder) by administering one or more compounds of the invention in combination with any other therapy(ies) to patients who have proven refractory to other treatments but are no longer on this therapy(ies). The invention also provides alternative methods for the prevention, treatment, management, or amelioration of a condition associated with inflammation (e.g., an inflammatory disorder) where another therapy has proven or may prove too toxic, i.e., results in unacceptable or unbearable side effects, for the subject being treated. Further, the invention provides methods for preventing the recurrence of a condition associated with inflammation (e.g., an inflammatory disorder) in patients that have been treated and have no disease activity by administering one or more compounds of the invention.

Examples of the inflammatory disorders which can be prevented, managed, treated, or ameliorated in accordance with the methods of the invention, include, but are not limited to, asthma, allergic reactions, allergic disorders, inflammatory disorders characterized by type-1 mediated inflammation, inflammatory disorders characterized by type-2 mediated inflammation, fibrotic disease (e.g., pulmonary fibrosis), psoraisis, multiple sclerosis, systemic lupus erythrematosis, chronic obstructive pulmonary disease (COPD), encephilitis, inflammatory bowel disease (e.g., Crohn's disease and ulcerative colitis), ischemic reperfusion injury, Gout, Behcet's disease, septic shock, undifferentiated spondyloarthropathy, undifferentiated arthropathy, arthritis, rheumatoid arthritis juvenile and adult), osteoarthritis, psoriatic arthritis, inflammatory osteolysis, systemic inflamatory response syndrome (SIRS), sepsis, meningitis, and chronic inflammation resulting from chronic viral or bacteria infections.

In a specific embodiment, the inflammatory disorder which is prevented, treated, managed, or ameliorated in accordance with the methods of the invention is an inflammatory disorder characterized as a type 2-mediated inflammation. Type 2-mediated inflammation is characterized by eosinophilic and basophilic tissue infiltration and/or extensive mast cell degranulation, a process dependent on cross-linking of surface-bound IgE. In another embodiment, the inflammatory disorder which is prevented, treated, managed, or ameliorated in accordance with the methods of the invention is asthma, Behcet's disease, arthritis, chronic obstructive pulmonary disease (COPD), pulmonary fibrosis, renal fibrosis, Gout or allergic disorders.

In a specific embodiment, an effective amount of one or more compounds of the invention is administered to a subject in combination with an effective amount of one or more therapies (e.g., prophylactic or therapeutic agents) useful in preventing, treating, managing, or ameliorating asthma or one or more symptoms thereof. Non-limiting examples of such theapies include, but are not limited to, adrenergic stimulants (e.g., catecholamines (e.g., epinephrine, isoproterenol, and isoetharine), resorcinols (e.g., metaproterenol, terbutaline, and fenoterol), saligenins (e.g. salbutamol)), anticholinergics (e.g.,atropine sulfate, atropine methylnitrate, and ipratropium bromide (ATROVENT™)), beta2-agonists (e.g.abuterol (VENTOLIN™ and PROVENTIL™), bitolterol (TORNALATE™), levalbuterol (XOPONEX™), metaproterenol (ALUPENT™), pirbuterol (MAXAIR™), terbutlaine (BRETHAIRE™ and BRETHINE™), albuterol (PROVENTIL™, REPETABS™, and VOLMAX™), formoterol (FORADIL AEROLIZER™), and salmeterol (SEREVENT™ and SEREVENT DISKUS™)), corticosteroids (e.g., methlyprednisolone (MEDROL™), prednisone (PREDNISONE™ and DELTASONE™), and prednisolone (PRELONE™, PEDIAPRED™)), glucocorticoids (e.g. oral steroids or other systemic or oral steroids, and inhaled gucocoritcoids), other steroids, immunosuppressant agents (e.g. methotrexate and gold salts), leukotriene modifiers (e.g., montelukast (SINGULAIR™), zafirlukast (ACCOLATE™), and zileuton (ZYFLO™)), mast cell stabilizers (e.g., cromolyn sodium (INTAL™) and nedocromil sodium (TILADE™)), methylxanthines (e.g., theophylline (UNIPHYL™, THEO-DUR™, SLO-BID™, AND TEHO-42™)), and mucolytic agents (e.g., acetylcysteine)).

In a specific embodiment, an effective amount of one or more compounds of the invention is administered to a subject in combination with an effective amount of one or more therapies (e.g., prophylactic or therapeutic agents) useful in preventing, treating, managing, or ameliorating allergies or one or more symptoms thereof. Non-limiting examples of therapies include antimediator drugs (e.g., antihistamine, see Table 2), corticosteroids, decongestants, sympathomimetic drugs (e.g., α-adrenergic and β-adrenergic drugs), theophylline and its derivatives, glucocorticoids, and immunotherapies (e.g., repeated long-term injection of allergen, short course desensitization, and venom immunotherapy).

TABLE 2

| H₁ ANTIHISTAMINES | |
|---|---|
| Chemical class and representative drugs | Usual daily dosage |
| Ethanolamine | |
| Diphehydramine | 25-50 mg every 4-6 hours |
| Clemastine | 0.34-2.68 mg every 12 hours |
| Ethylenediamine | |
| Tripelennamine | 25-50 mg every 4-6 hours |
| Alkylamine | |
| Brompheniramine | 4 mg every 4-6 hours; or 8-12 mg of SR form every 8-12 hour |
| Chlorpheniramine | 4 mg every 4-6 hours; or 8-12 mg of SR form every 8-12 hour |
| Triprolidine (1.25 mg/5 ml) | 2.5 mg every 4-6 hours |

TABLE 2-continued

| H₁ ANTIHISTAMINES | |
|---|---|
| Chemical class and representative drugs | Usual daily dosage |
| Phenothiazine | |
| Promethazine | 25 mg at bedtime |
| Piperazine | |
| Hydroxyzine | 25 mg every 6-8 hours |
| Piperidines | |
| Astemizole (nonsedating) | 10 mg/d |
| Azatadine | 1-2 mg every 12 hours |
| Cetirzine | 10 mg/d |
| Cyproheptadine | 4 mg every 6-8 hour |
| Fexofenadine (nonsedating) | 60 mg every 12 hours |
| Loratidine (nonsedating) | 10 mg every 24 hours |

In a specific embodiment, an effective amount of one or more compounds of the invention is administered to a subject in combination with an effective amount of one or more therapies (e.g., prophylactic or therapeutic agents) useful in preventing, treating, managing, or ameliorating COPD or one or more symptoms thereof. Non-limiting examples of such therapies include, but are not limited to, bronchodilators (e.g. short-acting $\beta_2$-adrenergic agonist (e.g., albuterol, pirbuterol, terbutaline, and metaproterenol), long-acting $\beta_2$-adrenergic agonists (e.g., oral sustained-release albuterol and inhaled salmeterol), anticholinergics (e.g., ipratropium bromide), and theophylline and its derivatives (therapeutic range for theophylline is preferably 10-20 µg/mL)), glucocorticoids, exogenous $\alpha_1 AT$ (e.g., $\alpha_1 AT$ derived from pooled human plasma administered intravenously in a weekly dose of 60 mg/kg ), oxygen, lung transplantation, lung volume reduction surgery, endotracheal intubation, ventilation support, yearly influenza vaccine and pneumococcal vaccination with 23-valent polysaccharide, exercise, and smoking cessation.

In a specific embodiment, an effective amount of one or more compounds of the invention is administered to a subject in combination with an effect amount of one or more therapies (e.g., prophylactic or therapeutic agents) useful in preventing, treating, managing, or ameliorating pulmonary fibrosis or one or more symptoms thereof. Non-limiting examples of such theapies include, oxygen, corticosteroids (e.g., daily administration of prednisone beginning at 1-1.5 mg/kg/d (up to 100 mg/d) for six weeks and tapering slowly over 3-6 months to a minimum maintenance dose of 0.25 mg/kg/d), cytotoxic drugs (e.g., cyclophosphamide at 100-120 mg orally once daily and azathioprine at 3 mg/kg up to 200 mg orally once daily), bronchodilators (e.g., short- and long-acting β2-adrenergic agonists, anticholinergics, and theophylline and its derivatives), and antihistamines (e.g., diphenhydramine and doxylamine). Anti-inflammatory therapies and their dosages, routes of administration and recommended usage are known in the art and have been described in such literature as the Physician's Desk Reference (58th ed., 2004).

5.8.3 Infectious Diseases

One or more compounds or compositions of the invention can be used to prevent, treat, manage, relieve, or ameliorate an infectious disease or one or more symptoms thereof. The compounds or compositions of the invention can also be administered in combination with one or more other therapies (e.g., one or more other prophylactic or therapeutic agents) useful for the prevention, treatment, management, or amelioration of a condition associated with an infectious disease or one or more symptoms thereof.

Infectious viruses of both human and non-human vertebrates, include retroviruses, RNA viruses and DNA viruses. Examples of virus that have been found in humans include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picomaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Retroviruses that are contemplated include both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Reoviridae, including the genus *Orthoreovirus* (multiple serotypes of both mammalian and avian retroviruses), the genus *Orbivirus* (Bluetongue virus, Eugenangee virus, Kemerovo virus, African horse sickness virus, and Colorado Tick Fever virus), the genus *Rotavirus* (human rotavirus, Nebraska calf diarrhea virus, murine rotavirus, simian rotavirus, bovine or ovine rotavirus, avian rotavirus); the family Picomaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus *Cardiovirus* (Encephalomyocarditis virus (EMC), Mengovirus), the genus *Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, Feline picornavirus and Norwalk virus; the family Togaviridae, including the genus *Alphavirus* (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever, virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), Chandipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxviridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A,B,C,D,E and ungrouped; simian adenoviruses (at least 23 serotypes), infectious canine hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, the genus *Parvovirus* (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents.

Bacterial infections or diseases that can be treated or prevented by the methods of the present invention are caused by bacteria including, but not limited to, bacteria that have an intracellular stage in its life cycle, such as mycobacteria (e.g., *Mycobacteria tuberculosis, M. bovis, M. avium, M. leprae*, or *M. africanum*), rickettsia, mycoplasma, chlamydia, and legionella. Other examples of bacterial infections contemplated include but are not limited to infections caused by Gram positive bacillus (e.g., *Listeria, Bacillus* such as *Bacillus anthracis, Erysipelothrix* species), Gram negative bacillus (e.g., *Bartonella, Brucella, Campylobacter, Enterobacter, Escherichia, Francisella, Hemophilus, Klebsiella, Morganella, Proteus, Providencia, Pseudomonas, Salmonella, Serratia, Shigella, Vibrio*, and *Yersinia* species), spirochete bacteria (e.g., *Borrelia* species including *Borrelia burgdorferi* that causes Lyme disease), anaerobic bacteria (e.g., *Actinomyces* and *Clostridium* species), Gram positive and negative coccal bacteria, *Enterococcus* species, *Streptococcus* species, *Pneumococcus* species, *Staphylococcus* species, *Neisseria* species. Specific examples of infectious bacteria include but are not limited to: *Helicobacter pyloris, Borelia burgdorferi, Legionella pneumophilia, Mycobacteria tuberculosis, M. avium, M. intracellulare, M. kansaii, M. gordonae, Staphylococcus aureus, Neisseria gonorrhoeae, Neisseria meningitidis, Listeria monocytogenes, Streptococcus pyogenes* (Group A Streptococcus), *Streptococcus agalactiae* (Group B Streptococcus), *Streptococcus viridans, Streptococcus faecalis, Streptococcus bovis, Streptococcus pneumoniae, Haemophilus influenzae, Bacillus antracis, corynebacterium diphtheriae, Erysipelothrix rhusiopathiae, Clostridium perfringers, Clostridium tetani, Enterobacter aerogenes, Klebsiella pneumoniae, Pasturella multocida, Fusobacterium nucleatum, Streptobacillus moniliformis, Treponema pallidium, Treponema pertenue, Leptospira, Rickettsia*, and *Actinomyces israeli*.

Fungal infections or conditions resulting from or associated with a fungal infection (e.g., a respiratory infection) can be prevented, treated, managed, and/or ameliorated in accordance with the methods of invention. Examples of fungus which cause fungal infections include, but not limited to, *Absidia* species (e.g., *Absidia corymbifera* and *Absidia ramosa*), *Aspergillus* species, (e.g., *Aspergillus flavus, Aspergillusfumigatus, Aspergillus nidulans, Aspergillus niger*, and *Aspergillus terreus*), *Basidiobolus ranarum, Blastomyces dermatitidis, Candida* species (e.g., *Candida albicans, Candida glabrata, Candida kerr, Candida krusei, Candida parapsilosis, Candida pseudotropicalis, Candida quillermondii, Candida rugosa, Candida stellatoidea*, and *Candida tropicalis*), *Coccidioides immitis, Conidiobolus* species, *Cryptococcus neoforms, Cunninghamella* species, dermatophytes, *Histoplasma capsulatum, Microsporum gypseum, Mucor pusillus, Paracoccidioides brasiliensis, Pseudallescheria boydii, Rhinosporidium seeberi, Pneumocystis carinii, Rhizopus* species (e.g., *Rhizopus arrhizus, Rhizopus oryzae*, and *Rhizopus microsporus*), *Saccharomyces* species, *Sporothrix schenckii*, zygomycetes, and classes such as Zygomycetes, Ascomycetes, the Basidiomycetes, Deuteromycetes, and Oomycetes. In addition, fungal diseases that can be treated or prevented by the methods of the present invention include but not limited to aspergilliosis, crytococcosis, sporotrichosis, coccidioidomycosis, paracoccidioidomycosis, histoplasmosis, blastomycosis, zygomycosis, and candidiasis.

Parasitic diseases that can be treated or prevented by the methods of the present invention including, but not limited to, amebiasis, malaria, leishmania, coccidia, giardiasis, cryptosporidiosis, toxoplasmosis, and trypanosomiasis. Also encompassed are infections by various worms, such as but not limited to ascariasis, ancylostomiasis, trichuriasis, strongyloidiasis, toxoccariasis, trichinosis, onchocerciasis. filaria, and dirofilariasis. Also encompassed are infections by various flukes, such as but not limited to schistosomiasis, paragonimiasis, and clonorchiasis. Parasites that cause these diseases can be classified based on whether they are intracellular or extracellular. An "intracellular parasite" as used herein is a parasite whose entire life cycle is intracellular. Examples of human intracellular parasites include *Leishmania* spp., *Plasmodium* spp., *Trypanosoma cruzi, Toxoplasma*

*gondii, Babesia* spp., and *Trichinella spiralis*. An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "Obligate intracellular parasites". These parasites may exist most of their lives or only a small portion of their lives in an extracellular environment, but they all have at least one obligate intracellular stage in their life cycles. This latter category of parasites includes *Trypanosoma rhodesiense* and *Trypanosoma gambiense, Isospora* spp., *Cryptosporidium* spp, *Eimeria* spp., *Neospora* spp., *Sarcocystis* spp., and *Schistosoma* spp.

5.9 Agents Useful In Combination With the Compounds of the Invention

The present invention provides methods for preventing, managing, treating, or ameliorating a disorder (e.g., proliferative disorders or inflammatory disorders) using a compound or composition of the invention in combination with another modality, such as a prophylactic or therapeutic agent known to be useful for, or having been or currently being used in the prevention, treatment, management, or amelioration of a disorder or used in the lessening of discomfort or pain associated with a disorder. Depending on the manner of use, the compositions or compounds of the invention can be co-administered with another modality, or the compositions or compounds of the invention can be mixed and then administered as a single composition to a subject.

In one embodiment, one or more compound(s) of the invention or a composition of the invention can be added to an over-the-counter, non-prescriptional medication. Examples of such medication include but are not limited to an analgesic, acetaminophen, non-steroidal anti-inflammatory agent, salicylate, antibiotic, antidiarrheal, antihelmintic, antiemetic, antiflatulent, antifungal, antihistamine, antitussive, antimycotic, antacid, antipruritics, antipyretics, decongestant, expectorant, laxative, hemorrhoidal preparation, artificial tear, sedative, motion sickness medication, acne medication, sebborrhea medication, bum preparation, canker sore preparation, steorid, sore throat lozenge, smoke cessation aid, and wound care product.

Therapeutic or prophylactic agents include, but are not limited to, plant extracts, small molecules, synthetic drugs, peptides, polypeptides, proteins, nucleic acids (e.g., DNA and RNA nucleotides including, but not limited to, antisense nucleotide sequences, RNAi, triple helices and nucleotide sequences encoding biologically active proteins, polypeptides or peptides), antibodies, synthetic or natural inorganic molecules, mimetic agents, and synthetic or natural organic molecules. In a specific embodiment, a composition comprises one, two, three, four or more compounds of the invention, or a pharmaceutically acceptable salt, solvate, or hydrate thereof, and one, two, three, four or more immunomodulatory agents. In another embodiment, a composition comprises one, two, three, four or more compounds of the invention, or a pharmaceutically acceptable salt, solvate, or hydrate thereof, and one, two, three, four or more anti-angiogenic agents. In yet another embodiment, a composition comprises one, two, three, four or more compounds of the invention, or a pharmaceutically acceptable salt, solvate, or hydrate thereof, and one, two, three, four or more anti-inflammatory agents. In another embodiment, a composition comprises one, two, three, four or more compounds of the invention, or a pharmaceutically acceptable salt, solvate, or hydrate thereof, and one, two, three, four or more anti-cancer agents. In another embodiment, a composition comprises one, two, three, four or more compounds of the invention, or a pharmaceutically acceptable salt, solvate, or hydrate thereof, and one, two, three, four or more anti-viral agents. In another embodiment, a composition comprises one, two, three, four or more compounds of the invention, or a pharmaceutically acceptable salt, solvate, or hydrate thereof, and one, two, three, four or more one or more antibiotics. In another embodiment, a composition comprising one, two, three, four or more compounds of the invention, or a pharmaceutically acceptable salt, solvate, or hydrate thereof, or one or more natural products, phytochemicals, or botanical extracts. In yet another embodiment, a composition comprises one, two, three, four or more compounds of the invention, or a pharmaceutically acceptable salt, solvate, or hydrate thereof, and any combination of one, two, three, or more of each of the following prophylactic or therapeutic agents: an immunomodulatory agent, an anti-angiogenic agent, a botantical extract, an anti-cancer agent, an immunomodulatory agent, anti-angiogenic agent, an anti-inflammatory agent, an anti-viral agent, or an antibacterial agent (e.g., an antibiotic).

Any agent which contributes to the prevention, management, treatment, or amelioration of a disorder (e.g., a proliferative disorder or an inflammatory disorder) or one or more symptoms thereof can be used in combination with a compound of the invention in accordance with the invention described herein. See, e.g., Gilman et al., Goodman and Gilman's: The Pharmacological Basis of Therapeutics, Tenth Ed., McGraw-Hill, New York, 2001; The Merck Manual of Diagnosis and Therapy, Berkow, M.D. et al. (eds.), 17th Ed., Merck Sharp & Dohme Research Laboratories, Rahway, N.J., 1999; Cecil Textbook of Medicine, 20th Ed., Bennett and Plum (eds.), W.B. Saunders, Philadelphia, 1996 for information regarding prophylactic or therapeutic agents which have been or are currently being used for preventing, treating, managing, or ameliorating proliferative disorders or inflammatory disorders or one or more symptoms thereof. Examples of such agents include, but are not limited to, anti-inflammatory agents (e.g., corticosteroids (e.g., prednisone and hydrocortisone), glucocorticoids, steroids, non-steriodal anti-inflammatory drugs (e.g., aspirin, ibuprofen, diclofenac, and COX-2 inhibitors), beta-agonists, anticholinergic agents and methyl xanthines), immunomodulatory agents, gold injections, sulphasalazine, penicillamine, anti-angiogenic agents (e.g., angiostatin, TNF-α antagonists (e.g., anti-TNFα antibodies), and endostatin), anti-fibrotics, antiemetic agents (e.g., metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine and tropisetron), opioids (e.g., morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone and propoxyphene), hematopoietic colony stimulating factors (e.g., filgrastim, pegfilgrastim sargramostim, molgramostim and epoetin alfa), antiemetic agents (e.g., metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxypemdyl, pipamazine, scopolamine, sulpiride, tetrahydrocannabinols, thiethylperazine, thioproperazine and tropisetron), dapsone, psoralens (e.g., methoxalen and trioxsalen), antihistamines, anti-malarial agents (e.g., hydroxychloroquine), anti-viral agents, and antibiotics (e.g., dactinomycin (formerly actinomycin), bleomycin, erythomycin, penicillin, mithramycin, and anthramycin (AMC)).

5.9.1 Immunodulatory Agents

Any immunomodulatory agent can be used in the methods and compositions of the invention. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, monocyte and/or basophil counts, and the cellular communication among cells of the immune system. In certain embodiments of the invention, an immunomodulatory agent modulates one aspect of the immune response. In other embodiments, an immunomodulatory agent modulates more than one aspect of the immune response. In a preferred embodiment of the invention, the administration of an immunomodulatory agent to a subject inhibits or reduces one or more aspects of the subject's immune response capabilities. In a specific embodiment of the invention, the immunomodulatory agent inhibits or suppresses the immune response in a subject. In accordance with the invention, an immunomodulatory agent is not a compound of the invention. In certain embodiments, an immunomodulatory agent is not an anti-inflammatory agent. In other embodiments, an immunomodulatory agent is not an anti-angiogenic agent. In yet other embodiments, an immunomodulatory agent is not a TNF-α antagonist.

In certain embodiments, an immunomodulatory agent is a chemotherapeutic agent. In other embodiments, an immunomodulatory agent is not a chemotherapeutic agent.

Examples of immunomodulatory agents are well known to those of skill in the art and can include, but are not limited to, proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules, triple helices and nucleic acid molecules encoding immunomodulatory gene products), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

As used herein, the terms "antibody" and "antibodies" refer to molecules that contain an antigen binding site, e.g., immunoglobulins. Immunoglobulin molecules can be of any type (e.g., IgG, IgE, IgM, IgD, IgA and IgY), class (e.g., $IgG_1$, $IgG_2$, $IgG_3$, $IgG_4$, IgA, and $IgA_2$) or subclass. Antibodies include, but are not limited to, monoclonal antibodies, multispecific antibodies, human antibodies, humanized antibodies, camelised antibodies, chimeric antibodies, single domain antibodies, single chain Fvs (scFv), single chain antibodies, Fab fragments, F(ab') fragments, disulfide-linked Fvs (sdFv), and anti-idiotopic (anti-Id) antibodies (including, e.g., anti-Id antibodies to antibodies of the invention), and epitope-binding fragments of any of the above.

As used herein, the term "T cell receptor modulator" refers to an agent which modulates the phosphorylation of a T cell receptor, the activation of a signal transduction pathway associated with a T cell receptor, and/or the expression of a particular protein such as a cytokine. Such an agent may directly or indirectly modulate the phosphorylation of a T cell receptor, the activation of a signal transduction pathway associated with a T cell receptor, and/or the expression of a particular protein such as a cytokine. Thus, examples of T cell receptor modulators include, but are not limited to, peptides, polypeptides, proteins, fusion proteins and antibodies which immunospecifically bind to a T cell receptor or a fragment thereof. Further, examples of T cell receptor modulators include, but are not limited to, proteins, peptides, polypeptides (e.g., soluble T cell receptors), fusion proteins and antibodies that immunospecifically binds to a ligand for a T cell receptor or a fragment thereof. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114) (IDEC))), CTLA4-immunoglobulin, and LFA-3TIP (Biogen, International Publication No. WO 93/08656 and U.S. Pat. No. 6,162,432).

As used herein, the term "cytokine receptor modulator" refers to an agent which modulates the phosphorylation of a cytokine receptor, the activation of a signal transduction pathway associated with a cytokine receptor, and/or the expression of a particular protein such as a cytokine. Such an agent may directly or indirectly modulate the phosphorylation of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins and antibodies that immunospecifically binds to a cytokine receptor or a fragment thereof. Further, examples of cytokine receptor modulators include, but are not limited to, peptides, polypeptides (e.g., soluble cytokine receptors), fusion proteins and antibodies that immunospecifically binds to a cytokine or a fragment thereof. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL12, IL-15, IL-23 TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, anti-IL-12 receptor antibodies, anti-IL-15 receptor antibodies and anti-IL-23 receptor antibodies), anti-cytokine antibodies (e.g., anti-IFNα antibodies, anti-IFN-β antibodies, anti-IFN-γ antibodies, anti-TNF-α antibodies, anti-IL-11 antibodies, anti-IL-2 antibodies, anti-IL-4 antibodies, anti-IL-6 antibodies, anti-IL-8 antibodies (e.g., ABX-IL-8 (Abgenix)), anti-IL-9 antibodies, anti-IL-10 antibodies, anti-IL-12 antibodies and anti-IL-23 antibodies). In a specific embodiment, a cytokine receptor modulator is IL-4, IL-10, or a fragment thereof. In another embodiment, a cytokine receptor modulator is an anti-IL-10 antibody, anti-IL-6 antibody, anti-IL-12 receptor antibody, or anti-TNF-α antibody. In another embodiment, a cytokine receptor modulator is the extracellular domain of a TNF-α receptor or a fragment thereof. In certain embodiments, a cytokine receptor modulator is not a TNF-α antagonist.

An immunomodulatory agent may be selected to interfere with the interactions between the T helper subsets (TH1 or TH2) and B cells to inhibit neutralizing antibody formation. An immunomodulatory agent may also be selected to inhibit the interaction between TH1 cells and cytoxic T cells (CTLs) to reduce the occurrence of CTL-mediated killing. Further, an immunomodulatory agent may be selected to alter (e.g., inhibit or suppress) the proliferation, differentiation, activity and/or function of the $CD4^+$ and/or $CD8^+$ T cells. For example, antibodies specific for T cells can be used as immunomodulatory agents to deplete, or alter the proliferation, differentiation, activity and/or function of $CD4^+$ and/or $CD8^+$ T cells.

In one embodiment of the invention, an immunomodulatory agent that reduces or depletes T cells, preferably memory T cells, is administered to a subject with a proliferative disorder or an inflammatory disorder in accordance with the methods of the invention. See, e.g., U.S. Pat. No. 4,658,019. In another embodiment of the invention, an immunomodulatory agent that inactivates $CD8^+$ T cells is administered to a subject with a proliferative disorder or an inflammatory disorder in accordance with the methods of the invention. In a specific embodiment, anti-CD8 antibodies are used to reduce or deplete $CD8^+$ T cells.

Antibodies that interfere with or block the interactions necessary for the activation of B cells by TH (T helper) cells, and thus block the production of neutralizing antibodies, are useful as immunomodulatory agents in accordance the methods of the invention. For example, B cell activation by T cells requires certain interactions to occur (Durie et al, Immunol. Today, 15(9):406-410 (1994)), such as the binding of CD40 ligand on the T helper cell to the CD40 antigen on the B cell, and the binding of the CD28 and/or CTLA4 ligands on the T cell to the B7 antigen on the B cell. Without both interactions, the B cell cannot be activated to induce production of the neutralizing antibody.

The CD40 ligand (CD40L)-CD40 interaction is a desirable point to block the immune response because of its broad activity in both T helper cell activation and function as well as the absence of redundancy in its signaling pathway. Thus, in a specific embodiment of the invention, the interaction of CD40L with CD40 is transiently blocked at the time of administration of one or more of the immunomodulatory agents. This can be accomplished by treating with an agent which blocks the CD40 ligand on the TH cell and interferes with the normal binding of CD40 ligand on the T helper cell with the CD40 antigen on the B cell. An antibody to CD40 ligand (anti-CD40L) (available from Bristol-Myers Squibb Co; see, e.g., European patent application 555,880, published Aug. 18, 1993) or a soluble CD40 molecule can be selected and used as an immunomodulatory agent in accordance with the methods of the invention.

In another embodiment, an immunomodulatory agent which reduces or inhibits one or more biological activities (e.g., the differentiation, proliferation, and/or effector functions) of TH0, TH 1, and/or TH2 subsets of CD4+T helper cells is administered to a subject with an inflammatory disorder or a proliferative disorder or an infection in accordance with the methods of the invention. One example of such an immunomodulatory agent is IL-4. IL-4 enhances antigen-specific activity of TH2 cells at the expense of the TH1 cell function (see, e.g., Yokota et al., 1986 Proc. Natl. Acad. Sci., USA, 83:5894-5898; and U.S. Pat. No. 5,017,691). Other examples of immunomodulatory agents that affect the biological activity (e.g., proliferation, differentiation, and/or effector functions) of T-helper cells (in particular, TH1 and/or TH2 cells) include, but are not limited to, IL-2, IL-4, IL-5, IL-6, IL-9, IL-10, IL-12, IL-13, IL-15, and interferon (IFN)-γ.

In a preferred embodiment, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another preferred embodiment, when the subject is a human, the proteins, polypeptides, or peptides that are utilized as immunomodulatory agents are human or humanized.

In accordance with the invention, one or more immunomodulatory agents are administered to a subject with a disorder disorder (e.g., a disorder characterized by or associated with aberrant angiogensis, a proliferative disorder, an inflammatory disorder or a disorder prevented, managed, treated or ameliorated by inhibiting NF-κB activation and phosphorylation of p44/42 MAPK, or by reducing or inhibiting production of NO, IL-1β, TNF-α and expression of iNOS and Cox-2 gene expression) prior to, subsequent to, or concomitantly with a compound of the invention. Preferably, one or more immunomodulatory agents are administered to a subject with a proliferative disorder or an inflammatory disorder in combination with a compound of the invention to reduce or inhibit one or more aspects of the immune response. Any technique well-known to one skilled in the art can be used to measure one or more aspects of the immune response in a particular subject, and thereby determine when to administer an immunomodulatory agent to said subject. In a preferred embodiment, a mean absolute lymphocyte count of approximately 500 cells/mm³, preferably 600 cells/mm³, 650 cells/mm³, 700 cells/mm³, 750 cells/mm³, 800 cells/mm³, 900 cells/mm³, 1000 cells/mm³, 1100 cells/mm³, or 1200 cells/mm³ is maintained in a subject. In another preferred embodiment, a subject with a proliferative disorder or an inflammatory disorder is not administered an immunomodulatory agent if their absolute lymphocyte count is 500 cells/mm³ or less, 550 cells/mm³ or less, 600 cells/mm³ or less, 650 cells/mm³ or less, 700 cells/mm³ or less, 750 cells/mm³ or less, or 800 cells/mm³ or less.

In a preferred embodiment, one or more immunomodulatory agents are administered to a subject with a disorder (e.g., a disorder characterized by or associated with aberrant angiogensis, a proliferative disorder, an inflammatory disorder or a disorder prevented, managed, treated or ameliorated by inhibiting NF-κB activation and phosphorylation of p44/42 MAPK, or by reducing or inhibiting production of NO, IL-1, TNF-α and expression of iNOS and Cox-2 gene expression) in combination with a compound of the invention so as to transiently reduce or inhibit one or more aspects of the immune response. Such a transient inhibition or reduction of one or more aspects of the immune system can last for hours, days, weeks, or months. Preferably, the transient inhibition or reduction in one or more aspects of the immune response last for a few hours (e.g., 2 hours, 4 hours, 6 hours, 8 hours, 12 hours, 14 hours, 16 hours, 18 hours, 24 hours, 36 hours, or 48 hours), a few days (e.g., 3 days, 4 days, 5 days, 6 days, 7 days, or 14 days), or a few weeks (e.g., 3 weeks, 4 weeks, 5 weeks or 6 weeks). The transient reduction or inhibition of one or more aspects of the immune response enhances the prophylactic and/or therapeutic capabilities of a compound of the invention.

Nucleic acid molecules encoding proteins, polypeptides, or peptides with immunomodulatory activity or proteins, polypeptides, or peptides with immunomodulatory activity can be administered to a subject with a disorder (e.g., a disorder characterized by or associated with aberrant angiogensis, a proliferative disorder, an inflammatory disorder or a disorder prevented, managed, treated or ameliorated by inhibiting NF-κB activation and phosphorylation of p44/42 MAPK, or by reducing or inhibiting production of NO, IL-1β, TNF-α and expression of iNOS and Cox-2 gene expression) in accordance with the methods of the invention. Further, nucleic acid molecules encoding derivatives, analogs, or fragments of proteins, polypeptides, or peptides with immunomodulatory activity, or derivatives, analogs, or fragments of proteins, polypeptides, or peptides with immunomodulatory activity can be administered to a subject with a disorder (e.g., a disorder characterized by or associated with aberrant angiogensis, a proliferative disorder, an inflammatory disorder or a disorder prevented, managed, treated or ameliorated by inhibiting NF-κB activation and phosphorylation of p44/42 MAPK, or by reducing or inhibiting production of NO, IL-10, TNF-α and expression of iNOS and Cox-2 gene expression) in accordance with the methods of the invention. Preferably, such derivatives, analogs, and fragments retain the immunomodulatory activity of the full-length, wild-type protein, polypeptide, or peptide.

Proteins, polypeptides, or peptides that can be used as anti-angiogenic agents can be produced by any technique well-known in the art or described herein. Proteins, polypeptides or peptides with immunomodulatory activity can be engineered so as to increase the in vivo half-life of such proteins, polypeptides, or peptides utilizing techniques well-known in the art or described herein. Preferably, agents that are commercially available and known to function as immunomoulatory agents are used in the compositions and methods of the invention. The immunomodulatory activity of an agent can be determined in vitro and/or in vivo by any technique well-known to one skilled in the art, including, e.g., by CTL assays ($^{51}$Cr release assays), proliferation assays ($^{3}$H-thymidine incorporation or trypan blue cell counts), northern blot assays, and immunoassays (e.g. ELISAs and western blot expression) for the expression of particular gene products (e.g., RNA or proteins) such as co-stimulatory molecules and cytokines.

Immunomodulatory agents and their dosages, routes of administration and recommended usage are known in the art and have been described in such literature as the Physician's Desk Reference (58$^{th}$ ed., 2004).

5.9.2 Anti-Angiogenic Agents

Anti-angiogenic agents can be used in the compositions and methods of the invention. Non-limiting examples anti-angiogenic agents include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-α, nucleic acid molecules (e.g., antisense molecules or triple helices), organic molecules, inorganic molecules, and small molecules that reduce or inhibit angiogenesis. In particular, examples of anti-angiogenic agents, include, but are not limited to, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the anti-angiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, anti-integrin $\alpha_v\beta_3$ antibodies, acid fibroblast growth factor (aFGF) antagonists, basic fibroblast growth factor (bFGF) antagonists, vascular endothelial growth factor (VEGF) antagonists (e.g., anti-VEGF antibodies such as Avastin®), and VEGF receptor (VEGFR) antagonists (e.g., anti-VEGFR antibodies).

Examples of integrin $\alpha_v\beta_3$ antagonists include, but are not limited to, proteinaceous agents such as non-catalytic metalloproteinase fragments, RGD peptides, peptide mimetics, fusion proteins, disintegrins or derivatives or analogs thereof, and antibodies that immunospecifically bind to integrin $\alpha_v\beta_3$, nucleic acid molecules, organic molecules, and inorganic molecules. Non-limiting examples of antibodies that immunospecifically bind to integrin $\alpha_v\beta_3$ include 11D2 (Searle). Non-limiting examples of small molecule peptidometric integrin $\alpha_v\beta_3$ antagonists include S836 (Searle) and S448 (Searle). Examples of disintegrins include, but are not limited to, Accutin. The invention also encompasses the use of any of the integrin $\alpha_v\beta_3$ antagonists disclosed in the following U.S. Patents and International publications in the compositions and methods of the invention: U.S. Pat. Nos. 5,652,109; 5,652,110; 5,578,704; 5,149,780; 5,196,511; 5,204,445; 5,262,520; 5,306,620; 5,478,725; 5,498,694; 5,523,209; 5,578,704; 5,589,570; 5,652,109; 5,652,110; 5,693,612; 5,705,481; 5,753,230; 5,767,071; 5,770,565; 5,780,426; 5,817,457; 5,830,678; 5,849,692; 5,955,572; 5,985,278; 6,048,861; 6,090,944; 6,096,707; 6,130,231; 6,153,628; 6,160,099; and 6,171,58; and International Publication Nos. WO 95/22543; WO 98/33919; WO 00/78815; WO 00/31248; WO 98/46264; WO 98/40488; and WO 02/070007, each of which is incorporated herein by reference in its entirety.

In a specific embodiment of the invention, an anti-angiogenic agent is endostatin. Naturally occurring endostatin consists of the C-terminal ~180 amino acids of collagen XVIII (cDNAs encoding two splice forms of collagen XVIII have GenBank Accession Nos. AF18081 and AF18082). In another embodiment of the invention, an anti-angiogenic agent is a plasminogen fragment (the coding sequence for plasminogen can be found in GenBank Accession Nos. NM_000301 and A33096). Angiostatin peptides naturally include the four kringle domains of plasminogen, kringle 1 through kringle 4. It has been demonstrated that recombinant kringle 1, 2 and 3 possess the anti-angiogenic properties of the native peptide, whereas kringle 4 has no such activity (Cao et al., 1996, J. Biol. Chem. 271:29461-29467). Accordingly, the angiostatin peptides comprises at least one and preferably more than one kringle domain selected from the group consisting of kringle 1, kringle 2 and kringle 3. In a specific embodiment, the anti-angiogenic peptide is the 40 kDa isoform of the human angiostatin molecule, the 42 kDa isoform of the human angiostatin molecule, the 45 kDa isoform of the human angiostatin molecule, or a combination thereof. In another embodiment, an anti-angiogenic agent is the kringle 5 domain of plasminogen, which is a more potent inhibitor of angiogenesis than angiostatin (angiostatin comprises kringle domains 1-4). In another embodiment of the invention, an anti-angiogenic agent is antithrombin III. Antithrombin III, which is referred to hereinafter as antithrombin, comprises a heparin binding domain that tethers the protein to the vasculature walls, and an active site loop which interacts with thrombin. When antithrombin is tethered to heparin, the protein elicits a conformational change that allows the active loop to interact with thrombin, resulting in the proteolytic cleavage of said loop by thrombin. The proteolytic cleavage event results in another change of conformation of antithrombin, which (i) alters the interaction interface between thrombin and antithrombin and (ii) releases the complex from heparin (Carrell, 1999, Science 285:1861-1862, and references therein). O'Reilly et al. (1999, Science 285:1926-1928) have discovered that the cleaved antithrombin has potent anti-angiogenic activity. Accordingly, in one embodiment, an anti-angiogenic agent is the anti-angiogenic form of antithrombin. In another embodiment of the invention, an anti-angiogenic agent is the 40 kDa and/or 29 kDa proteolytic fragment of fibronectin.

In another embodiment of the invention, an anti-angiogenic agent is a urokinase plasminogen activator (uPA) receptor antagonist. In one mode of the embodiment, the antagonist is a dominant negative mutant of uPA (see, e.g., Crowley et al., 1993, Proc. Natl. Acad. Sci. USA 90:5021-5025). In another mode of the embodiment, the antagonist is a peptide antagonist or a fusion protein thereof (Goodson et al., 1994, Proc. Natl. Acad. Sci. USA 91:7129-7133). In yet another mode of the embodiment, the antagonist is a dominant negative soluble uPA receptor (Min et al., 1996, Cancer Res. 56:2428-2433). In another embodiment of the invention, an anti-angiogenic agent is the 16 kDa N-terminal fragment of prolactin, comprising approximately 120 amino acids, or a biologically active fragment thereof (the coding sequence for prolactin can be found in GenBank Accession No. NM_000948). In another embodiment of the invention, an anti-angiogenic agent is the 7.8 kDa platelet factor-4 fragment. In another embodiment of the invention, an anti-angiogenic agent is a small peptide corresponding to the anti-angiogenic 13 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, the small anti-angiogenic peptides of laminin, fibronectin, procollagen, or EGF, or small peptide antagonists of integrin $\alpha_v\beta_3$ or the VEGF receptor. In another embodiment, the small peptide comprises an RGD or NGR motif. In certain embodiments, an anti-angiogenic agent is a TNF-α antagonist. In other embodiments, an anti-angiogenic agent is not a TNF-α antagonist.

Nucleic acid molecules encoding proteins, polypeptides, or peptides with anti-angiogenic activity, or proteins, polypeptides or peptides with anti-angiogenic activity can be administered to a subject with a disorder (e.g., a disorder characterized by or associated with aberrant angiogensis, a proliferative disorder, an inflammatory disorder or a disorder prevented, managed, treated or ameliorated by inhibiting NF-κB activation and phosphorylation of p44/42 MAPK, or by reducing or inhibiting production of NO, IL-1β, TNF-α and expression of iNOS and Cox-2 gene expression) in accordance with the methods of the invention. Further, nucleic acid molecules encoding derivatives, analogs, fragments, or variants of proteins, polypeptides, or peptides with anti-angiogenic activity, or derivatives, analogs, fragments, or variants of proteins, polypeptides, or peptides with anti-angiogenic activity can be administered to a subject with a disorder (e.g., a disorder characterized by or associated with aberrant angiogensis, a proliferative disorder, an inflammatory disorder or a disorder prevented, managed, treated or ameliorated by inhibiting NF-κB activation and phosphorylation of p44/42 MAPK, or by reducing or inhibiting production of NO, IL-1β, TNF-α and expression of iNOS and Cox-2 gene expression) in accordance with the methods of the invention. Preferably, such derivatives, analogs, variants, and fragments retain the anti-angiogenic activity of the full-length, wild-type protein, polypeptide, or peptide.

Proteins, polypeptides, or peptides that can be used as anti-angiogenic agents can be produced by any technique well-known in the art or described herein. Proteins, polypeptides or peptides with anti-angiogenic activity can be engineered so as to increase the in vivo half-life of such proteins, polypeptides, or peptides utilizing techniques well-known in the art or described herein. Preferably, anti-angiogenic agents that are commercially available are used in the compositions and methods of the invention. The anti-angiogenic activity of an agent can be determined in vitro and/or in vivo by any technique well-known to one skilled in the art or described herein.

Anti-angiogenic agents and their dosages, routes of administration and recommended usage are known in the art and have been described in such literature as the Physician's Desk Reference ($58^{th}$ ed., 2004).

5.9.3 TNF-α Antagonists

TNF-α antagonists can be used in the compositions and methods of the invention. Non-limiting examples of TNF-α antagonists include proteins, polypeptides, peptides, fusion proteins, antibodies (e.g., human, humanized, chimeric, monoclonal, polyclonal, Fvs, ScFvs, Fab fragments, $F(ab)_2$ fragments, and antigen-binding fragments thereof) such as antibodies that immunospecifically bind to TNF-α, nucleic acid molecules (e.g., antisense molecules or triple helices), organic molecules, inorganic molecules, and small molecules that block, reduce, inhibit or neutralize a function, an activity and/or the expression of TNF-α. In various embodiments, a TNF-α antagonist reduces the function, activity and/or expression of TNF-α by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

Examples of antibodies that immunospecifically bind to TNF-α include, but are not limited to, infliximab (REMICADE®; Centacor), D2E7 (Abbott Laboratories/Knoll Pharmaceuticals Co., Mt. Olive, N.J.), CDP571 which is also known as HUMICADE™ and CDP-870 (both of Celltech/Pharmacia, Slough, U.K.), and TN3-19.12 (Williams et al., 1994, Proc. Natl. Acad. Sci. USA 91: 2762-2766; Thorbecke et al., 1992, Proc. Natl. Acad. Sci. USA 89:7375-7379). The present invention also encompasses the use of the antibodies that immunospecifically bind to TNF-α disclosed in the following U.S. patents in the compositions and methods of the invention: U.S. Pat. Nos. 5,136,021; 5,147, 638; 5,223,395; 5,231,024; 5,334,380; 5,360,716; 5,426, 181; 5,436,154; 5,610,279; 5,644,034; 5,656,272; 5,658, 746; 5,698,195; 5,736,138; 5,741,488; 5,808,029; 5,919, 452; 5,958,412; 5,959,087; 5,968,741; 5,994,510; 6,036,978; 6,114,517; and 6,171,787; each of which are herein incorporated by reference in their entirety. Examples of soluble TNF-α receptors include, but are not limited to, sTNF-R1 (Amgen), etanercept (ENBREL™; Immunex) and its rat homolog RENBREL™, soluble inhibitors of TNF-α derived from TNFrI, TNFrII (Kohno et al., 1990, Proc. Natl. Acad. Sci. USA 87:8331-8335), and TNF-α Inh (Seckinger et al., 1990, Proc. Natl. Acad. Sci. USA 87:5188-5192).

In one embodiment, a TNF-α antagonist used in the compositions and methods of the invention is a soluble TNF-α receptor. In a specific embodiment, a TNF-α antagonist used in the compositions and methods of the invention is etanercept (ENBREL™; Immunex) or a fragment, derivative or analog thereof. In another embodiment, a TNF-α antagonist used in the compositions and methods of the invention is an antibody that immunospecifically binds to TNF-α. In a specific embodiment, a TNF-α antagonist used in the compositions and methods of the invention is infliximab (REMICADE®; Centacor) a derivative, analog or antigen-binding fragment thereof.

Other TNF-α antagonists encompassed by the invention include, but are not limited to, IL-10, which is known to block TNF-α production via interferon γ-activated macrophages (Oswald et al. 1992, Proc. Natl. Acad. Sci. USA 89:8676-8680), TNFR-IgG (Ashkenazi et al., 1991, Proc. Natl. Acad. Sci. USA 88:10535-10539), the murine product TBP-1 (Serono/Yeda), the vaccine CytoTAb (Protherics), antisense molecule104838 (ISIS), the peptide RDP-58 (SangStat), thalidomide (Celgene), CDC-801 (Celgene), DPC-333 (Dupont), VX-745 (Vertex), AGIX-4207 (AtheroGenics), ITF-2357 (Italfarmaco), NPI-13021-31 (Nereus), SCIO-469 (Scios), TACE targeter (Immunix/AHP), CLX-120500 (Calyx), Thiazolopyrim (Dynavax), auranofin (Ridaura) (SmithKline Beecham Pharmaceuticals), quinacrine (mepacrine dichlorohydrate), tenidap (Enablex), Melanin (Large Scale Biological), and anti-p38 MAPK agents by Uriach.

Nucleic acid molecules encoding proteins, polypeptides, or peptides with TNF-α antagonist activity, or proteins, polypeptides, or peptides with TNF-α antagonist activity can be administered to a subject with a disorder (e.g., a disorder characterized by or associated with aberrant angiogensis, a proliferative disorder, an inflammatory disorder or a disorder prevented, managed, treated or ameliorated by inhibiting NF-κB activation and phosphorylation of p44/42 MAPK, or by reducing or inhibiting production of NO, IL-1β, TNF-α and expression of iNOS and Cox-2 gene expression) in accordance with the methods of the invention. Further, nucleic acid molecules encoding derivatives, analogs, fragments or variants of proteins, polypeptides, or peptides with TNF-α antagonist activity, or derivatives, analogs, fragments or variants of proteins, polypeptides, or peptides with TNF-α antagonist activity can be administered to a subject with a disorder (e.g., a disorder characterized by or associated with aberrant angiogensis, a proliferative disorder, an inflammatory disorder or a disorder prevented, managed, treated or ameliorated by inhibiting NF-κB activation and phosphorylation of p44/42 MAPK, or by reducing or inhibiting production of NO, IL-10, TNF-α and expression of iNOS and Cox-2 gene expression) in accordance with the methods of the invention. Preferably, such derivatives, analogs, variants and fragments retain the TNF-α antagonist activity of the full-length, wild-type protein, polypeptide, or peptide.

Proteins, polypeptides, or peptides that can be used as TNF-α antagonists can be produced by any technique well-known in the art or described herein. Proteins, polypeptides or peptides with TNF-α antagonist activity can be engineered so as to increase the in vivo half-life of such proteins, polypeptides, or peptides utilizing techniques well-known in the art or described herein. Preferably, agents that are commercially available and known to function as TNF-α antagonists are used in the compositions and methods of the invention. The TNF-α antagonist activity of an agent can be determined in vitro and/or in vivo by any technique well-known to one skilled in the art.

TNF-α antagonists and their dosages, routes of administration and recommended usage are known in the art and have been described in such literature as the Physician's Desk Reference (58th ed., 2004).

5.9.4 Anti-Inflammatory Agents

Any anti-inflammatory therapy (e.g., an anti-inflammatory agent) can be used in the compositions and methods of the invention. Non-limiting examples of anti-inflammatory agents include non-steroidal anti-inflammatory drugs (NSAIDs), steroidal anti-inflammatory drugs, beta-agonists, anticholingeric agents, antihistamines (e.g., ethanolamines, ethylenediamines, piperazines, and phenothiazine), and methyl xanthines. Examples of NSAIDs include, but are not limited to, aspirin, ibuprofen, salicylates, acetominophen, celecoxib (CELEBREX™), diclofenac (VOLTAREN™), etodolac (LODINE™), fenoprofen (NALFON™), indomethacin (INDOCIN™), ketorolac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™, NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

Anti-inflammatory agents and their dosages, routes of administration and recommended usage are known in the art and have been described in such literature as the Physician's Desk Reference (58th ed., 2004).

5.9.5 Anti-Cancer Agents

Therapies (e.g., any prophylactic or therapeutic agent) useful for the prevention, treatment, management, or amelioration of one or more symptoms associated with a proliferative disorder, such as cancer can be used in compositions and methods of the invention. Therapeutic or prophylactic agents include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, and/or biological therapies/immunotherapies.

In certain embodiments, the anti-cancer agent is an immunomodulatory agent such as a chemotherapeutic agent. In other embodiments, the anti-cancer agent is not an immunomodulatory agent. In specific embodiments, the anti-cancer agent is an anti-angiogenic agent. In other embodiments, the anti-cancer agent is not an anti-angiogenic agent.

Examples of anti-cancer agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide;

bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandronate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin-2 (including recombinant interleukin 2, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrnubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; Avastin®; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

In more particular embodiments, the present invention encompasses compositions of the invention that comprise anti-cancer agents such as those disclosed in Table 1. The present invention also encompasses methods that include administration a compound or a composition of the invention.

TABLE 1

| Therapeutic Agent | Dose/Administration/Formulation | | |
|---|---|---|---|
| Doxorubicin hydrochloride (Adriamycin RDF ® and Adriamycin PFS ®) | Intravenous | 60-75 mg/m² on Day 1 | 21 day intervals |
| Epirubicin hydrochloride (Ellence ™) | Intravenous | 100-120 mg/m² on Day 1 of each cycle or divided equally and given on Days 1-8 of the cycle | 3-4 week cycles |
| Fluorousacil | Intravenous | How supplied: 5 mL and 10 mL vials (containing 250 and 500 mg flourouracil respectively) | |
| Docetaxel (Taxotere ®) | Intravenous | 60-100 mg/m² over 1 hour | Once every 3 weeks |
| Paclitaxel (Taxol ®) | Intravenous | 175 mg/m² over 3 hours | Every 3 weeks for 4 courses (administered sequentially to doxorubicin-containing combination chemotherapy) |
| tamoxifen citrate (Nolvadex ®) | Oral (tablet) | 20-40 mg Dosages greater than 20 mg should be given in divided doses (morning and evening) | Daily |
| leucovorin calcium for injection | Intravenous or intramuscular injection | How supplied: 350 mg vial | Dosage is unclear from text. PDR 3610 |
| luprolide acetate (Lupron ®) | Single subcutaneous injection | 1 mg (0.2 mL or 20 unit mark) | Once a day |
| Flutamide (Eulexin ®) | Oral (capsule) | 250 mg (capsules contain 125 mg flutamide each) | 3 times a day at 8 hour intervals (total daily dosage 750 mg) |
| Nilutamide (Nilandron ®) | Oral (tablet) | 300 mg or 150 mg (tablets contain 50 or 150 mg nilutamide each) | 300 mg once a day for 30 days followed by 150 mg once a day |

TABLE 1-continued

| Therapeutic Agent | Dose/Administration/Formulation | | |
|---|---|---|---|
| Bicalutamide (Casodex ®) | Oral (tablet) | 50 mg (tablets contain 50 mg bicalutamide each) | Once a day |
| Progesterone | Injection | USP in sesame oil 50 mg/mL | |
| Ketoconazole (Nizoral ®) | Cream | 2% cream applied once or twice daily depending on symptoms | |
| prednisone | Oral (tablet) | Initial dosage may vary from 5 mg to 60 mg per day depending on the specific disease entity being treated. | |
| Estramustine phosphate sodium (Emcyt ®) | Oral (capsule) | 14 mg/kg of body weight (i.e. one 140 mg capsule for each 10 kg or 22 lb of body weight) | Daily given in 3 or 4 divided doses |
| etoposide or VP-16 | Intravenous | 5 mL of 20 mg/mL solution (100 mg) | |
| Dacarbazine (DTIC-Dome ®) | Intravenous | 2-4.5 mg/kg | Once a day for 10 days. May be repeated at 4 week intervals |
| Polifeprosan 20 with carmustine implant (BCNU) (nitrosourea) (Gliadel ®) | wafer placed in resection cavity | 8 wafers, each containing 7.7 mg of carmustine, for a total of 61.6 mg, if size and shape of resection cavity allows | |
| Cisplatin | Injection | [n/a in PDR 861] How supplied: solution of 1 mg/mL in multi-dose vials of 50 mL and 100 mL | |
| Mitomycin | Injection | supplied in 5 mg and 20 mg vials (containing 5 mg and 20 mg mitomycin) | |
| gemcitabine HCl (Gemzar ®) | Intravenous | For NSCLC-2 schedules have been investigated and the optimum schedule has not been determined 4 week schedule- administration intravenously at 1000 mg/m$^2$ over 30 minutes on 3 week schedule- Gemzar administered intravenously at 1250 mg/m$^2$ over 30 minutes | 4 week schedule- Days 1, 8 and 15 of each 28-day cycle. Cisplatin intravenously at 100 mg/m$^2$ on day 1 after the infusion of Gemzar. 3 week schedule- Days 1 and 8 of each 21 day cycle. Cisplatin at dosage of 100 mg/m$^2$ administered intravenously after administration of Gemzar on day 1. |
| Carboplatin (Paraplatin ®) | Intravenous | Single agent therapy: 360 mg/m$^2$ I.V. on day 1 (infusion lasting 15 minutes or longer) Other dosage calculations: Combination therapy with cyclophosphamide, Dose adjustment recommendations, Formula dosing, etc. | Every 4 weeks |
| Ifosamide (Ifex ®) | Intravenous | 1.2 g/m$^2$ daily | 5 consecutive days Repeat every 3 weeks or after recovery from hematologic toxicity |
| Topotecan hydrochloride (Hycamtin ®) | Intravenous | 1.5 mg/m$^2$ by intravenous infusion over 30 minutes daily | 5 consecutive days, starting on day 1 of 21 day course |

In specific embodiments, radiation therapy comprising the use of x-rays, gamma rays and other sources of radiation to destroy the cancer cells is used in combination with the compounds or compositions of the invention. In preferred embodiments, the radiation treatment is administered as external beam radiation or teletherapy, wherein the radiation is directed from a remote source. In other preferred embodiments, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the Physician's Desk Reference (58$^{th}$ ed., 2004).

5.9.6 Antibiotics

Antibacterial agents or antibiotics can be used in methods and the compounds and compositions of the invention include but are not limited to: aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol,chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), macrolides (e.g., azithromycin, carbomycin, clarithomycin, dirithromycin, erythromycin, and erythromycin acistrate), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, ciprofloxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

Additional examples of antibacterial agents include but are not limited to Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmnenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafingin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

Antibiotics and their dosages, routes of administration and recommended usage are known in the art and have been described in such literature as the Physician's Desk Reference (58$^{th}$ ed., 2004).

5.9.7 Antiviral Agents

Anti-viral agent can be used in the compositions and the methods of the invention. Non-limiting examples of antiviral agents include proteins, polypeptides, peptides, fusion protein antibodies, nucleic acid molecules, organic molecules, inorganic molecules, and small molecules that inhibit or reduce the attachment of a virus to its receptor, the internalization of a virus into a cell, the replication of a virus, or release of virus from a cell.

Many examples of antiviral compounds that can be used in combination with the compounds of the invention are known in the art and include but are not limited to: rifampicin, nucleoside reverse transcriptase inhibitors (e.g., AZT, ddI, ddC, 3TC, d4T), non-nucleoside reverse transcriptase inhibitors (e.g., Efavirenz, Nevirapine), protease inhibitors (e.g., aprenavir, indinavir, ritonavir, and saquinavir), idoxuridine, cidofovir, acyclovir, ganciclovir, zanamivir, amantadine, and Palivizumab. Other examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime.

Antiviral agents and their dosages, routes of administration and recommended usage are known in the art and have been described in such literature as the Physician's Desk Reference (58$^{th}$ ed., 2004).

5.9.8 Antifungal Compounds

Antifungal compounds can be used in the methods and compositions of the invention include but are not limited to: polyenes (e.g., amphotericin b, candicidin, mepartricin, natamycin, and nystatin), allylamines (e.g., butenafine, and naftifine), imidazoles (e.g., bifonazole, butoconazole, chlordantoin, flutrimazole, isoconazole, ketoconazole, and lanoconazole), thiocarbamates (e.g., tolciclate, tolindate, and tolnaftate), triazoles (e.g., fluconazole, itraconazole, saperconazole, and terconazole), bromosalicylchloranilide, buclosamide, calcium propionate, chlorphenesin, ciclopirox, azaserine, griseofulvin, oligomycins, neomycin undecylenate, pyrrolnitrin, siccanin, tubercidin, and viridin. Additional examples of antifungal compounds include but are not limited to Acrisorcin; Ambruticin; Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofingin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; Pyrrolnitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafuigin; Undecylenic Acid; Viridoflilvin; Zinc Undecylenate; and Zinoconazole Hydrochloride.

5.9.9 Antiprotozoal Compounds

Antiprotozoal compounds can be used in the methods and compositions of the invention to treat parasitic diseases are known in the art and include but are not limited to: quinines, chloroquine, mefloquine, proguanil, pyrimethamine, metronidazole, diloxanide furoate, tinidazole, amphotericin, sodium stibogluconate, trimoxazole, and pentamidine isetionate. Many examples of antiparasite drugs that can be used in combination with the compounds and compositions of the invention to treat parasitic diseases are known in the art and include but are not limited to: mebendazole, levamisole, niclosamide, praziquantel, albendazole, ivermectin, diethylcarbamazine, and thiabendazole. Further examples of anti-parasitic compounds include but are not limited to Acedapsone; Amodiaquine Hydrochloride; Amquinate; Arteflene; Chloroquine; Chloroquine Hydrochloride; Chloroquine Phosphate; Cycloguanil Pamoate; Enpiroline Phosphate; Halofantrine Hydrochloride; Hydroxychloroquine Sulfate; Mefloquine Hydrochloride; Menoctone; Mirincamycin Hydrochloride; Primaquine Phosphate; Pyrimethamine; Quinine Sulfate; and Tebuquine.

5.10 Dosage & Frequency of Administration

The amount of the compound or composition of the invention which will be effective in conjunction with a particular method will vary e.g., with the nature and severity of the disorder and the route by which the active ingredient is administered. The frequency and dosage will also vary according to factors specific for each subject, such as age, body, weight, response, and the past medical history of the subject. Effective doses may be extrapolated from dose-response curves derived from in vitro or animal model test systems. Suitable regiments can be selected by one skilled in the art by considering such factors and by following, for example, dosages reported in the literature and recommended in the Physician's Desk Reference (58$^{th}$ ed., 2004).

Exemplary doses include milligram or microgram amounts of the compound of the invention per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In general, the recommended daily dose range of a compound of the invention for the conditions described herein lie within the range of from about 0.01 mg to about 1000 mg per day, given as a single once-a-day dose preferably as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that in instances where a clinician or treating physician is involved, such a person will know how and when to interrupt, adjust, or terminate therapy in conjunction with individual subject response.

Different therapeutically effective amounts may be applicable for different diseases, as will be readily known by those of skill in the art. Similarly, amounts sufficient to prevent, manage, treat or ameliorate such disorders, but insufficient to cause, or sufficient to reduce, adverse effects associated with the compounds of the invention are also encompassed by the above described dosage amounts and dose frequency schedules. Further, when a subject is administered multiple dosages of a compound or compositions of the invention, not all of the dosages need be the same. For example, the dosage administered to the subject may be increased to improve the prophylactic or therapeutic effect of the compound or it may be decreased to reduce one or more side effects that a particular subject is experiencing.

In certain embodiments, the dosage of the composition of the invention or a compound of the invention administered to prevent or treat a disorder, e.g., a cancer, or symptom thereof in a subject is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In some embodiments, the dosage of the composition of the invention or a compound of the invention administered to prevent or treat a disorder, e.g., cancer, or symptom thereof, in a subject is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7m g, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosages of prophylactic or therapeutic agents other than compounds of the invention, which have been or are currently being used to prevent or treat a disorder, e.g., a cancer, or symptom thereof, can be used in the combination therapies of the invention. Preferably, dosages lower than those which have been or are currently being used to prevent or treat a disorder, e.g., a cancer, or symptom thereof are used in the combination therapies of the invention. The recommended dosages of agents currently used for the prevention or treatment of a disorder, e.g., a cancer, or symptom thereof can be obtained from any reference in the art including, but not limited to, Hardman et al., eds., 1996, Goodman & Gilman's The Pharmacological Basis Of Basis Of Therapeutics 9$^{th}$ Ed, Mc-Graw-Hill, New York; Physician's Desk Reference (PDR) 57$^{th}$ Ed., 2003, Medical Economics Co., Inc., Montvale, N.J., which are incorporated herein by reference in their entireties.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, where a physcan or clinical visit is involved, two or more therapies (e.g., prophylactic or therapeutic agents)are administered within the same subject visit. The therapies can be administered simultaneously.

In certain embodiments, one or more compounds of the invention and one or more other the therapies (e.g., prophylactic or therapeutic agents)are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of oneof the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the invention provides a method of preventing or treating a disorder, e.g., a cancer, or symptom thereof comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every 3 days, preferably, once every 4 days, once every 5 days, once every 6 days, once every 7 days, once every 8 days, once every 10 days, once every two weeks, once every three weeks, or once a month.

5.11 Biological Assays

Aspects of the pharmaceutical, nutraceutical or cosmetic compositions or compounds of the invention can routinely be tested in vitro, in a cell culture system, and/or in an animal model organism, such as a rodent animal model system, for a desired activity prior to use in humans. For example, assays can include cell culture assays in which a tissue sample is grown in culture, and exposed to or otherwise contacted with a pharmaceutical composition, and the effect of such composition upon the tissue sample is observed. The tissue sample, for example, can be obtained by biopsy from the a subject. This test allows the identification of the therapeutically most effective therapy (e.g., prophylactic or therapeutic agent(s)) for each individual patient. In various specific embodiments, in vitro assays can be carried out with representative cells of cell types involved in a disorder (e.g., immune cells or cancer cells), to determine if a compound or composition of the invention has a desired effect upon such cell types. As an alternative to the use of tissue, tissue samples, or cell lines, e.g., cancer cell lines can be used in in vitro assays. Examples of cancer cell lines that can be utilized in in vitro assays include, but are not limited to, the MCF-7 breast cancer cell line, the MCF-7/ADR multi-drug resistant breast cancer cell line, the HT114 human melanoma cell line, the MES/DOX doxorubicenresistant human uterine sarcoma cell line, the HT29 human colorectal cell line, the HCT-116 human colorectal cell line, the A549 human lung carcinoma cell line and the BXPC-3 human pancreas primary adenocarcinoma cell line. Additional cell lines are described in the Examples below.

The pharmaceutical, nutraceutical or cosmetic compositions and compounds of the invention can also be assayed for their ability to induce the expression and/or activation of a gene product (e.g., cellular protein or RNA) and/or to induce signal transduction in immune cells, cancer cells, and/or endothelial cells. The induction of the expression or activation of a gene product or the induction of signal transduction pathways in immune cells, cancer cells (in particular tubulin-binding agent resistant cancer cells) and/or endothelial cells can be assayed by techniques known to those of skill in the art including, e.g., ELISAs flow cytometry, Northern blot analysis, Western blot analysis, RT-PCR kinase assays and electrophoretic mobility shift assays. See also, U.S. Pat. No. 5,955,269. The compositions and compounds of the invention can also be assayed for their ability to modulate immune cell proliferation, endothelial and cell cancer cell proliferation using the exampl, techniques known to those in art, including, but not limited to, $^3$H-thymidine incorporation, trypan blue cell counts, and fluorescence activated cell sorting ("FACS") analysis. The compositions and compounds of the invention can also be assayed for their ability to induce cytolysis. The compositions and compounds of the invention can also be assayed for their ability to inhibit cell migration, cell adhesion angiogenesis and/or tubulin polymerization using techniques well-known to one of skill in the art or described herein. The compositions and compound can also be assayed for their ability to induce cell cycle arrest or apoptosis.

The pharmaceutical, nutraceutical or cosmetic compositions and compounds of the invention can also be tested in suitable animal model systems prior to use in humans. Any animal system well-known in the art may be used. In a specific embodiment of the invention, the pharmaceutical compositions and compounds of the invention are tested in a mouse model system. Such animal model systems include, but are not limited to, rats, mice, chicken, cows, monkeys, pigs, dogs, rabbits, etc. Such model systems are widely used and well-known to the skilled artisan.

The anti-cancer activity of the pharmaceutical, nutraceutical or cosmetic compositions and compounds of the invention can be determined using any suitable animal model, including, but not limited to, SCID mice with a tumor or injected with malignant cells. Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4): 179-85). An example of an animal model for breast cancer includes, but is not limited to, a transgenic mouse that overexpresses cyclin Dl (see, e.g., Hosokawa et al., 2001, Transgenic Res 10(5):471-8). An example of an animal model for colon cancer includes, but is not limited to, a TCR b and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumors (see, e.g., Ghaneh et al., 2001, Gene Ther 8(3): 199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

The toxicity and/or efficacy of the pharmaceutical, nutraceutical or cosmetic compositions and compounds of the invention can be determined by standard procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Pharmaceutical, nutraceutical or cosmetic compositions and compounds of the invention that exhibit large therapeutic indices are preferred.

The data obtained from the cell culture assays and animal studies can be used in formulating a range of dosage of the pharmaceutical, nutraceutical or cosmetic compositions and compounds of the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the methods of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography (HPLC) and radioimmunasssay (RIA). The pharmacokinetics of a prophylactic or therapeutic can be determined, e.g., by measuring parameters such as peak plasma level (Cmax), area under the curve (AUC, which is measured by plotting plasma concentration of the agent versus time, and reflects bioavailability), half-life of the compound ($t_{1/2}$), and time at maximum concentration.

Efficacy in preventing or treating a proliferative disorder such as cancer may be demonstrated, e.g., by detecting the ability of the pharmaceutical, nutraceutical or cosmetic compositions and compounds of the invention to reduce one or more symptoms of the proliferative disorder, to reduce the proliferation of cancerous cells, to reduce the spread of cancerous cells, or to reduce the size of a tumor, as for example, by using techniques and methods described herein.

5.12 Articles of Manufacture

The invention encompasses articles of manufacture. A typical article of manufacture of the invention comprises a unit dosage form of a composition or compound of the invention. In one embodiment, the unit dosage form is a container, preferably a sterile container, containing an effective amount of a composition or compound of the invention and a pharmaceutically acceptable carrier or excipient. The article of manufacture can further comprise a label or printed instructions regarding the use of composition or compound or other informational material that advises the dietitian, physician, technician, consumer, subject, or patient on how to appropriately prevent, treat or derive a beneficial result pertaining to the disorder in question. The article of manufacture can include instructions indicating or suggesting a dosing regimen including, but not limited to, actual doses, monitoring procedures, and other monitoring information. The article of manufacture can also further comprise a unit dosage form of another prophylactic or therapeutic agent, for example, a container containing an effective amount of another prophylactic or therapeutic agent. In a specific embodiment, the article of manufacture comprises a container containing an effective amount of a composition or compound of the invention and a pharmaceutically acceptable carrier or excipient and a container containing an effective amount of another propylactic or therapeutic agent and a pharmaceutically acceptable carrier or excipient. Examples of other prophylactic or therapeutic agents include, but are not limited to, those listed above. Preferably, the packaging material and container included in the article of manufacture are designed to protect the stability of the product during storage and shipment.

Article of manufacture of the invention can further comprise devices that are useful for administering the unit dosage forms. Examples of such devices include, but are not limited to, syringes, drip bags, patches, and inhalers.

Articles of manufacture of the invention can further comprise pharmaceutically acceptable vehicles or consumable vehicles that can be used to administer one or more active ingredients (e.g., a compound of the invention). For example, if an active ingredient is provided in a solid form that must be reconstituted for parenteral or oral/enteral administration, the article of manufacture can comprise a sealed container of a suitable vehicle in which the active ingredient can be dissolved. For parenteral administration, a particulate-free sterile solution is preferred. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

6. EXAMPLES

The following examples describe the preparation and characterization of exemplary compounds of the invention and demonstrate their inhibitory activities on growth of various types of cancer cells.

6.1 Purification of Compounds

The following describes the isolation of compounds from *Rabdosia rubescens*.

General Procedures: TLC was performed on Sigma-Aldrich silica gel TLC plates (250 µm thickness, 2-25 µm particle size). Spots were observed under a UV detector (254 nm) and visualized by spraying with 0.5% vanillin plus 10% $H_2SO_4$ ethanol solution or 60% (v/v) $H_2SO_4$ ethanol solution followed by heating. Silica gel (130-270 mesh), Sephadex LH-20 and RP-18 (60 µm) (Sigma Chemical Co., St. Louis, Mo.) were used for column chromatography. DPPH and $H_2O_2$ were purchased from Sigma Chemical Co. (St. Louis, Mo.). All solvents used were purchased from Fisher Scientific (Springfield, N.J.). $^1H$ and $^{13}C$ NMR spectra and 2D NMR spectra were recorded on an U-,400 instrument (Varian Inc., California). Chemical shifts are expressed in parts per million (δ) using TMS as internal standard. $CD_3OD$, $CDCl_3$ and DMSO-d6 were purchased from Aldrich Chemical Co. GC and GC-MS analysis were performed on a HP Hewlett 5890 packard series II. Mass spectra were obtained by electronic ionization (EI) mode at 70 eV. The oven temperature was 100° C., raised to 200° C. at a rate of 2° C./min, held for 30 minutes, and finally raised to 280° C. at 10° C./min. The injector temperature was 270° C. and the detector temperature was 280° C. The split ratio of sample was set at 60:1. FT-IR was performed on a Perkin-Elmer spectrum BX system. UV was on a Cary 300 Bio UV-Visible spectrophotometer [α]$_D$: Perkin-Elmer 141 Polarimeter. HRFAB-MS was run on JEOL HX-110 double focusing mass spectrometer. LC-MS data were obtained on a HP 59980 B particle beam LC/MS interface with an HP 1100 HPLC instrument.

Plant Material: The dried herb of *R. rubescens* was cultivated in Henan province of China and purchased from Henan Drugs Company. A voucher specimen was deposited in the Herbarium of the College of Pharmacy, Fudan University, Shanghai, China.

Extraction and Isolation: The powdered, air-dried, whole herbs of *R. rubescens* (15 kg) were extracted with 95% EtOH three times at room temperature, and the solution was concentrated under reduced pressure for removal of the solvent and it gave a dark green residue (800 g). The residue was diluted with hot $H_2O$ (2 L) and extracted three times with hexane (1×3 L), EtOAc (1×3 L), and n-BuOH (1×3 L). The $CH_3COOC_2H_5$ residue (230 g), obtained after removal of the solvent, was chromatographed on a silica gel column, packed in $CHCl_3$ using an $CHCl_3$-MeOH gradient solvent system. The fractions were combined after monitoring by TLC. Fractions were submitted repeatedly to Si gel or RP-18 gel column chromatography and eluted with solvents of increasing polarity (hexane, CHCl3, $CH_3COOC_2H_5$, MeOH, and $H_2O$-MeOH). Appropriate fractions were crystallized yielding some diterpenoids. Some fractions were evaporated under vacuum and repeatedly chromatographed on silica gel and Sephadex LH-20 column using as solvent system MeOH-$H_2O$ to give pure compounds. Final purification of some compounds was effected by HPLC (C18 column) with an acetonitrile-$H_2O$ gradient solvent system. The other compounds were further purified by recrystallization and PTLC (Si gel), yielding compounds in order of increasing polarity, such as rosmarinic acid, and methyl rosmarinate.

6.2 Structural Characterization of Exemplary Compounds

Characterization of exemplary compounds from *R. rubescens* was performed utilizing MS, chemical data, and NMR techniques including $^1$H NMR, $^{13}$C NMR, DEPT and 2D NMR, such as COSY, TOCSY, ROESY, HMQC, and HMBC NMR methods.

6.2.1 Rubscendepside

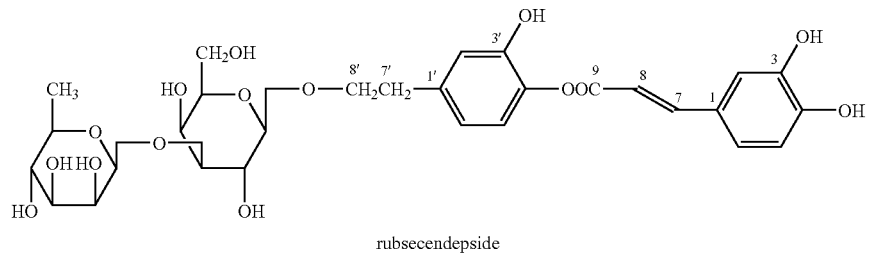

rubsecendepside

Rubscendepside, amorphous slight yellow powder, showed an EIMS molecular ion peak at m/z 623 in accordance with the formula $C_{29}H_{36}O_{15}$, which was confirmed by positive HRFABMS (obsd 647.1950, calc. 647.1951) (M+Na)$^+$ and analysis of its $^{13}$C NMR and DEPT spectra. Its UV spectrum shows $\lambda_{max}$ at 202.0, 221.0, 289.0, and 331.0 nm and $[\alpha]_D$—12.0 (MeOH; c0.0133).

In addition to the above-mentioned signals, the $^{13}$C NMR and DEPT spectra also showed signals due to one methyl, three methylenes (including two oxygenated ones), eighteen methines (including ten oxygen-bearing ones) and seven quaternary carbons (including one carbonyl and four oxygen-bearing double bond ones). HMQC spectroscopy was used to set up the correlation of carbons and protons which were directly bonded (Table 3). COSY spectroscopy was used to set up the correlation of directly coupled protons, such as H-5 (with H-6), H-7 (with H-8), H-5' (with H-6'), H-7' (with H-8'), for glucose H-1 (with H-2), H-2 (with H-3), H-4 (with H-5), H-5 (with H-6), also for rhamnose H-1 (with H-2), H-2 (with H-3), H-3 (with H-4), H-4 (with H-5), H-5 (with H-6).

The $^{13}$C NMR spectrum at δ104.186d and 103.047d showed the presence of two acetal groups and there are two sugar units, which were confirmed by 2D NMR.

In the HMBC spectrum, correlations were clearly observed among H-2 (with C-3, C-4, C-6, and C-7), H-5 (with C-1, C-3, and C-4), H-6 (with C-4, C-7, and C-8), H-7 (with C-6, C-8, and C-9), H-8 (with C-1, and C-9), H-2' (with C-1', C-3', and C-7'), H-5' (with C-4', and C-6'), H-6' (with C-4', C-5', and C-7'), H-7' (with C-1', C-2', C-6', and C-8'), H-8'a&b (with C-1'), for glucose H-1 (with C-8'), H-2 (with C-1, and C-3 both in glucose), for rhamnose H-1 (with C-3 in glucose, C-2, and C-5 both in rhamnose), and H-3 (with C-1, C-4, and C-5 all in rhamnose).

From all the evidence mentioned above, the structure of rubscendepside was identified.

TABLE 3

$^1$H, $^{13}$C and DEPT Data of Rubscendepside

| No. | $^1$H | $^{13}$C | HMBC(H→C) |
|---|---|---|---|
| 1 | | 127.623s | |
| 2 | 7.072d(2.0) | 115.165d | 3, 4, 6, 7 |
| 3 | | 146.835s | |

TABLE 3-continued $^1$H, $^{13}$C and DEPT Data of Rubscendepside

| No. | $^1$H | $^{13}$C | HMBC(H→C) |
|---|---|---|---|
| 4 | | 149.795s | |
| 5 | 6.788d(8.4) | 116.477d | 1, 3, 4 |
| 6 | 6.947dd(2.4, 8.8) | 123.224d | 4, 7, 8 |
| 7 | 7.596d(16.0) | 148.014d | 6, 8, 9 |
| 8 | 6.283d(16.0) | 114.656d | 1, 9 |
| 9 | | 168.272s | |
| 1' | | 131.410s | |
| 2' | 6.705d(2.0) | 117.084d | 1', 3', 7' |
| 3' | | 146.123s | |
| 4' | | 144.672s | |
| 5' | 6.689d(8.4) | 116.269d | 4', 6' |
| 6' | 6.549dd(2.0, 8.4) | 121.241d | 4', 5', 7' |
| 7' | 2.772t(6.4) | 36.562t | 1', 2', 6', 8' |
| 8' | 3.695dd(8.0, 16.4) | 72.273t | 1' |
|    | 4.026dd(7.2, 16.4) |          | 1' |
| Glc (G) | | | |
| 1 | 4.368d(8.0) | 104.186d | 8' |
| 2 | 3.405t(8.4) | 76.193d | 1 (G), 3(G) |
| 3 | 3.819t(8.8) | 81.639d | |
| 4 | 3.533m | 76.014d | |
| 5 | 4.920m | 70.527d | |
| 6 | 3.533m, 3.655m | 62.329t | |
| Rham (R) | | | |
| 1 | 5.193d(1.6) | 103.047d | 3(G), 2(R), 5(R) |
| 2 | 3.953dd(1.6, 3.2) | 72.331d | |
| 3 | 3.603m | 72.007d | 1(R), 4(R), 5(R) |
| 4 | 3.329dd(2.4, 9.6) | 73.753d | |
| 5 | 3.533m | 70.417d | |
| 6 | 1.096d(6.4) | 18.455q | |

From all the evidence mentioned above, the structure of rubescendepside was identified.

6.2.2 Rubescensin J

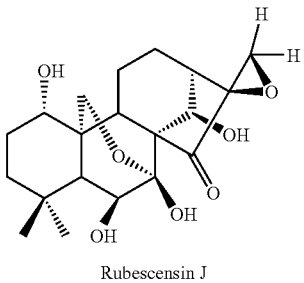

Rubescensin J

Rubescensin J, amorphous powder, showed an ESI molecular ion peak [M–H]⁻ at m/z 379 in accordance with the formula $C_{20}H_{28}O_7$, which was confirmed by positive HRFABMS (obsd, calc.381.1913) and analysis of its $^{13}C$ NMR and DEPT spectra.

Its UV ($\lambda_{max}$ at 206.0 nm), $[\alpha]_D$—28.6 (MeOH; c0.0614), and NMR [$^1H$ NMR δ2.981d (7.6) and 3.067d (7.62) (each 1H); $^{13}C$ NMR δ219.378 (s), 67.086 (s), and 50.613 (t)] spectra showed an exo-epoxide group connected with a carbonyl group on a five-membered ring instead of an exo-methylene group in common ent-kaurane diterpenoids.

In its IR spectrum, the absorption at 3245 cm⁻¹ showed the presence of hydroxyl groups.

In addition to the above-mentioned signals, the $^{13}C$ NMR and DEPT spectra also showed signals due to two methyl, six methylenes (including two oxygenated ones), six methines (including three oxygen-bearing ones) and six quaternary carbons (including one carbonyl and two oxygen-bearing ones). HMQC spectroscopy was used to set up the correlation of carbons and protons which were directly bonded (Table 4). COSY spectroscopy was used to set up the correlation of directly coupled protons, such as H-1 (with H-2), H-5 (with H-6), H-12 (with H13), and H-13 (with H-14). The 13C NMR spectrum at δ98.166s and 64.680t showed the presence of a 7α, 20-hemiacetal group.

The basic skeleton of the molecule was assigned as 7β-hydroxy-7α, 20-epoxy-ent-kaur-16,17-epoxide-15-one, which was substituted by four hydroxyl groups.

Besides the signals due to one epoxide ring group, the $^1H$ and $^{13}C$ NMR spectra of Rubescensin J were very similar to those of oridonin, so it was assumed that Rubescensin J had the same skeleton as that of oridonin and the epoxide ring group was on the 16- and 17-position, which was verified by 2D NMR spectroscopic experiments.

In the HMBC spectrum, correlations were clearly observed among H-1 (with C-2, C-9,-and C-10), H-5 (with C-1, C-3, C-4, C-6, C-9, C-10, C-18, C-19, and C-20), H-6 (with C-4, C-5, C-7, C-8, and C-20), H-9 (with C-10, C-i 1, C-14, and C-16), H-13 (with C-8, C-11, C-12, C-14, and C-16), H-14 (with C-16), H-17a (with C16), H-17b (with C-16), H-18 (with C-3, C-4, C-5, and C-19), H-19 (with C-3, C-4, C-5, and C-18), H-20a (with C-5, C-7, C-9 and C-10), H-20b (with C-5, C-7, C-9 and C-10).

The relative configuration of the substitutes was revealed by ROESY spectrum of NOE experiments. By using the selective NOE experiment, when the proton of H-17a at δ2.981d(7.6) was irradiated, the protons of H-17b at δ 3.067d(7.6), H-13 at δ2.166d(9.2), and H-12a at δ1.798m were responded, so it was confirmed that the 16,17-epoxide ring had the β-configuration as depicted below:

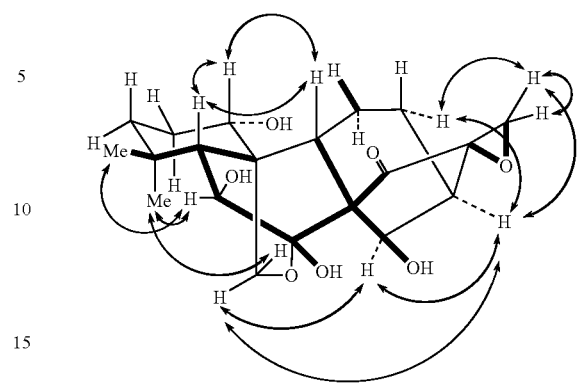

ROESY model of Rubescensin J

From all the evidence mentioned above, rubescensin J was identified as 1α, 6β, 7β, 14β-tetrohydroxy-7α,20-epoxy-ent-kaur-16,17-exo-epoxide-15-one.

TABLE 4

$^1$H, $^{13}$C and HMBC Data of rubescensin J

| No. | $^1$H | $^{13}$C | HMBC(H→C) |
|---|---|---|---|
| 1 | 3.455dd(5.6, 13.2) | 73.924d | 2, 9, 10, |
| 2 | 1.621m | 30.413t | |
| 3 | 1.306d(12.4), 1.432d(13.2) | 39.809t | |
| 4 | | 34.587s | |
| 5 | 1.217d(6.4) | 60.400d | 1, 3, 4, 6, 9, 10, 18, 19, 20 |
| 6 | 3.720d(6.8) | 74.755d | 4, 5, 7, 8, 20 |
| 7 | | 98.166s | |
| 8 | | 63.481s | |
| 9 | 1.923s | 54.453d | 10, 11, 14, 16, 20 |
| 10 | | 42.348s | |
| 11 | 1.798m, 2.093m | 20.710t | |
| 12 | 1.798m, 2.451m | 27.730t | |
| 13 | 2.166d(9.2) | 42.287d | 8, 11, 12, 14, 16 |
| 14 | 5.023d(5.2) | 74.972d | 16 |
| 15 | | 219.378s | |
| 16 | | 67.086s | |
| 17 | 2.981d(7.6), 3.067d(7.6) | 50.613t | 16 |
| 18 | 1.058s | 33.384q | 3, 4, 5, 19 |
| 19 | 1.110s | 22.338q | 3, 4, 5, 18 |
| 20 | 4.043d(9.6), 4.267d(9.6) | 64.680t | 5, 7, 9, 10 |

6.2.3 Rubescensin O-1

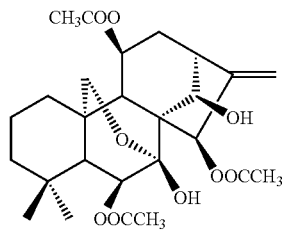

Rubescensin O-1

Rubescensin O-1, amorphous powder, showed an ESI molecular ion peak [M–H]⁻ at m/z 491 in accordance with the formula $C_{26}H_{36}O_9$, which was confirmed by positive HRFABMS (obsd, calc.493.2438) and analysis of its $^{13}C$ NMR and DEPT spectra.

Its UV ($\lambda_{max}$ at 239.0 nm), $[\alpha]_D$—6.0 (MeOH; c0.0167), IR ($v_{max}$ at 1700 and 1640 cm$^{-1}$), and NMR [$^1$H NMR δ6.117s and 5.577d (1.2) (each 1H); $^{13}$C NMR δ79.245 (d), 152.257 (s), and 120.384 (t)] spectra showed an exo-methylene group on a five-membered ring.

In its IR spectrum, the absorption at 3405 cm$^{-1}$ showed the presence of hydroxyl groups. The $^{13}$C NMR spectrum at δ98.679s and 67.450t showed the presence of a 7α,20-hemiacetal group. The signals at $^{13}$C NMR δ170.649 (s), 171.916 (s), 171.218 (s), 21.317 (q), and 21.442 (q), and $^1$H NMR δ2.137 (s), 1.957 (s), and 1.980 (s) showed three acetyl groups in the structure.

In addition to the above-mentioned signals, the 13C NMR and DEPT spectra also showed signals due to two methyl, six methylenes (including one oxygenated ones), seven methines (including four oxygen-bearing ones) and four quaternary carbons. HMQC spectroscopy was used to set up the correlation of carbons and protons which were directly bonded (Table 5). The basic skeleton of Rubescensin O-1 was assigned as 7β-hydroxy-7α,20-epoxy-ent-kaur-16-en-15-ol, which was substituted by two hydroxyl and three acetoxyl groups.

TABLE 5

$^1$H, $^{13}$C and HMBC Data of rubescensin O-1

| No. | $^1$H | $^{13}$C | HMBC(H→C) |
|---|---|---|---|
| 1 | 1.179m | 30.345t | |
| 2 | 1.429m | 19.381t | |
| 3 | 1.429m | 41.835t | |
| 4 | | 34.754s | |
| 5 | 1.473s | 56.407d | |
| 6 | 5.214d(5.6) | 75.059d | 4,5,7,CH$_3$CO(6) |
| 7 | | 98.679s | |
| 8 | | 55.429s | |
| 9 | 2.745d(7.2) | 48.351d | |
| 10 | | 39.407s | |
| 11 | 5.066dd(7.6, 17.6) | 65.363d | |
| 12 | 1.429m, 2.943m | 39.437t | |
| 13 | 2.584d(9.2) | 43.661d | |
| 14 | 4.838s | 72.835d | |
| 15 | 5.344s | 79.245d | 14,16,CH$_3$CO(15) |
| 16 | | 157.602s | |
| 17 | 5.195s, 5.266s | 111.649t | |
| 18 | 0.846s | 32.496q | 3, 4, 5, 19 |
| 19 | 1.129s | 22.478q | 3, 4, 5, 18 |
| 20 | 3.916d(10.4) 4.151d(10.4) | 67.450t | |
| CH$_3$CO(6) | 2.137s | 21.317q | CH$_3$CO(6) |
| CH$_3$CO(6) | | 170.649s | |
| CH$_3$CO(11) | 1.957s | 21.317q | CH$_3$CO(11) |
| CH$_3$CO(11) | | 171.916s | |
| CH$_3$CO(15) | 1.980s | 21.317q | CH$_3$CO(15) |
| CH$_3$CO(15) | | 171.218s | |

Besides the signals due to three acetoxyl groups and the hydroxyl group in the 11-position, the $^1$H and $^{13}$C NMR spectra of Rubescensin O-1 were very similar to those of enmenol, so it was indicated that the molecule had the same skeleton as that of enmenol and the acetyl groups were on the 6,11,15-position, which was verified by 2D NMR spectroscopic experiments. From gCOSY spectrum, the correlations were set up among H-1 with H-2, H-5 with H-6, H-9 with H-11, H-11 with H-12a, H-12a with H-12b, H-12b with H-13, and H-13 with H-14b.

In the HMBC spectrum, correlations were clearly observed among H-5 (with C-1, C-4, C-6, C-9, C-10, C-18, C-19, and C-20), H-6 (with C-4, C-5, C-7, and C at $^{13}$C NMR δ170.649 (s)), H-15 (with C-14 and C-16, and C at $^{13}$C NMR δ171.218 (s)), H-18 (with C-3, C-4, C-5, and C-19), H-19 (with C-3, C-4, C-5, and C-18).

The relative configuration of the substituents was revealed by ROESY spectrum of NOE experiments as depicted below:

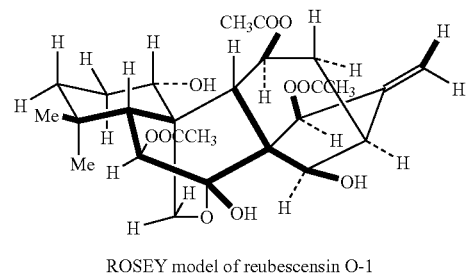

ROSEY model of reubescensin O-1

From all the evidence mentioned above, the structure of rubescensin O-1 was identified.

6.2.4 Rubescensin M

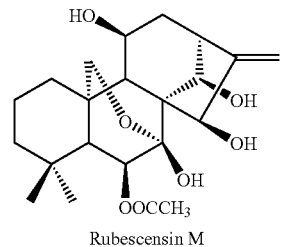

Rubescensin M

Rubescensin M, amorphous powder, showed an ESI molecular ion peak [M−H]$^-$ at m/z 407 in accordance with the formula $C_{22}H_{32}O_7$, which was confirmed by positive HRFABMS (obsd 409.2236, calc. 409.2226) (M+H)$^+$ and analysis of its $^{13}$C NMR and DEPT spectra. Its UV ($\lambda_{max}$ at 202.0 nm), $[\alpha]_D$—22.0 (MeOH ; c0.0808 ), and NMR [$^1$H NMR δ5.186 (s), and 5.239 (s) (each 1H); $^{13}$C NMR δ159.642(s) and 110.824(s)] spectra showed an exo-methylene group on a five-membered ring.

In its IR spectrum, the absorption at 3440 cm$^{-1}$ showed the presence of hydroxyl groups. In addition to the above-mentioned signals, the $^{13}$C NMR and DEPT spectra also showed signals due to three methyl, six methylenes (including one oxygenated ones), seven methines (including four oxygen-bearing ones) and six quaternary carbons (including one carbonyl and oxygen-bearing one). HMQC spectroscopy was used to set up the correlation of carbons and protons which were directly bonded (Table 6). The signals at $^{13}$C NMR δ170.413 (s) and 21.341 (q), and $^1$H NMR δ2.120 (s) showed an acetyl group in the structure. The $^{13}$C NMR spectrum at δ98.896 (s) and 67.636 (t) showed the presence of a 7α,20-hemiacetal group.

TABLE 6

$^1$H, $^{13}$C and HMBC Data of rubescensin M

| No. | $^1$H | $^{13}$C | HMBC(H→C) |
|---|---|---|---|
| 1 | 1.553m | 32.016t | |
| 2 | 1.472m | 19.512t | |
| 3 | 1.194m, 1.472m | 42.115t | |
| 4 | | 34.823s | |

TABLE 6-continued

¹H, ¹³C and HMBC Data of rubescensin M

| No. | ¹H | ¹³C | HMBC(H→C) |
|---|---|---|---|
| 5 | 1.393d(5.6) | 56.677d | 4, 6, 9, 10, 18, 19, 20 |
| 6 | 5.260d(5.6) | 74.511d | 4,5,7,8,CH₃CO(6) |
| 7 |  | 98.896s |  |
| 8 |  | 54.660s |  |
| 9 | 2.309d(10.0) | 51.104d | 5, 8, 10, 11, 14, 15, 20 |
| 10 |  | 38.635s |  |
| 11 | 3.925m | 61.605d |  |
| 12 | 1.472m, 2.720m | 43.591t | 9, 11, 13, 16 |
| 13 | 2.493d(9.6) | 46.765d | 8, 11, 14, 15, 16, 17 |
| 14 | 4.399s | 76.764d | 13, 15, 16 |
| 15 | 4.863s | 73.208d | 7, 9, 16, 17 |
| 16 |  | 159.642s |  |
| 17 | 5.186s, 5.239s | 110.824t | 13, 15, 16 |
| 18 | 0.846s | 32.667q | 3, 4, 5, 19 |
| 19 | 1.150s | 22.693q | 3, 4, 5, 6, 18 |
| 20 | 3.925m, 4.138(8.0) | 67.636t | 5, 9, 10 9, 10 |
| CH₃CO(6) | 2.120s | 21.341q | 6, CH₃CO(6) |
| CH₃CO(6) |  | 170.413s |  |

The basic skeleton of Rubescensin M was determined to be 7β-hydroxy-7α,20-epoxy-ent-kaur-16-en-15-ol, which was substituted by four hydroxyl and one acetoxyl groups.

Besides the signals due to one acetoxyl group, the ¹H and ¹³C NMR spectra of Rubescensin M were very similar to those of enmenol, so it was likely that the molecule had the similar skeleton as that of enmenol and the acetyl group was on the 6-position, which was verified by 2D NMR spectroscopic experiments. From gCOSY spectrum, the correlatios were set up among H-5 with H-6, H-9 with H-11, H-11 with H-12a and H-12b, H-12b with H-13.

In the HMBC spectrum, correlations were clearly observed among H-5 (with C-4, C-6, C-9, C-10, C-18, C-19, and C-20), H-6 (with C-4, C-5, C-7, C-8 and C-22), H-9 (with C-5, C-8, C-10, C-11, C-14, C-15, and C-20), H-12b (with C-9, C-11, C-13, and C-16), H-13 (with C-8, C-11, C-14, C-15, C-16, and C-17), H-14 (with C-13, C-15, and C-16), H-15 (with C-7, C-9, C-16, and C-17), H-17a (with C13, C-15, and C-16), H-17b (with C-13, C-15 and C-16), H-18 (with C-3, C-4, C-5, and C-19), H-19 (with C-3, C-4, C-5, C-6, and C-18), H-20a (with C-5, C-9 and C-10), H-20b (with C-9 and C-10), H-21 (with C-6, and C-22).

The relative configuration of the substituents on Rubescensin M was revealed by ROESY spectrum of NOE experiments.

6.2.5 Rabdoternin A

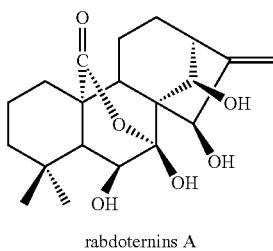

rabdoternins A

Rabdoternin A was isolated and its structure determined. NMR data are shown in Table 7.

TABLE 7

¹H, ¹³C and DEPT Data of Rabdoternin A

| No. | ¹H | ¹³C | HMBC(H→C) |
|---|---|---|---|
| 1 | 2.063dd(1.6, 14.0) | 30.276t |  |
| 2 | 1.310-1.472m | 19.741t |  |
| 3 | 1.160t(13.6), 1.310-1.472m | 41.630t |  |
| 4 |  | 34.978s |  |
| 5 | 1.310-1.472m | 55.630d |  |
| 6 | 3.672d(4.8) | 72.350d | 4, 5, 7, 8 |
| 7 |  | 108.310s |  |
| 8 |  | 54.146s |  |
| 9 | 2.371dd(5.6, 13.2) | 43.755d | 8, 11, 14, 15, 20 |
| 10 |  | 45.277s |  |
| 11 | 0.872m, 1.310-1.472m | 17.798t |  |
| 12 | 1.310-1.472m 2.240m | 32.674t |  |
| 13 | 2.477d(8.8) | 45.994d | 8, 11, 14, 15 |
| 14 | 4.269s | 75.276d | 15, 16 |
| 15 | 4.916t(2.4) | 72.885d | 16 |
| 16 |  | 158.841s |  |
| 17 | 5.136d(2.8), 5.191s | 111.038t | 13, 16, 17 |
| 18 | 0.944s | 31.483q | 3, 4, 5, 19, 20 |
| 19 | 0.791s | 21.168q | 3, 4, 6, 18 |
| 20 |  | 177.648s |  |

6.2.6 Rabdoternin B

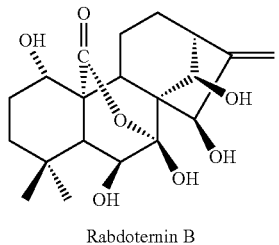

Rabdoternin B

Rabdoternin B was isolated and its structure determined. NMR data are shown in Table 8.

TABLE 8

¹H, ¹³C and HMBC Data of Rabdoternin B

| No. | ¹H | ¹³C | HMBC(H→C) |
|---|---|---|---|
| 1 | 3.448dd(4.8, 11.6) | 74.091d | 9, 20 |
| 2 | 1.467, 1.840 | 31.172t |  |
| 3 | 1.354 | 39.653t |  |
| 4 |  | 34.712s |  |
| 5 | 1.354 | 55.690d | 4, 6, 9, 10, 19, 20 |
| 6 | 3.670d(5.2) | 72.551d | 4, 5, 7, 8 |
| 7 |  | 108.347s |  |
| 8 |  | 53.793s |  |
| 9 | 2.578dd(6.4, 10.4) | 45.144d | 5, 8, 10, 11, 14, 15, 20 |
| 10 |  | 48.218s |  |
| 11 | 1.354, 1.840 | 21.154t |  |
| 12 | 1.467, 2.305m | 32.978t |  |
| 13 | 2.520d(9.2) | 45.972d |  |
| 14 | 4.393s | 75.169d | 15, 16 |
| 15 | 4.944d(0.8) | 72.824d |  |
| 16 |  | 158.940s |  |
| 17 | 5.166d(2.8), 5.215s | 110.586t | 13, 15, 16 |
| 18 | 0.977s | 30.963q | 3, 4, 5, 19 |
| 19 | 0.882s | 20.865q | 3, 4, 5, 18 |
| 20 |  | 176.825s |  |

6.2.7 Rabdoternin C

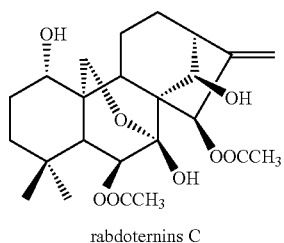

rabdoternins C

Rabdoternin C was isolated and its structure determined. NMR data are shown in Table 9.

TABLE 9

$^1H$, $^{13}C$ and DEPT Data of Rabdoternin C

| No. | $^1H$ | $^{13}C$ | HMBC(H→C) |
|---|---|---|---|
| 1 | 1.484dd(2.4, 8.0), | 32.568t | |
| 2 | 1.345-1.456m | 19.590t | |
| 3 | 1.345-1.456m | 42.397t | |
| 4 | | 34.458s | |
| 5 | 1.557dd(1.2, 7.6) | 54.867d | 6, 9, 10, 18, 19, 20 |
| 6 | 5.320d(7.6) | 74.289d | 5,7,8,18,CO(6) |
| 7 | | 98.675s | |
| 8 | | 52.848s | |
| 9 | 2.341m | 47.710d | 5, 6, 8, 10, 11, 14 |
| 10 | | 37.023s | |
| 11 | 1.210m | 15.787t | |
| 12 | 1.084am, 2.341bm | 32.568t | |
| 13 | 2.478d(9.2) | 46.245d | 6, 8, 11, 12, 14, 16 |
| 14 | 4.557s | 76.452d | |
| 15 | 5.942t(2.0) | 74.600d | 8,13,16,CO(15) |
| 16 | | 158.786s | |
| 17 | 5.100dd(1.2, 2.4), 5.028s | 111.813t | 13, 15, 1615, 16 |
| 18 | 0.853s | 33.342q | 3, 4, 5, 19 |
| 19 | 1.117s | 22.800q | 3, 4, 5, 18 |
| 20 | 3.849dd(1.6, 9.6)4.117dd(1.6, 9.6) | 67.603t | 5, 9, 10, |
| $CH_3CO(15)$ | 1.936s | 21.282q | CO(15) |
| $CH_3CO(15)$ | | 172.698s | |
| $CH_3CO(6)$ | 2.155s | 22.178q | CO(6) |
| $CH_3CO(6)$ | | 172.463s | |

6.2.8 Rubescensin N

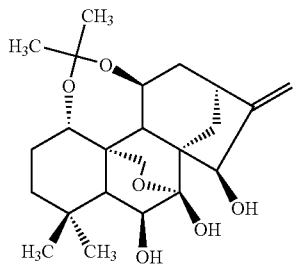

Rubescensin N was isolated and its structure determined using techniques as described above.

6.3 Biological Activities of Exemplary Compounds

Techniques for assaying the biological activities of exemplary compounds are described below.

6.3.1 Materials and Procedures

Cell cultures: The JB6 mouse epidermal cell line Cl 41 or its stable AP-1 luciferase reporter plasmid stable transfectant was maintained with Eagles minimal essential medium (MEM), containing 5% fetal bovine serum (FBS), 2 mM L-glutamine and 25 mg/ml gentamicin or 50 IU/ml penicillin G and 50 µg/ml streptomycin, in an atmosphere of 95% air-5% $CO_2$ at 37° C. Cells were seeded at a density of $5 \times 10^4$ cells/ml and cultured for 24 h. The cells were serum-starved in 0.1% FBS in MEM for 36 h to synchronize the cell cycle into $G_0$ phase. The cells were treated with various concentrations of the test compound or distilled water (as a control) for 1 h, followed, by addition of MTS assay buffer for toxicity studies or 12-O-tetradecanoylphorbol-13-acetate (TPA) or epidermal growth factor (EGF at 10-20 ng/ml) to determine AP-1 activation. Some cells were used for cell transformation assays as described below. For human phenotype expression assays, human colon HCT116, human lung cancer HT460, human skin melanoma SK-MEL-28 or human ovarian SK-OV3 cells were cultured in their respective medium and harvested for soft agar assays.

Cell Proliferation Assay (MTS Assay): Cell proliferation was analyzed using the CELLTITER 96® $AQ_{ueous}$ One Solution Cell Proliferation Assay (Promega, Madison, Wis.) following the instructions provided. In brief, cells synchronized into $G_0$ phase in a 96-well multiplate were treated with individual test compounds and then FBS was added. After an additional 36 h in culture, cells were incubated for 2 h at 37° C. with 3-(4,3-dimethylthiazol-2-yl)-5-(3-carboxymethoxyphenyl)-2-(4-sulfophenyl)-2H-tetrazolium (MTS) reagent in a humidified, 5% $CO_2$ atmosphere. Then the absorbance of a colored formazan product catalyzed by dehydrogenase enzymes in metabolically active cells was recorded at 492 nm with 690 nm as a background. Data were expressed as the percentage of absorbance of untreated control cells.

AP-1 Cell culture and luciferase assay of AP-1 activity: When stimulated, AP-1 induces transcription of several genes involved in cell proliferation, metastasis, and metabolism. TPA or EGF can activate AP-1 and induce cellular transformation in many different cell types. Increased AP-1 activity is associated with malignant transformation and cancer promoting agents, such as UV radiation, growth factors, phorbol esters, and transforming oncogenes. In JB6 mouse epidermal cell lines, TPA or EGF induce AP-1 transcriptional activity in promotion-sensitive (P+) cellular phenotypes. For AP-1 activity studies, confluent monolayers of AP-1 luciferase reporter plasmid stably transfected mouse epidermal JB6 P$^+$1-1 cells were trypsinized, and 8×10$^3$ viable cells suspended in 100 µl of (MEM) supplemented with 5% heat-inactivated FBS, 2 mM L-glutamine, and 25 mg/ml gentamicin. Cells were cultured for 24 h in individual wells of 96-well plates in monolayers at 37° C., 5% CO$_2$ and subsequently starved by culturing them in 0.1% FBS MEM for an additional 24 h. Col-Luc plasmid DNA was used as the AP-1 reporter plasmid. Col-Luc is the 73/63 collagenase promotor driving luciferase containing an AP-1 binding site at −73/63. AP-1 activity was assayed in the stable Col-Luc transfectant in JB6 P+ cells, 41-19. For Col-Luc stable transfectants, after seeding overnight, the cells were treated with various concentrations of a test compound and incubated for 30 min. Following the pretreatment, cells were exposed to TPA (20 ng/ml) or EGF (20 ng/ml) for 24 h. Cells were then harvested by lysis buffer (100 mM K$_2$HPO$_4$, pH 7.8, 1% Triton X-100, 1 mM DTT, 2 mM EDTA). The results are expressed as the relative rate of acetylated product production. Relative AP-1 activity was calculated as described in Dong et al. (1994) *Proc. Natl. Acad. Sci. U.S.A.* 91:609-613 and Dong et al. (1994) *Carcinogenesis* 15:1001-1004. Luciferase activity was measured by a luminometer (MONOLIGHT 2010, Analytical Luminescence Laboratory) 10 s after mixing the extract and luciferase assay reagent.

Anchorage-independent transformation assay: Inhibition of test compounds on TPA or EGF-induced cell transformation or human tumor phenotype expression was investigated under anchorage independent conditions. Samples of 1×10$^4$ cells were exposed to TPA (20 ng/ml) or EGF (20 ng/ml) with or without different concentrations of test compound inl ml 0.33% basal medium Eagle (BME) agar containing 10% FBS over 3.5 ml 0.5% BME agar medium containing 10% FBS. Gingerol was dissolved in 100% ethanol. Ethanol was used in the control group for comparison. The cultures were maintained in a 37° C., 5% CO2 incubator for 14-21 days and the cell colonies were scored by a computerized program integrated with a light microscope. Human tumor cells were treated in a similar manner but no EGF or TPA was needed.

6.3.2 Results

Rubscendepside: Toxicity evaluation with MTS assay in JB6 C141 mouse skin cells identified no Rubscendepside toxicity at the 50 µM level. About 50% cell death was noticed at the 100 µM level (Table 10). It completely inhibits neoplastic transformation in JB6 cell at 50 µM, significantly inhibits HCT116 colon cancer cell growth at 15 µM, moderately inhibits SK-MEL-28 skin caner cell growth at 25 µM, moderately inhibits HT460 lung cancer cell growth at 25 µM (Table 10). Rubscendepside in a nontoxic dose range (25 µM) prevented neoplastic cell transformation in JB6 C141 cells exposed to epidermal growth factor (EGF) in a soft agar assay (FIG. 2). Decreasing colony formation indicates that Rubscendepside is particularly effective against human colon cancer cells (FIG. 3). The compound also had moderate inhibitory effect against human lung cancer cells (FIG. 4) and human skin melanoma cells (FIG. 5).

Rubescensin J: Toxicity evaluation with MTS assay in JB6 C141 mouse skin cells identified about 50% cell death at the 20-25 µM level. It completely inhibits neoplastic transformation in JB6 cell at 40 µM, completely inhibits HCT116 colon cancer cell growth at 20 µM, significantly inhibits SK-MEL-28 skin caner cell growth at 20 µM, moderately inhibits HT460 lung cancer cell growth at 20 µM, moderately inhibits SK-OV-3 Ovarian cancer cell growth at at 20 µM (Table 10). Rubescensin J prevented neoplastic cell transformation in JB6 C141 cells exposed to epidermal growth factor (EGF) in a soft agar assay at 25 µM (FIG. 6). Decreasing colony formation indicates that rubescensin J is particularly effective against human colon cancer cells at 10 µM (FIG. 7) and human skin melanoma cells at 20 µM (FIG. 8). The compound had moderate inhibitory effect against human lung cancer cells (FIG. 9) and human ovarian cancer cells (FIG. 10).

Rubescensin M: Toxicity evaluation with MTS assay in JB6 C141 mouse skin cells identified about 38% cell death at the 100 µM level, and the compound almost completely inhibits neoplastic transformation in JB6 cell at 100 µM, completely inhibited SK-MEL-28 skin caner cell growth at 50 µM. Also, rubescensin M inhibited 90% of HCT116 colon cancer cell growth and 73% of HT460 lung cancer cell growth at 75 µM (Table 10). Rubescensin M prevented neoplastic cell transformation in JB6 C141 cells exposed to epidermal growth factor (EGF) in a soft agar assay at 100 µM (FIG. 11). Decreasing colony formation indicates that rubescensin M is particularly effective against human colon cancer cells (FIG. 12) and human skin melanoma cells (FIG. 13). The compound had moderate inhibitory effect against human lung cancer cells (FIG. 14).

Rabdoternin A: Toxicity evaluation with MTS assay in JB6 C141 mouse skin cells identified about 66% cell death at the 100 µM level. It completely inhibits neoplastic transformation in JB6 cell at 25 µM, SK-MEL-28 skin caner cell growth at 15 µM and completely inhibited HCT116 colon cancer cell growth at 25 µM. Also, rabdoternin A moderately inhibited HT460 lung cancer cell growth at 25 µM (Table 10). Rabdoternin A prevented neoplastic cell transformation in JB6 C141 cells exposed to epidermal growth factor (EGF) in a soft agar assay at 25 µM (FIG. 15). Decreasing colony formation indicates that rabdoternin A is particularly effective against human skin melanoma (FIG. 16) and human colon cancer cells (FIG. 17). The compound had moderate inhibitory effect against human lung cancer cells (FIG. 18).

Rabdoternin B: Toxicity evaluation with MTS assay in JB6 C141 mouse skin cells identified about 60% cell death at the 100 µM level. It completely inhibits neoplastic transformation in JB6 cell at 75 µM and completely inhibited HCT116 colon cancer cell growth at 50 µM (Table 10). Rabdoternin B prevented neoplastic cell transformation in JB6 C141 cells exposed to epidermal growth factor (EGF) in a soft agar assay at 75 µM (FIG. 19). Decreasing colony formation indicates that rabdoternin B is particularly effective against human colon cancer (FIG. 20).

Rabdoternin C: Toxicity evaluation with MTS assay in JB6 C141 mouse skin cells identified about 30% cell death at the 100 µM level. It completely inhibits neoplastic transformation in JB6 cell at 100 µM, significantly inhibited HCT116 colon cancer cell growth at 100 µM. Also, rabdoternin C moderately inhibited SK-MEL-28 skin cancer and HT460 lung cancer cell growth at 100 µM (Table 10). Rabdoternin C prevented 50% neoplastic cell transformation in JB6 C141 cells exposed to epidermal growth factor (EGF) in a soft agar assay at 10 µM (FIG. 21). Decreasing colony formation indicates that rabdoternin C is particularly effective against human colon cancer (FIG. 22). The compound had some inhibitory effect against human skin cancer cells (FIG. 23) and human lung cancer cells (FIG. 24).

TABLE 10

Results of Toxicity and Inhibition of Neoplastic Cell Transformation and Cancer Cell Growth

| Compound | Toxicity (at 100 μM) | Neoplastic Transformation in JB6 Cells | % Inhibition (concentration) | | | |
|---|---|---|---|---|---|---|
| | | | HCT116 Colon Cancer Cells | SK-MEL-28 Skin Cancer | HT 460 Lung Cancer | SK-OV-3 Ovarian Cancer |
| Rabdoternin A | 66 | 100 (25 μM) | 100 (25 μM) | 100 (25 μM) | 10 (25 μM) | |
| Rubescensin M | 38 | 90 | 90 (75 μM) | 100 (50 μM) | 73 (75 μM) | |
| Rubscendepside | 50 | 80-100 (20-50 μM) | 60 (15 μM) | 36 (25 μM) | 37 (25 μM) | |
| Rubescensin J | 50 (20-25 μM) | 83-100 (20-40 μM) | 100 (20 μM) | 50 (20 μM) | 20 (20 μM) | 15 (20 μM) |
| Rabdoternin B | 60 | 100 (75 μM) | 100 (50 μM) | 0 (35 μM) | 0 (35 μM) | |
| Rabdoternin C | 30 | 50 | 68 (100 μM) | 5-10 (100 μM) | 14 (100 μM) | |

7. EXAMPLES

The following example describes the preparation and characterization of exemplary compositions of the invention and demonstrate their inhibitory activities on cellular transformation.

The aerial part of Rabdosia rubescens harvested in China was dried naturally or forcedly, and ground by a crusher to form a biomass. The biomass was extracted three times with 95% ethanol at room temperature. When the solution was condensed, the extract was made into powder by vacuum drying or spray drying. Alteratively, about 1 kg of the biomass was extracted with about 20 L of 70% ethanol or methanol at room temperature and using a Percolater up to 80° C. The extracted solution thus obtained was filtered and concentrated by an evaporator, followed by vacuum drying or spray drying to produce an extract of Rabdosia rubescens.

Three methods were designed to prepare the compositions of the invention.

In a first method, the extract was dissolved in distilled water and isolated by the solvents of hexane and n-butanol. The n-butanol fractions were concentrated and dried by the method of vacuum drying or spray drying. The yield of the fraction to the weight of dried raw material was 5.4% by weight. The diterpenoids (23.5%), depsides (9.1%, 2.1%), and flavonoids (4.8%) content was determined by the HPLC method.

In a second method, a glass column having a diameter of 5 cm and a length of 60 cm was packed with 600 mL of styrene-divinylbenzene series synthetic resin (Diaion HP-20, Mitsubishi Kasei Kogyo K.K.). The packed resin was washed with methanol, and then distilled water. Subsequently, the Rabdosia rubescens extract was applied to the glass column by either the wet method (dissolved in water) or the dry method (dissolved in ethanol or methanol and mixed with resin, then evaporated solvent) method. Then, distilled water was applied at an amount corresponding to about five times the volume of the column to remove a fraction of substances not adsorbed on the styrene-divinylbenzene series synthetic resin, and after that, 85% ethanol or methanol at an amount corresponding to about four times the volume of the column was applied to elute a fraction of substances adsorbed on the styrene-divinylbenzene series synthetic resin. The 85% ethanol or methanol fraction were concentrated and dried by the method of vacuum drying or spray drying. The yield of the fraction relative to the weight of the dried raw material was 7.6% by weight, and the diterpenoids (20.7%), depsides (9.8%, 2.3%), and flavonoids (5.2%) content was determined by the HPLC method.

In a third method, a glass column having a diameter of 5 cm and a length of 60 cm was packed with 600 nL of the polyamide series (Polyamide CC6) synthetic resin, and the packed resin was washed with methanol, and then distilled water. The Rabdosia rubescens extract was applied to the glass column by either the wet method (dissolving in water) or the dry method (dissolving in ethanol or methanol, mixing with resin, followed by evaporating the solvent). Distilled water was then applied at an amount corresponding to about five times the volume of the column to remove a fraction of substances not adsorbed onto the polyamide synthetic resin, and after that, 85% ethanol or methanol at an amount corresponding to about four times the volume of the column was applied to elute a fraction of substances adsorbed on the polyamide series synthetic resin. The 85% ethanol or methanol fraction were concentrated and dried by the method of vacuum drying or spray drying.

The yield of the fraction relative to the weight of dried raw material was 5.7% by weight, and the diterpenoids (36.79%), depside (4.54%, 3.83%), and flavonoids (3.92%) content was determined by the HPLC method. A HPLC chromatogram of a composition prepared by this method is shown in FIG. 25. The relative amounts of diterpenoids, depsides, and other compounds, such as oridonin, ponicidin, D10-5, D8-1, can be used as a standard to compare and characterize elution fractions obtained by this method and other similar methods, and to optimize the method for producing high yields and/or compositions that comprise desired or specific concentrations and/or ratios of diterpenoids and/or depsides. The above-described methods can be scaled up to produce commercial quantities of the compositions by those of skill in the art.

A composition prepared by the third method using methanol as an eluant was tested in cell culture. The effectiveness in preventing neoplastic cell transformation was tested in JB6 C141 cells that are exposed to EGF in a soft agar assay. This Rabdosia extract inhibited cell transformation as follows: 50 or 75 micromolar produced 28% inhibition; 150 micromlar produced 76% inhibition and 300 micromolar produced 98% inhibition. The micromolar concentration is based on an estimated molecular weight of the active compounds which is 250.

8. EXAMPLES

The following example describe the testing of rubescensin J in an animal model which demonstrates its efficacy towards the treatment of skin cancer.

Twenty SKh-1 hairless mice were exposed to UVA to induce skin tumor formation. The mice were divided into two comparable groups equalized based on tumor burden. Rubescensin J was dissolved in DMSO and then brought up to volume in acetone. The two groups. of mice were treated with rubescensin J in acetone, and acetone alone, respectively. The study was blinded so that technicians did not know the identity of the treatments. Five days a week, each mouse received a total of 30 micrograms applied directly on tumor(s) in a volume of 250 microliters. The compound was made fresh each day. Tumor numbers and sizes were monitored and recorded periodically.

Initial measurements were taken on day 1, 14 and 20, and the first treatment was applied on day 21. The experimental group of mice were treated with the compound 5 days a week until the compound was depleted on day 53. Measurement #1 through to #11 were made on day 14, 20, 24, 28, 32, 36, 39, 43, 51, 53, and 84. The numbers of tumor papillomas and the tumor volumes are expressed as a percentage of the number of papillomas and tumor volume on day 1.

As shown in FIG. 26A, on day 84, the number of tumor papillomas in the treated group dropped to nearly 50% of the number of papilloma on day 1. The number of paillomas in the untreated group was about 90%. FIG. 26B shows that the tumor volume on day 84 was about 60% of the volume on day 1. The volume of the untreated group on day 84 was about 120%.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed:
1. A compound having the formula (I):

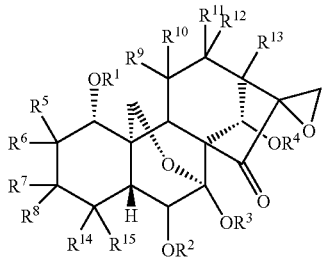

Formula I or a pharmaceutically acceptable salt, or solvate, thereof, wherein:
$R^1$, $R^2$, $R^3$ and $R^4$ are each independently hydrogen, ($C_1$-$C_6$)alkyl, or ($C_1$-$C_{12}$)acyl;
$R^5$, $R^6$, $R^7$, $R^8$, $R^9$, $R^{10}$, $R^{11}$, $R^{12}$, and $R^{13}$ are each independently hydrogen or ($C_1$-$C_6$)alkyl; and
$R^{14}$ and $R^{15}$ are each independently hydrogen or ($C_1$-$C_6$) alkyl.

2. The isolated compound of claim 1, wherein $R^1$, $R^2$, $R^3$ $R^4$ are each independently selected from the group consisting of hydrogen, methyl, ethyl, acetyl, and propionyl.

3. The isolated compound of claim 2, wherein $R^{14}$ and $R^{15}$ are methyl.

4. The isolated compound of claim 1, wherein $R^5$-$R^{13}$ are each independently selected from the group consisting of hydrogen, methyl, and ethyl.

5. The isolated compound of claim 1, wherein at least four of $R^5$-$R^{13}$ are hydrogen.

6. The isolated compound of claim 1, having the formula (II):

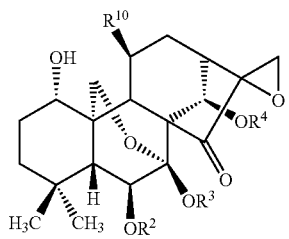

Formula II or a pharmaceutically acceptable salt, or solvate thereof.

7. The isolated compound of claim 6, wherein the compound has the formula:

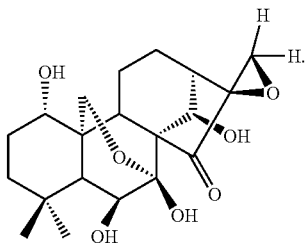

8. A composition comprising a compound of claim 1, wherein said composition is prepared by a method comprising adsorbing an extract of *Rabdosia rubescens* to a synthetic resin comprising polyamide moieties or styrene-divinylbenzene moieties, and eluting the synthetic resin with methanol or ethanol to obtain the composition.

9. The compound of claim 1 in the form of a solvate, wherein the solvent is methanol, and the solvate has a specific rotation, [α]D, equal to -28.6 (c0.06 14).

* * * * *